US006897057B1

(12) United States Patent
Chiocca et al.

(10) Patent No.: US 6,897,057 B1
(45) Date of Patent: May 24, 2005

(54) CELL-SPECIFIC AND/OR TUMOR-SPECIFIC PROMOTER RETARGETING OF HERPES γ 34.5 GENE EXPRESSION

(75) Inventors: E. Antonio Chiocca, Wakefield, MA (US); Richard Y. Chung, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 64 days.

(21) Appl. No.: 09/653,277

(22) Filed: Aug. 31, 2000

Related U.S. Application Data

(60) Provisional application No. 60/151,621, filed on Aug. 31, 1999.

(51) Int. Cl.[7] .............................. C12N 5/00; C12N 7/00; C12P 21/06; A61K 31/70
(52) U.S. Cl. .................... 435/235.1; 435/69.1; 435/325; 514/44
(58) Field of Search ........................ 435/320.1, 6, 69.1, 435/172.5, 235; 514/44

(56) References Cited

U.S. PATENT DOCUMENTS

| 5,288,641 A | | 2/1994 | Roizman ................. 435/320.1 |
| 5,328,688 A | * | 7/1994 | Roizman ................. 424/205.1 |
| 5,585,096 A | * | 12/1996 | Martuza et al. ............ 424/93.2 |
| 5,834,216 A | * | 11/1998 | Roizman et al. ........... 435/7.21 |
| 5,922,328 A | * | 7/1999 | Spector et al. ........... 424/231.1 |
| 6,120,773 A | * | 9/2000 | Roizman ................. 424/205.1 |
| 6,172,047 B1 | * | 1/2001 | Roizman et al. ............... 514/44 |

FOREIGN PATENT DOCUMENTS

| WO | WO 96/00007 | | 1/1996 | | |
| WO | WO 96/03997 | | 2/1996 | | |
| WO | WO 97/04804 | | 2/1997 | | |
| WO | WO98/42195 | * | 10/1998 | .......... | A01N/63/00 |
| WO | WO01/16331 A1 | * | 3/2001 | .......... | C12N/15/38 |

OTHER PUBLICATIONS

Taneja et al., Enhanced antitumor efficacy of a herpes simplex virus mutant isolated by genetic selection in cancer cells; PNAS; Jul. 17, 2001; vol. 98, No. 15; pp 8804–8808.*

Markovitz et al., The Range and Distribution of Murine Central Nervous System Cells Infected with the Y134.5–Mutant of Herpes Simplex Virus 1; Journal of Virology, Jul. 1997, p. 5560–5569, vol. 71, No. 7.*

Chung et al., B–myb Promoter Retargeting of Herpes Simplex Virus γ34.5 Gene–Mediated Virulence toward Tumor and Cycling Cells; Journal of Virology, Sep. 1999, p. 7556–7564.*

Chambers et al., Comparison of genetically engineered herpes simplex viruses for the treatment of brain tumors in a scid mouse model of human malignant glioma; Proc. Natl. Acad. Sci. USA; vol. 92, pp 1141–1415, Feb. 1995, Medical Sciences.*

Yoon et al., An oncolytic herpes simplex virus type 1 selectively destroys diffuse liver metastases from colon carcinoma; The FASEB Journal, vol. 14, pp. 201–311.*

Abe, M. and Kufe, D., "Characterization of Cis–Acting Elements Regulating Transcription of the Human DF3 Breast Carcinoma–Associated Antigen (MUC1) Gene," *Proc. Natl. Acad. Sci. USA* 90:282–286 (1993).

Albarracin, C.T., et al., "The Gonadotropin–Releasing Hormone Receptor Gene Promoter Directs Pituitary–Specific Oncogene Expression in Transgenic Mice," *Endocrinology* 140:2415–2421 (May 1999).

Amizuka, N., et al., "Vitamin D3 Differentially Regulates Parathyroid Hormone/Parathyroid Hormone–Related Peptide Receptor Expression in Bone and Cartilage," *J. Clin. Invest.* 103:373–381 (Feb. 1999).

Andreansky, S.S., et al., "The Application of Genetically Engineered Herpes Simplex Viruses to the Treatment of Experimental Brain Tumors," *Proc. Natl. Acad. Sci. USA* 93:11313–11318 (1996).

Arbuthnot, P., et al., "Hepatoma Cell–Specific Expression of a Retrovirally Transferred Gene is Achieved by Alpha–Fetoprotein but not Insulinlike Growth Factor II Regulatory Sequences," *Hepatology* 22:1788–1796 (1995).

Bennett, J.D., et al., "E2F Binding is Required but Not Sufficient for Repression of B–myb Transcription in Quiescent Fibroblasts," *Oncogene* 13:1073–1082 (1996).

Bischoff, J.R., et al., "An Adenovirus Mutant That Replicates Selectively in p53–Deficient Human Tumor Cells," *Science* 274:373–376 (1996).

Boviatsis, E.J., et al., "Long–Term Survival of Rats Harboring Brian Neoplasms Treated with Ganciclovir and a Herpes Simplex Virus Vector that Retains an Intact Thymidine Kinase Gene," *Cancer Res.* 54:5745–5751 (1994).

Boviatsis, E.J., et al., "Antitumor Activity and Reporter Gene Transfer into Rat Brain Neoplasms Inoculated with Herpes Simplex Virus Vectors Defective in Thymidine Kinase to Ribonucleotide Reductase," *Gene Ther.* 1:323–331 (1994).

Burns, J.C., et al., "Vesicular stomatitis virus G glycoprotein pseudotyped retroviral vectors: Concentration to very high titer and efficient gene transfer into mammalian and non–mammalian cells," *Proc. Natl. Acad. Sci. USA* 90:8033–8037 (1993).

(Continued)

*Primary Examiner*—Joseph Woitach
(74) *Attorney, Agent, or Firm*—Sterne, Kessler, Goldstein & Fox P.L.L.C.

(57) ABSTRACT

The present invention relates to herpes viral mutants and methods of using these viral mutants for selectively targeting tumor cells or other populations of target cells. The viral mutants of the invention are capable of selective targeting due to the use of tumor-specific and/or cell-specific promoters to drive expression of the herpes γ34.5 gene.

25 Claims, 18 Drawing Sheets

OTHER PUBLICATIONS

Caruso, M., et al., "Regression of established macroscopic liver metastases after in situ trasnduction of a suicide gene," *Proc. Natl. Acad. Sci. USA* 90:7024–7028 (1993).

Chambers, R., et al., "Comparison of genetically engineered herpes simplex viruses for the treatment of brain tumors in a scid mouse model of human malignant glioma," *Proc. Natl. Acad. Sci. USA* 92:1411–1415 (1995). (of record).

Chase, M. et al., "An oncolytic viral mutant that delivers the CYP2B1 transgene and augments cyclophosphamide chemotherapy," *Nature Biotechnol.* 16:444–448 (1998).

Chen, S.H., et al., "Gene Therapy for Brain Tumors: Regression of Experimental Gliomas by Adenovirus–Mediated Gene Transfer In Vivo," *Proc. Natl. Acad. Sci. USA* 91:3054–3057 (1994).

Chen, L., et al., "Breast Cancer Selective Gene Expression and Therapy Mediated by Recombinant Adenoviruses Containing the DF3/MUC1 Promoter," *J. Clin. Invest.* 96:2775–2782 (1995).

Chen, L., and Waxman, D.J., "Intratumoral Activation and Enhanced Chemotherapeutic Effect of Oxazaphosphorines following Cytochrome P–450 Gene Transfer: Development of a Combined Chemotherapy/Cancer Gene Therapy Strategy," *Cancer Res.* 55:581–589 (1995).

Chen, L., et al., "Sensitization of Human Breast Cancer Cells to Cyclophosphamide and Ifosfamide by Transfer of a Liver Cytochrome P450 Gene," *Cancer Res.* 56:1331–1340 (1996).

Chou, J. and Roizman, B., "The $\gamma_1$(34.5) Gene of Herpes Simplex Virus 1 Precludes Neuroblastoma Cells from Triggering Total Shutoff of Protein Synthesis Characteristic of Programed Cell Death in Neuronal Cells," *Proc. Natl. Acad. Sci. USA* 89:3266–3270 (1992).

Chou, J., et al., "Association of a $M_r$ 90,000 Phosphoprotein with Protein Kinase PKR in Cells Exhibiting Enhanced Phosphorylation of Translation Initiation Factor eIF–2 Alpha and Premature Shutoff of Protein Synthesis After Infection with Gamma 134.5–Mutants of Herpes Simplex Virus 1," *Proc. Natl. Acad. Sci. USA* 92:10516–10520 (1995).

Chung, R.Y. and Chiocca, E.A., "Gene Therapy for Tumors of the Central Nervous System," *Surg. Oncol. Clin. N. Am.* 7:589–602 (1998).

Clary, B.M., et al., "Transcriptional Targeting for Cancer Gene Therapy," *Surg. Oncol. Clin. N. Am.* 7:565–574 (1998).

Coffey, M.C., et al., "Reovirus Therapy of Tumors with Activated Ras Pathway," *Science* 282:1332–1334 (1998).

Coll–Fresno, P.M., et al., "Cytotoxic Activity of a Diptheria Toxin/FGF6 Mitotoxin on Human Tumour Cell Lines," *Oncogene* 14:243–247 (1997).

Colombo, M.P., et al., "Immunotherapy. I: Cytokine Gene Transfer Strategies," *Cancer Metastasis Rev.* 16:421–432 (1997).

Connors, T.A., "The Choice of Prodrugs for Gene Directed Enzyme Prodrug Therapy of Cancer," *Gene Ther.* 2:702–709 (1995).

Culver, K.W., "Clinical applications of gene therapy for cancer," *Clin. Chem* 40:510–512 (1994).

Dachs, G.U., et al., "Targeting Gene Therapy to Cancer: A Review," *Oncol. Res.* 9:313–325 (1997).

Dehal, S.S., et al., "CYP2D6 Catalyzes Tamoxifen 4–hydroxylation in Human Liver," *Cancer Res.* 57:3402–3406 (1997).

Deonarain, M.P., et al., "Genetic Delivery of Enzymes for Cancer Therapy," *Gene Therapy* 2:235–244 (1995).

Ezzeddine, Z.D., et al., "Selective Killing of Glioma Cells in Culture and in Vivo by Retrovirus Transfer of the Herpes Simplex Virus Thymidine Kinase gene," *New Biol.* 3:608–614 (1991).

Fakhrai, H., et al., "Eradication of Established Intracranial Rat Gliomas by Transforming Growth Factor β Antisense Gene Therapy," *Proc. Natl. Acad. Sci. USA* 93:2909–2914 (1996).

Freeman, S.M., et al., "In Situ Use of Suicide Genes for Cancer Therapy," *Semin. Oncol.* 23:31–45 (1996).

Freytag, S.O., et al., "A Novel Three–Pronged Approach to Kill Cancer Cells Selectively: Concomitant Viral, Double Suicide Gene, and Radiotherapy," *Hum. Gene Ther.* 9:1323–1333 (1998).

Friedlos, F. et al., "Mustard Prodrugs for Activation by *Escherichia coli* Nitroreductase in Gene–Directed Enzyme Prodrug Therapy," *J Med Chem* 40:1270–1275 (1997).

Gage, P.J., et al., "A Cell–Free Recombination System for Site–Specific Integration of Multigenic Shuttle Plasmids Into the Herpes Simplex Virus Type 1 Genome," *J. Virol.* 66:5509–5515 (1992).

Gale, M., et al., "Control of PKR Protein Kinase by Hepatitis C Virus Nonstructural 5A Protein: Molecular Mechanisms of Kinase Regulation," *Mol. Cell. Biol.* 18:5208–5218 (1998).

Glorioso, J.C., et al., "Herpes simplex virus–based vectors," *Seminars in Virology* 3:265–276 (1992).

Glorioso, J.C., et al., "Development and Application of Herpes Simplex Virus Vectors for Human Gene Therapy," *Annu. Rev. Microbiol.* 49:675–710 (1995).

Goeptar, A.R., et al., "Cytotoxicity of Mitomycin C and Adriamycin in Freshly Isolated Rat Hepatocytes: The Role of Cytochrome P450," *Cancer Res.* 54:2411–2418 (1994).

Goldstein, D.J. and Weller, S.K., "Herpes Simplex Virus Type 1–Induced Ribonucleotide Reductase Activity is Dispensable for Virus Growth and DNA Synthesis: Isolation and Characterization of an ICP6 *lacZ* Insertion Mutant," *J. Virol.* 62:196–205 (1988).

Goldstein, D.J. and Weller, S.K., "An ICP6::*lacZ* Insertional Mutagen is Used to Demonstrate That the UL52 Gene of Herpes Simplex Virus Type 1 is Required for Virus Growth and DNA Synthesis," *J. Virol.* 62:2970–2977 (1988).

Guillot, P.V., et al., "A Vascular Bed–Specific Pathway Regulates Cardiac Expression of Endothelial Nitric Oxide Synthase," *J. Clin. Invest.* 103:799–805 (Mar. 1999).

Hallenbeck, P.L., et al., "A Novel Tumor–Specific Replication–Restricted Adenoviral Vector for Gene Therapy of Hepatocellular Carcinoma," *Hum. Gene Ther.* 10:1721–1733 (Jul. 1999).

Hart, I.R., et al., "Targeted Therapy for Malignant Melanoma," *Curr. Opin. Oncol.* 6:221–225 (1994).

Hart, I.R., "Tissue Specific Promoters in Targeting Systemically Delivered Gene Therapy," *Semin. Oncol.* 23:154–158 (1996).

He, B., et al., "The $\gamma_1$34.5 Protein of Herpes Simplex Virus 1 Has the Structural and Functional Attributes of a Protein Phosphatase 1 Regulatory Subunit and is Present in a High Molecular Weight Complex with the Enzyme in Infected Cells," *J. Biol. Chem.* 273:20737–20743 (1998).

Hollywood, D, and Hurst, H., "A Novel Transcription Factor, OB2–1, is Required for Overexpression of the Proto–Oncogene c–erbB–2 in Mammary Tumour Lines," *EMBO J 12*:2369–2375 (1993).

Hunter, W.D., et al., "Attenuated, Replication–Competent Herpes Simplex Virus Type 1 Mutant G207: Safety Evaluation of Intracerebral Injection in Nonhuman Primates," *J. Virol. 73*:6319–6326 (Aug. 1999).

Hwang, J.J., et al., "Novel Retroviral Vector Transferring a Suicide Gene and a Selectable Marker Gene with Enhanced Gene Expression by Using a Tetracycline–Responsive Expression System," *J. Virol. 70*:8138–8141 (1996).

Ikeda, K., et al., "Oncolytic Virus Therapy of Multiple Tumors in the Brain Requires Suppression of Innate and Elicited Antiviral Responses," *Nat. Med. 5*:881–887 (1999).

Jain, R.K., "Delivery of Molecular Medicine to Solid Tumors," *Science 271*:1079–1080 (1996).

Jérôme, V., and Müller, R., "Tissue–Specific, Cell Cycle–Regulated Chimeric Transcription Factors for the Targeting of Gene Expression to Tumor Cells," *Hum. Gene Ther. 9*:2653–2659 (1988).

Johnson, P.A., et al., "Cytotoxicity of a Replication–Defective Mutant of Herpes Simplex Virus Type 1," *J. Virol. 66*:2952–2965 (1992).

Kappel, A., et al., "identification of Vascular Endothelial Growth Factor (VEGF) Receptor–2 (*Flk*–1) Promoter/Enhancer Sequences Sufficient for Angioblast and Endothelial Cell–Specific Transcription in Transgenic Mice," *Blood 93*:4284–4292 (Jun. 1999).

Kesari, S., et al., "Therapy of Experimental Human Brain Tumors Using a Neuroattenuated Herpes Simplex Virus Mutant," *Lab. Invest. 73*:636–648 (1995).

Kooby, D.A., et al., "Oncolytic Viral Therapy for Human Colorectal Cancer and Liver Metastases Using a Multi–Mutated Herpes Simplex Virus Type–1 (G207)," *FASEB J. 13*:1325–1334 (Aug. 1999).

Kramm, C.M., et al., "Therapeutic Efficiency and Safety of a Second–Generation Replication–Conditional HSV1 Vector for Brain Tumor Gene Therapy," *Hum. Gene Ther. 8*:2057–2068 (1997).

Lam, E.W., et al., "Cell–cycle regulation of human B–myb transcription," *Gene 160*:277–281 (1995).

Lan, K–H., et al., "In Vivo Selective Gene Expression and Therapy Mediated by Adenoviral Vectors for Human Carcinoembryonic Antigen–producing Gastric Carcinoma," *Cancer Res. 57*:4279–4284 (1997).

LeBlanc, G.A. and Waxman, D.J., "Interaction of Anticancer Drugs with Hepatic Monooxygenase Enzymes," *Drug Metab. Rev. 20*:395–439 (1989).

Lorence, R.M. et al., "Complete Regression of Human Neuroblastoma Xenografts in Athymic Mice After Local Newcastle Disease Virus Therapy," *J. Natl. Cancer. Inst. 86*:1228–1233 (1994).

Lukas, J., et al., "Deregulated Expression of E2F Family Members Induces S–phase Entry and Overcomes p16INK4A–Mediated Growth Suppression," *Mol. Cell. Biol. 16*:1047–1057 (1996).

Lundwall, A., "Characterization of the Gene for Prostate–Specific Antigen, a Human Glandular Kallikrein," *Biochem. Biophys. Res. Commun. 161*:1151–1156 (1989).

Lyon, J., et al., "The Role of Myb Proteins in Normal and Neoplastic Cell Proliferation," *Crit. Rev.Oncogenesis 5*:373–388 (1994).

Manome, Y., et al., "Gene therapy for malignant gliomas using replication imcompetent retroviral and adenoviral vectors encoding the cytochrome P450 2B1 gene together with cyclophosphamide," *Gene Therapy 3*:513–520 (1996).

Markert, J.M., et al. "Expanded Spectrum of Viral Therapy in the Treatment of Nervous System Tumors,",*J. Neurosurg. 77*:590–594 (1992).

Martuza, R.L., et al., "Experimental Therapy of Human Glioma by Means of a Genetically Engineered Virus Mutant," *Science 252*:854–856 (1991).

Martuza, R.L., "Conditionally Replicating Herpes Vectors For Cancer Therapy," *J. Clin. Invest. 105*:841–846 (Apr. 2000).

Massie, B., et al., "Inducible Overexpression of a Toxic Protein by an Adenovirus Vector with a Tetracycline–Regulatable Expression Cassette," *J. Virol.72*:2289–2296 (1998).

McLauchlan, J., and Clements, J.B., "Organization of the Herpes Simplex Virus Type 1 Transcription Unit Encoding Two Early Proteins with Molecular Weights of 140000 and 40000," *J. Gen. Virol. 64*:997–1006 (1983).

Miller, N., and Vile, R., "Targeted vectors for gene therapy," *FASEB J. 9*:190–199 (1995).

Miller, N. and Whelan, J., "Progress in Transcriptionally Targeted and Regulatable Vectors for Genetic Therapy," *Hum. Gene Ther. 8*:803–815 (1997).

Mineta, T., et al., "Treatment of Malignant Gliomas Using Ganciclovir–Hypersensitive, Ribonucleotide Reduces–Deficient Herpes Simplex Viral Mutant," *Cancer Res. 54*:3969–3966 (1994).

Mineta, T., et al., "Attenuated Multi–Mutated Herpes Simplex Virus–1 for the Treatment of Malignant Gliomas," *Nature Med 1*:938–943 (1995).

Miyatake, S., et al., "Transcriptional Targeting of Herpes Simplex Virus for Cell–Specific Replication," *J. Virol. 71*:5124–5132 (1997).

Mohr, I. and Bluzman, Y., "A Herpesvirus Genetic Element Which Affects Translation in the Absence of the Viral GADD34 Function," *EMBO J. 15*:4759–4766 (1996).

Moolten, F.L. and Wells, J.M., "Curability of Tumors Bearing Herpes Thymidine Kinase Genes Transferred by Retroviral Vectors," *J. Natl. Cancer Inst. 82*:297–300 (1990).

Moolten, F.L., "Drug sensitivity ("suicide") genes for selective cancer chemotherapy," *Cancer Gene Ther. 1*:279–287 (1994).

Mullen, C.A., et al., "Tumors Expressing the Cytosine Deaminase Suicide Gene Can Be Eliminated in Vivo with 5–Fluorocytosine and induce protective immunity to Wild Type Tumor," *Cancer Res. 54*:1503–1506 (1994).

Nagayama, Y., et al., "Enhanced Efficacy of Transcriptionally Targeted Suicide Gene/Prodrug Therapy for Thyroid Carcinoma with the Cre–loxP System," *Cancer Res. 59*:3049–3052 (Jul. 1999).

Ng, S.F. and Waxman D.J., "Activation of thio–TEPA cytotoxicity toward human breast cancer cells by hepatic cytochrome P450," *Intl. J. Oncology 2*:731–738 (1993).

Nilaver, G., et al., "Delivery of Herpesvirus and Adenovirus to Nude Rat Intracerebral Tumors After Osmotic Blood–Brain Barrier Disruption," *Proc. Natl. Acad. Sci. USA 92*: 9829–9833 (1995).

O'Malley, B.W., Jr., et al., "Combination Gene Therapy for Oral Cancer in a Murine Model," *Cancer Res. 56*:1737–1741 (1996).

Oldfield, E., et al., "Gene Therapy for the Treatment of Brain Tumors Using Intra–Tumoral transduction with the Thymidine Kinase Gene and Intravenous Ganciclovir," *Hum. Gene Ther.* 4:39–69 (1993).

Osaki, T., et al., "Gene Therapy for Carcinoembryonic Antigen–Producing Human Lung Cancer Cells by Cell Type–Specific Expression of Herpes Simplex Virus Thymidine Kinase Gene," *Cancer Res.* 54:5258–5261 (1994).

Perng, G.–C., et al., "An Avirulent ICP34.5 Deletion Mutant of Herpes Simplex Virus Type 1 Is Capable of In Vivo Spontaneous Reactivation," *J. Virol.* 69:3033–3041 (1995).

Pyles, R.B. and Thompson, R.I., "Evidence That the Herpes Simplex Virus Type 1 Uracil DNA Glycosylase is Required for Efficient Viral Replication and Latency in the Murine Nervous System," *J. Virol.* 68:4963–4972 (1994).

Pyles, R.B., et al., "A Novel Multiply–Mutated HSV–1 Strain for the Treatment of Human Brain Tumors," *Hum. Gene Ther.* 8:533–544 (1997).

Rainov, N.G., et al., "Retrovirus–Mediated Gene Therapy of Experimental Brain Neoplasms Using the Herpes Simplex Virus–Thymidine Kinase/Ganciclovir Paradigm," *Cancer Gene Therapy* 3:99–106 (1996).

Rain, N.G., et al., "New Prodrug Activation Gene Therapy for Cancer Using Cytochrome P450 4B1 and 2–aminoanthracene/4–ipomeanol," *Hum. Gene Ther.* 9:1261–1273 (1998).

Ram, Z., et al., "Therapy of Malignant Brain Tumors by Intratumoral Implantation of Retroviral Vector–Producing Cells," *Nature Medicine* 3:1354–1361 (1997).

Ray, M.K., et al., "β Cell–Specific Ablation of Target Gene USing Cre–loxP System in Transgenic Mice," *J. Surg. Res.* 84:199–203 (Jun. 1999).

Rodriguez, R., et al., "Prostate Attenuated Replication Competent Adenovirus (ARCA) CN706: A Selective Cytotoxic for Prostate–Specific Antigen–Positive Prostate Cancer Cells," *Cancer Res.* 57:2559–2563 (1997).

Roizman, B. and Jenkins, F.J., "Genetic Engineering of Novel Genomes of Large DNA Viruses," *Science* 229:1208–1214 (1985).

Rosenberg, S.A., et al., "Human Gene Marker/Therapy Clinical Protocols," *Hum. Gene Ther.* 11:919–979 (Apr. 2000).

Roth, J.A., et al., "Retrovirus–mediated Wild–Type p53 Gene Transfer to Tumors of Patients with Lung Cancer," *Nature Med.* 2:985–991 (1996).

Roth, J.A. and Cristiano, R.J., "Gene Therapy for Cancer: What Have We Done and Where are We Going?" *J. Natl. Cancer Inst.* 89:21–39 (1997).

Schnierle, B.S. and Groner, B., "Retroviral Targeted Delivery," *Gene Therapy* 3:1069–1073 (1996).

Spear, M.A., et al., "Targeting gene therapy vectors to CNS malignancies," *J. NeuroVirol.* 4:133–147 (1998).

Spear, M.A., "Gene Therapy of Gliomas: Receptor and transcriptional Targeting," *Anticancer Research* 18:3223–3232(1998).

Toda, M., et al., "In Situ Cancer Vaccination: An IL–12 Defective Vector/Replication–Competent Herpes Simplex Virus Combination Induces Local and Systemic Antitumor Activity," *J. Immunol.* 160:4457–4464 (1998).

Toda, M., et al., "Herpes Simplex Virus as an In Situ Cancer Vaccine for the Induction of Specific Anti–Tumor Immunity," *Hum. Gene. Ther.* 10:385–393 (Feb. 1999).

Ueki, K., et al., "CDKN2/p16 or RB Alterations Occur in the Majority of Glioblastomas and Are Inversely Correlated," *Cancer Res.* 56:150–153 (1996).

Vile, R.G. and Hart, I.R., "In Vitro and in Vivo Targeting of Gene Expression to Melanoma Cells," *Cancer Res.* 53:962–967 (1993).

Vile, R.G., "Tumor–specific gene expression," *Semin. Cancer Biol.* 5:429–436 (1994).

Walther, W., and Stein, U., "Targeted Vectors for Gene Therapy of Cancer and Retroviral Infections," *Mol. Biotechnol.* 6:267–286 (1996).

Walther, W. and Stein, U., "Cell type specific and inducible promoters for vectors in gene therapy as an approach for cell targeting," *J. Mol. Med.* 74:379–392 (1996).

Wei, M.X., et al., "Experimental Tumor Therapy in mice Using the Cyclophosphamide–Activating Cytochrome P450 2B1 Gene," *Hum. Gene Ther.* 5:969–978 (1994).

Yang, C., et al., *"Paired*–Like Homeodomain Proteins, Phox2a and Phox2b, are Responsible for Noradrenergic Cell–Specific Transcription of the Dopamine ⊖–hydroxylase Gene," *J. Neurochem.* 71:1813–1826 (1998).

Nakamura, H., et al., "Oncolysis of Colon Carcinoma Liver Metastasis in Genetically Engineered HSV–1 Vector MTB34.5," *Proc. Am. Assoc. Cancer Res. Ann. Meet.* 41:466 Abstract No. 2970 (Mar. 2000).

Yoon, S.S. and Tanable, K.K., "Surgical Treatment and Other Regional Treatments for Colorectal Cancer Liver Metastases," *Oncologist.* 4:197–208 (1999).

Munaut, C., et al., "Murine Matrix Metalloproteinase 9 Gene," *J. Biol. Chem.* 274:5588–5596 (1999).

\* cited by examiner

D 1    2    3    4

γ34.5 PROBE

CELL-SPECIFIC AND/OR TUMOR-SPECIFIC PROMOTER RETARGETING OF HERPES γ 34.5 GENE EXPRESSION

CROSS-REFERENCE TO RELATED APPLICATION

This application claims the benefit of U.S. Provisional Application No. 60/151,621, filed Aug. 31, 1999. The content of this application is relied upon and incorporated by reference in its entirety.

STATEMENT AS TO RIGHTS TO INVENTIONS MADE UNDER FEDERALLY-SPONSORED RESEARCH AND DEVELOPMENT

At least part of the work performed during development of this invention utilized a grant from the National Cancer Institute, Grant No. CA69246. The U.S. Government has certain rights in this invention.

BACKGROUND OF THE INVENTION

1. Field of the Invention

The present invention relates to a herpes viral mutant capable of selectively targeting tumor cells and/or other specific cell populations. More particularly, the present invention relates to the use of cell-specific and/or tumor-specific promoters to retarget mutant herpes viral vectors toward tumors and specific cell types. The cell-specific and/or tumor-specific promoter is used to drive expression of the herpes gamma (γ) 34.5 gene, whose gene product is responsible for producing large quantities of progeny virus in infected cells.

Herpes vectors without the γ34.5 gene do not replicate well, which is desirable for clinical use. However, the absence of the γ34.5 gene, also diminishes the ability of the virus to kill tumors or any other infected tissue. The present invention allows for the production of high amounts of herpes virus in cells that can use the cell- and/or tumor-specific promoter. Cells that cannot turn on the promoter, however, do not support viral replication, thus saving them and their neighboring cells from active and noxious viral infection and replication, thus, redirecting herpes' virulence towards desired target cells.

2. Related Art

A. Conventional Cancer Therapies

Neoplasia is a process that occurs in cancer, by which the normal controlling mechanisms that regulate cell growth and differentiation are impaired, resulting in progressive growth. This impairment of control mechanisms allows a tumor to enlarge and occupy spaces in vital areas of the body. If the tumor invades surrounding tissue and is transported to distant sites (metastases) it will likely result in death of the individual.

In 1999, in the United States alone, approximately 563, 100 people, or about 1,500 people per day, are expected to die of cancer. (Landis, et al., "Cancer Statistics, 1999," *CA Canc. J. Clin.* 49:8–31 (1999)). Moreover, cancer is a leading cause of death among children aged 1 to 14 years, second only to accidents. Id. Thus, clearly there is a need for the development of new cancer therapies.

1. Common Limitations of Conventional Therapies

The desired goal of cancer therapy is to kill cancer cells preferentially, without having a deleterious effect on normal cells. Several methods have been used in an attempt to reach this goal, including surgery, radiation therapy, and chemotherapy.

Surgery was the first cancer treatment available, and still plays a major role in diagnosis, staging, and treatment of cancer, and may be the primary treatment for early cancers (see, Slapak, C. A. and Kufe, D. W., "Principles of Cancer Therapy," in *Harrison's Principles of Internal Medicine*, Fauci, A. S. et al., eds., 14th Ed., McGraw-Hill Cos., Inc., New York, 1998, at 524). However, although surgery may be an effective way to cure tumors confined to a particular site, these tumors may not be curable by resection due to micrometastatic disease outside the tumor field. Id. Any cancer showing a level of metastasis effectively cannot be cured through surgery alone. Id.

Radiation therapy is another local (nonsystemic) form of treatment used for the control of localized cancers. Id at 525. Many normal cells have a higher capacity for intercellular repair than neoplastic cells, rendering them less sensitive to radiation damage. Radiation therapy relies on this difference between neoplastic and normal cells in susceptibility to damage by radiation, and the ability of normal organs to continue to function well if they are only segmentally damaged. Id. Thus, the success of radiation therapy depends upon the sensitivity of tissue surrounding the tumor to radiation therapy. Id. Radiation therapy is associated with side effects that depend in part upon the site of administration, and include fatigue, local skin reactions, nausea and vomiting. Id at 526. In addition, radiation therapy is mutagenic, carcinogenic and teratogenic, and may place the patient at risk of developing secondary tumors. Id.

Other types of local therapy have been explored, including local hyperthermia (Salcman, M., et at., *J. Neuro-Oncol.* 1:225–236 (1983)), photoradiation therapy (Cheng, M. K., et al., *Surg. Neurol.* 25:423–435 (1986)), and interstitial radiation (Gutin, P. H., et al., *J. Neurosurgery* 67:864–873 (1987)). Unfortunately, these therapies have been met with only moderate success.

Local treatments, such as radiation therapy and surgery, offer a way of reducing the tumor mass in regions of the body that are accessible through surgical techniques or high doses of radiation therapy. However, more effective local therapies with fewer side effects are needed. Moreover, these treatments are not applicable to the destruction of widely disseminated or circulating tumor cells eventually found in most cancer patients. To combat the spread of tumor cells, systemic therapies are used.

One such systemic treatment is chemotherapy. Chemotherapy is the main treatment for disseminated, malignant cancers (Slapak, C. A. and Kufe, D. W., "Principles of Cancer Therapy," in *Harrison's Principles of Internal Medicine*, Fauci, A. S. et al., eds., 14th Ed., McGraw-Hill Cos., Inc., New York, 1998, 527). However, chemotherapeutic agents are limited in their effectiveness for treating many cancer types, including many common solid tumors. Id. This failure is in part due to the intrinsic or acquired drug resistance of many tumor cells. Id at 533. Another drawback to the use of chemotherapeutic agents is their severe side effects. Id. at 532. These include bone marrow suppression, nausea, vomiting, hair loss, and ulcerations in the mouth. Id. Clearly, new approaches are needed to enhance the efficiency with which a chemotherapeutic agent can kill malignant tumor cells, while at the same time avoiding systemic toxicity.

2. Challenges Presented by Central Nervous System Tumors

Another problem in cancer treatment is that certain types of cancer, e.g., gliomas, which are the most common primary malignancy arising in the human brain, defy the current modalities of treatment. Despite surgery, chemotherapy, and radiation therapy, glioblastoma multiforme, the most common of the gliomas, is almost universally fatal (Schoenberg, in *Oncology of the Nervous System*, M. D. Walker, ed., Boston, Mass., Martinus Nijhoff (1983); Levin et al., Chapter 46 in *Cancer: Principles and Practice of Oncology*, vol. 2, 3rd ed., De Vita et al., eds., Lippincott Press, Philadelphia (1989), pages 1557–1611).

Gliomas represent nearly 40% of all primary brain tumors, with glioblastoma multiforme constituting the most malignant form (Schoenberg, "The Epidemiology of Nervous System Tumors," in *Oncology of the Nervous System*, Walker, ed., Cold Spring Harbor Laboratory, Cold Spring Harbor, N.Y. (1983)). The five year survival rate for persons with this high grade type of astrocytoma is less than 5 percent, given the current treatment modalities (surgery, radiation therapy and/or chemotherapy) (Mahaley et al., *Neurosurgery* 71: 826–836 (1989); Schoenberg, in *Oncology of the Nervous System*, Walker, ed., Cold Spring Harbor Laboratory, Cold Spring Harbor, N.Y. (1983); Kim et al., *J. Neurosurg.* 74:27–37 (1991), Daumas-Duport et al., *Cancer* 2:2152–2165 (1988)). After treatment with radiation therapy, glioblastomas usually recur locally. Hochberg, F. H., et al., *Neurology* 30:907–911 (1980). Neurologic dysfunction and death in an individual with glioblastoma are due to the local growth of the tumor. Systemic metastases are rare. Id. For this reason, regional cancer therapy methods, rather than systemic methods, may be especially suitable for the treatment of glioblastomas.

Moreover, glioblastomas are resistant to many chemotherapeutic agents, perhaps due to the proliferative characteristics of this tumor type. Many chemotherapeutic agents are cell-cycle-active, i.e., cytotoxic primarily to actively cycling cells (Slapak, C. A., and Kufe, D. W., "Principles of Cancer Therapy," in *Harrison's Principles of Internal Medicine*, Fauci, A. S. et al., eds., 14th Ed., McGraw-Hill Cos., Inc., New York, 1998, 527). Generally, chemotherapy is most effective for cancers with a small tumor burden where the growth fraction of the tumor is maximal. Id. The growth fraction for glioblastoma tumors is only 30%, with the remaining 70% of cells being in $G_0$, a resting phase (cells in $G_0$ may die or may re-enter the active cell cycle (Yoshii et al., *J. Neurosurg.* 65:659–663 (1986)). While the 30% of glioblastoma cells that are actively dividing contribute to the lethal progression of this tumor, the 70% that are quiescent are responsible for the resistance of these tumors to a number of chemotherapeutic agents that target actively proliferating cells.

Unfortunately, regional treatments, such as surgery and radiation therapy have also found limited success in the treatment of glioblastomas (Burger et al., *J. Neurosurg.* 58:159–169 (1983); Wowra et al., *Acta Neurochir.* (*Wien*) 99:104–108 (1989); Zamorano et al., *Acta Neurochir. Suppl.* (*Wien*) 46:90–93 (1989)). Surgical treatment for glioblastomas is hampered by the lack of distinct boundaries between the tumor and the surrounding parenchyma, and by the migration of tumor cells in the white matter tracts extending out from the primary site (Burger et al., *J. Neurosurg.* 58:159–169 (1983)), which preclude their complete removal. Radiation therapy, which targets rapidly proliferating cells, is limited by the low growth fraction in glioblastomas, and by the radiation sensitivity of adjacent normal tissue (Wowra et al., *Acta Neurochir.* (*Wien*) 99:104–108 (1989); Zamorano et al., *Acta Neurochir. Suppl.* (*Wien*) 46:90–93 (1989)). Thus, new approaches are especially needed to treat brain tumors.

B. Non-Traditional Approaches to Cancer Therapy Using Viruses

One non-traditional approach to cancer therapy employs mutated viruses to target neoplastic cells. See, Chung, R. Y. and Chiocca, E. A., *Surg. Oncol. Clin. N. Am.* 7:589–602 (1998)).

Proposed viral cancer therapies include two distinct approaches: (1) direct cell killing (oncolysis) by a mutagenized virus (Martuza et al., *Science* 252:854–856 (1991); Mineta et al., *Nature Med* 1:938–943 (1995); Boviatsis et al., *Cancer Res.* 54: 5745–5751 (1994); Kesari, et al., *Lab. Invest.* 73: 636–648 (1995); Chambers et al., *Proc. Natl. Acad. Sci. USA* 92: 1411–1415 (1995); Lorence, R. M. et al., *J. Natl. Cancer. Inst.* 86: 1228–1233 (1994); Bischoff, et al., *Science* 274: 373–376 (1996); Rodriguez et al., *Cancer Res.* 57: 2559–2563 (1997)); and (2) the use of viral vectors to deliver a transgene whose expression product activates a chemotherapeutic agent (Wei et al., *Human Gene Therapy* 5: 969–978 (1994); Chen and Waxman, *Cancer Res.* 55: 581–589 (1995); Moolten, *Cancer Gene Ther.* 1: 279–287 (1994); Fakhrai et al., *Proc. Natl. Acad. Sci. USA* 93: 2909–2914 (1996); Roth et al., *Nature Med.* 2:985–991 (1996); Moolten, *Cancer Res.* 46: 5276–5281 (1986); Chen et al., *Proc. Natl. Acad. Sci. USA* 91: 3054–3057 (1994)).

1. Viral Oncolysis

The genetic engineering of viruses for use as oncolytic agents has initially focused on the use of replication-incompetent viruses. This strategy was hoped to prevent damage to non-tumor cells by the viruses. A major limitation of this approach was that these replication-incompetent viruses required a helper virus to be able to integrate and/or replicate in a host cell. One example of the viral oncolysis approach, the use of replication-defective retroviruses for treating nervous system tumors, requires the implantation of a producer cell line to spread the virus. These retroviruses are limited in their effectiveness, because each replication-defective retrovirus particle can enter only a single cell and cannot productively infect others thereafter. Therefore, they cannot spread far from the producer cell, and are unable to completely penetrate a deep, multilayered tumor in vivo (Markert et al., *Neurosurg.* 77:590 (1992); Rarn et al., *Nature Medicine* 3:1354–1361 (1997)).

More recently, genetic engineering of oncolytic viruses has focused on the generation of replication-conditional viruses in an attempt to avoid systemic infection, while allowing the virus to spread to other tumor cells. Replication-conditional viruses are designed to preferentially replicate in actively dividing cells, such as tumor cells. Thus, these viruses should target tumor cells for oncolysis, and replicate in these cells so that the virus can spread to other tumor cells.

Some recent strategies for creating replication-conditional viral mutants as anticancer agents have employed mutations in selected adenoviral or herpes simplex virus type 1 (HSV-1) genes to render them replication-conditional (Martuza, R. L., et al., *Science* 252:854–856 (1991); Mineta, T., et al., *Nature Med* 1:938–943 (1995); Boviatsis, E. J., et al., *Cancer Res.* 54: 5745–5751 (1994); Kesari, S., et al., *Lab. Invest.* 73: 636–648 (1995); Chambers, R., et al., *Proc. Natl. Acad. Sci. USA* 92: 1411–1415 (1995); Lorence, R. M. et al., *J. Nat. Cancer. Inst.* 86: 1228–1233 (1994); Bischoff, J. R., et al., *Science* 274: 373–376 (1996); Rodriguez, R., et al., *Cancer Res.* 57: 2559–2563 (1997)). For example, an adenovirus with a deletion in the E1B-55 Kd encoding gene has been shown to selectively replicate in p53-defective tumor cells (Bischoff, J. R., et al., supra).

Two broad types of replication-conditional HSV mutants in a single gene have been studied to date. The first consists of viral mutants with defects in the function of a viral gene needed for nucleic acid metabolism, such as thymidine kinase (Martuza, R. L., et al., *Science* 252:854–856 (1991)), ribonucleotide reductase (RR) (Goldstein, D. J. & Weller, S. K., *J. Virol.* 62:196–205 (1988); Boviatsis, E. J., et al., *Gene Ther.* 1:323–331 (1994); Boviatsis, E. J., et al., *Cancer Res.* 54:5745–5751 (1994); Mineta, T., et al., *Cancer Res.* 54:3363–3366 (1994)), or uracil-N-glycosylase (Pyles, R. B. and Thompson, R. I., *J. Virol.* 68:4963–4972 (1994)).

The second consists of viral mutants with defects in the function of the γ34.5 gene (Chambers, R., et al., *Proc. Natl. Acad. Sci. USA* 92:1411–1415 (1995)), which functions as a virulence factor by markedly enhancing the viral burst size of infected cells through suppression of the shutoff of host protein synthesis (Chou, J., et al., *Science* 250:1262–1266 (1990); Chou, J. and Roizman, B., *Proc. Natl. Acad. Sci. USA* 89:3266–3270 (1992)).

These single mutant strains have certain inherent limitations, including resistance to ganciclovir and acyclovir for TK mutants (Mineta, T., et al., *Cancer Res.* 54:3363–3366 (1994)), the risk of reversion to wild-type by a single recombination event with wild-type virus, and reduced oncolytic efficacy for γ34.5 mutants, at least in certain tumor cell lines (Kramm, C. M., et al., *Hum. Gene Ther.* 8:2057–2068 (1997); Mohr. 1. & Bluzman, Y., *EMBO J.* 15:4759–4766 (1996); Toda, M., et al., *Hum. Gene Ther.* 9:2177–2185 (1998)).

In an effort to decrease the risk of wild-type recombination, HSV viruses that are multiply mutated have been developed. These include mutants G207 (Mineta, T., et al., *Nat. Med* 1:938–943 (1995); U.S. Pat. No. 5,585,096, issued Dec. 17, 1996 to Martuza et al.), and MGH1 (Kramm, C. M., et al., *Hum. Gene Ther.* 8:2057–2068 (1997), which possess deletions of both copies of γ34.5 and an insertional mutation of RR.

Another multiply mutated HSV virus is the γ34.5/uracil DNA glycosylase (FNG) mutant strain 3616UB (Pyles, R. B., et al., *Hum. Gene Ther.* 8:533–544 (1997)). These double mutant strains demonstrate markedly reduced neurovirulence upon direct intracranial injection, retain sensitivity to ganciclovir, and show relatively selective replication in tumor cells compared to normal tissues. Such double mutant HSV strains retain the defective γ34.5 gene, thus demonstrating little virulence towards normal tissues. Although, they clearly demonstrate oncolytic effects against tumor cells, such effects are less than those observed in mutants with intact γ34.5 genes (Kramm, C. M., et al., *Hum. Gene Ther.* 8:2057–2068 (1997); Qureshi, N. and Chiocca, E. A., unpublished data). On the other hand, the toxicity exhibited by an intact γ34.5 gene might reduce the potential application of the latter viruses as oncolytic agents.

2. Viral Delivery of Anticancer Transgenes

The second approach in viral cancer therapy is the viral delivery of anticancer transgenes, whereby the phenotype of the target tumor cells is genetically altered to increase the tumor's drug sensitivity and responsiveness. This approach involves directly transferring a "chemosensitization" or "suicide" gene encoding a prodrug activation enzyme to malignant cells, in order to confer sensitivity to otherwise innocuous agents (Moolten, F. L., *Cancer Gene Therapy* 1:279–287 (1994); Freeman, S. M., et al., *Semin. Oncol.* 23:31–45 (1996); Deonarain, M. P., et al., *Gene Therapy* 2:235–244 (1995)).

Several prodrug activation genes have been studied for application in cancer gene therapy. In one example, herpes simplex virus thymidine kinase (HSV-TK) in combination with the prodrug ganciclovir represents a prototypic prodrug/enzyme activation system known in the art with respect to its potential applications in cancer gene therapy. HSV-TK phosphorylates the prodrug ganciclovir and generates nucleoside analogs that induce DNA chain termination and cell death in actively dividing cells. Tumor cells transduced with HSV-TK acquire sensitivity to ganciclovir, a clinically proven agent originally designed for treatment of viral infections. Moolten, F. L. and Wells, J. M., *J. Natl. Cancer Inst.* 82:297–300 (1990); Ezzeddine, Z. D., et al., *New Biol.* 3:608–614 (1991).

In a second example, the bacterial gene cytosine deaminase (CD) is a prodrug/enzyme activation system that has been shown to sensitize tumor cells to the antifungal agent 5-fluorocytosine as a result of its transformation to 5-flurouracil, a known cancer chemotherapeutic agent (Mullen, C. A., et al., *Proc. Natl. Acad. Sci. USA* 89: 33–37 (1992); Huber, B. E., et al., *Cancer Res.* 53:4619–4626 (1993); Mullen, C. A., et al., *Cancer Res.* 54:1503–1506 (1994)).

Recent studies using these drug susceptibility genes have yielded promising results. See, e.g., Caruso, M., et al., *Proc. Nat. Acad. Sci. USA* 90:7024–7028 (1993); Oldfield, E., et al., *Hum. Gene Ther.* 4: 39 (1993); Culver, K, *Clin. Chem* 40: 510 (1994); O'Malley, Jr., B. W., et al., *Cancer Res.* 56:1737–1741 (1996); Rainov, N. G., et al., *Cancer Gene Therapy* 3:99–106 (1996).

Several other prodrug-activating enzyme systems have also been investigated (T. A. Connors, *Gene Ther.* 2:702–709 (1995)). These include the bacterial enzyme carboxypeptidase G2, which does not have a mammalian homolog, and can be used to activate certain synthetic mustard prodrugs by cleavage of a glutamic acid moiety to release an active, cytotoxic mustard metabolite (Marais, R., et al., *Cancer Res.* 56: 4735–4742 (1996)), and *E. coli* nitro reductase, which activates the prodrug CB 1954 and related mustard prodrug analogs (Drabek, D., et al., *Gene Ther.* 4:93–100 (1997); Green, N. K., et al., *Cancer Gene Ther.* 4:229–238 (1997)), some of which may be superior to CB11954 (Friedlos, F. et al., *J Med Chem* 40:1270–1275 (1997)). The principle underlying these approaches to prodrug activation gene therapy is that transduction of a tumor cell population with the foreign gene confers upon it a unique prodrug activation capacity, and hence a chemosensitivity which is absent from host cells that do not express the gene.

More recently, a drug activation/gene therapy strategy has been developed based on a cytochrome P450 gene ("CYP" or "P450") in combination with a cancer chemotherapeutic agent that is activated through a P450-catalyzed monoxygenase reaction (Chen, L. and Waxman, D. J., *Cancer Research* 55:581–589 (1995); Wei, M. X., el al., Hum. Gene Ther. 5:969–978 (1994); U.S. Pat. No. 5,688,773, issued Nov. 18, 1997). Unlike the prodrug activation strategies mentioned above, the P450-based drug activation strategy utilizes a mammalian drug activation gene (rather than a bacterially or virally derived gene), and also utilizes established chemotherapeutic drugs widely used in cancer therapy.

Many anti-cancer drugs are known to be oxygenated by cytochrome P450 enzymes to yield metabolites that are cytotoxic or cytostatic toward tumor cells. These include several commonly used cancer chemotherapeutic drugs, such as cyclophosphamide (CPA), its isomer ifosfamide (IFA), dacarbazine, procarbazine, thio-TEPA, etoposide, 2-aminoanthracene, 4-ipomeanol, and tamoxifen (LeBlanc, G. A. and Waxman, D. J., *Drug Metab. Rev.* 20:395–439 (1989); Ng, S. F. and Waxman D. J., *Intl. J. Oncology* 2:731–738 (1993); Goeptar, A. R., et al., *Cancer Res.* 54:2411–2418 (1994); van Maanen, J. M., et al., *Cancer Res.* 47:4658–4662 (1987); Dehal, S. S., et al., *Cancer Res.* 57:3402–3406 (1997); Rainov, N. G., et al., *Human Gene Therapy* 9:1261–1273 (1998)).

In one example of this approach, tumor cells were rendered highly sensitive to CPA or IFA by transduction of CYP2B1, which encodes a liver P450 enzyme that exhibits a high rate of CPA and IFA activation (Clarke, L. and Waxman, D. J., *Cancer Res.* 49:2344–2350 (1989); Weber, G. F. and Waxman, D. J., *Biochem. Pharmacol.* 45:1685–1694 (1993)). This enhanced chemosensitivity has been demonstrated both in vitro and in studies using a subcutaneous rodent solid tumor model and human breast tumor grown in nude mice in vivo, and is strikingly effective in spite of the presence of a substantial liver-associated capacity for drug activation in these animals (Chen, L., et al., *Cancer Res.* 55:581–589 (1995); Chen, L., et al., *Cancer Res.* 56:1331–1340 (1996)). This P450-based approach also shows significant utility for gene therapy applications in the treatment of brain tumors (Wei, M. X., et al., *Human Gene Ther.* 5:969–978 (1994); Manome, Y., et al., *Gene Therapy* 3:513–520 (1996); Chase, M., et al., *Nature Biotechnol.* 16:444–448 (1998)).

In addition to transgenes comprising prodrug-activating or "suicide" genes, other types of anticancer transgenes have also been studied, including, cytokine genes (to enhance immune defense against the tumor) (Blankenstein, T., et al., *J. Exp. Med.* 173:1047–1052 (1991); Colombo, M. P., et al., *Cancer Metastasis Rev.* 16:421–432 (1997); Colombo, M. P., et al., *Immunol. Today* 15:48–51 (1994)) as well as other tumor toxic genes, such as diptheria toxin (Coll-Fresno, P. M., et al., *Oncogene* 14:243–247 (1997)), pseudomonas toxin, anti-angiogenesis genes, tumor vaccination genes, tumor suppressor genes, radiosensitivity genes, antisense RNA, and ribozymes (Zaia, J. A., et al., *Ann. N.Y. Acad. Sci.* 660:95–106 (1992)).

While both the virus-based and the gene-based approaches have provided evidence of significant therapeutic effects in animal models of tumors, each method suffers from inherent limitations. Although the viral-based approach theoretically provides the potential for extensive replication of the virus with spread in the tumor mass, its effects are limited by the efficiency of viral infection; the requirement of a helper virus or producer cell line for some viral vectors; tumor cell heterogeneity (Sidranski et al., 355: 846–847 (1992); Bigner et al., *J. Neuropathol. Exp. Neurol.* 40: 201–229 (1981)) for the cellular factor(s) complementing viral mutant growth for other viral vectors; and antiviral immune responses.

In the gene-based approaches tested thus far, the efficiency of transduction of cells within a tumor mass is limited by the defective nature of the vector. In fact, the majority of positively transduced cells occurs within a few cell layers from the site of vector inoculation (Nilaver et al. *Proc. Natl. Acad. Sci. USA* 21: 9829–9833 (1995); Muldoon et al., *Am. J. Pathol.* 147: 1840–1851 (1995); Ram Z. et al., *J. Neurosurg.* 82, 343A (abst.)(1995)). Moreover, even for viral vector systems where a producer cell line is unnecessary, or not killed by the suicide gene/drug combination, viral replication may be inhibited by the drug used. Furthermore, where the suicide-gene/drug combination is TK/GCV, the ability of the drug to kill tumor cells is limited by the stage of the cell cycle of the cells as GCV targets only cells in the process of DNA replication. It is thus unlikely that therapeutic gene delivery by these replication-defective vectors will affect tumor cells distant from the inoculation site, even in instances where the therapeutic gene produces a freely diffusible anticancer agent, such as cytokines or CPA metabolites.

A need therefore continues to exist for a safe and efficacious viral mutant that would provide a means to achieve selective virulence for tumors or other targeted cell populations, while retaining lack of toxicity for normal tissues.

SUMMARY OF THE INVENTION

Accordingly, the present invention overcomes the disadvantages of the prior art by providing a herpes viral mutant that can selectively target neoplastic cells for viral oncolysis by the transcriptional retargeting of $\gamma 34.5$'s action. The herpes viral mutant of the invention can also target other cell populations as well.

In a specific, but non-limiting, example, the inventors reintroduced the $\gamma 34.5$ gene into a RR/$\gamma 34.5$ double mutant strain (MGH1) under the transcriptional control of the cell-cycle regulated, cellular B-myb promoter. They demonstrated that this novel oncolytic virus (called "Myb34.5") remained as oncolytic as a single RR mutant virus that possessed a wild-type $\gamma 34.5$ gene, yet retained a favorable toxicity profile similar to that of a $\gamma 34.5$-deletion mutant. These findings thus show that the transcriptional retargeting of a viral gene responsible for preventing the shutoff of protein synthesis of infected cells provides an avenue for achieving selective oncolysis. Thus, the transcriptional retargeting of $\gamma 34.5$'s expression provides a means to achieve selective virulence for tumors, or other targeted cell populations.

In one embodiment of the invention, the herpes viral mutant comprises a deletion or inactivating mutation in both copies of the gene encoding $\gamma 34.5$, wherein at least one copy of the $\gamma 34.5$ gene is reintroduced under the transcriptional control of a cell-specific and/or tumor-specific promoter.

Of course, there may be more than one specific endogenous deletion or inactivating mutation of a herpes viral gene, in addition to the $\gamma 34.5$ gene. These include deletions in the gene that encodes ribonucleotide reductase (RR), or more particularly the large subunit of RR. Alternatively, the gene encoding RR encodes the small subunit (UL40). Any other herpes viral genes may also be deleted, such as, e.g., thymidine kinase (TK), uracil DNA glycosylase (UNG), or dUTPase. These viral genes are preferred as the mammalian homologues of these genes are often up-regulated in cells with elevated levels of E2F, such as neoplastic cells, and thus can complement the deleted viral enzyme, thereby promoting selective replication in those cells.

In another embodiment, the herpes mutant of the invention is also capable of delivering a transgene whose product could be cytotoxic to tumor cells. For example, the transgene could encode a product capable of activating or enhancing a chemotherapeutic agent (e.g., a suicide gene, such as HSV-TK, CD, or cytochrome P450). Alternatively, the transgene can be a cytokine gene to enhance tumor immunogenicity (e.g., tumor necrosis factor alpha (TNF-$\alpha$), interleukins (IL-2, IL-4), interferon-$\gamma$, granulocyte-macrophage colony stimulating factor (GM-CSF)), a tumor suppressor gene, or any other tumoricidal gene known to those skilled in the art, such as diptheria toxin, pseudomonas toxin, anti-angiogenesis genes, tumor vaccination genes, radiosensitivity genes, antisense RNA, or ribozymes. Thus, in this embodiment, the herpes mutant further comprises a transgene encoding a gene product capable of converting a chemotherapeutic agent to its cytotoxic form, a cytokine gene, or any other tumoricidal transgene. The transgene can be inserted in the original γ34.5 deletion or anywhere in the UL40 locus.

The invention provides a preferred embodiment of the foregoing herpes viral mutant where the transgene encodes a suicide gene that activates a chemotherapeutic agent. A particularly preferred example of such a suicide gene is mammalian cytochrome P450. More particularly, this cytochrome P450 may be P450 2B1, or alternatively P450 2B6, P450 2A6, P450 2C6, P450 2C8, P450 2C9, P450 2C11, or P450 3A4. P450 2B1 is particularly preferred. If such a suicide gene is present in the foregoing viral mutant, then the chemotherapeutic agent that would be activated is a member of the oxazosphorine class. Particularly, the agent would be cyclophosphamide, ifosfamide, N-methyl cyclophosphamide, methylchloropropylnitrosourea, polymeric cyclophosphamide, polymeric ifosfamide, polymeric N-methyl cyclophosphamide, or polymeric methylchloropropylnitrosourea.

The invention also provides an embodiment of the foregoing herpes viral mutants, wherein the herpes mutant is a herpes simplex virus, and more particularly, wherein the mutant is herpes simplex virus (HSV) type 1 or type 2. HSV-1 is particularly preferred.

In a very preferred embodiment of the invention, the herpes viral mutant is derived from HSV-1, and comprises: (a) a deletion or inactivating mutation in both copies of the gene encoding γ34.5; and (b) an insertion of at least one copy of said γ34.5 gene under transcriptional control of a cell-type specific and/or tumor specific promoter, such that said promoter drives expression of the γ34.5 gene.

In addition to γ34.5, deletions or mutations in other herpes viral genes may also be present in the herpes viral mutant of the invention. Deletions in herpes RR, TK, UNG, or dUTPase are exemplary herpes viral genes.

In this embodiment, the cell-specific promoter or tumor-specific promoter can be any one of the well-characterized regulatory elements controlling tumor-type and/or cell-type specific gene expression. For a review, see, Miller, N. and Whelan, J., *Hum. Gene Ther.* 8:803–815 (1997); Walther, W. and Stein, U., *J. Mol. Med.* 74:379–392 (1996); Schnierle, B. S. and Groner, B., *Gene Therapy* 3:1069–1073 (1996); Lan, K-H., et al., *Cancer Res.* 57:4279–4284 (1997); Clary, B. M., et al., *Cancer Gene Therapy* 7:565–574 (1998); Dachs, G. U., et al., *Oncol. Res.* 9:313–325 (1997)).

Representative examples of tumor-specific promoters include promoters that control or regulate the expression of proteins unique to, or overexpressed in, certain neoplastic cells, such as, e.g., DF3 (MUC1) (which is overexpressed in the majority of breast cancers)(Abe, M. and Kufe, D., *Proc. Natl. Acad. Sci. USA* 90:282–286 (1993); Manome, Y., et al., *Gene Ther.* 2:685, A051 (1995); Chen, L., et al., *J. Clin. Invest.* 96:2775–2782 (1995)); AFP (which is overexpressed in hepatoma)(Arbuthnot, P., et al., *Hepatology* 22:1788–1796 (1995); Ido, A., et al., *Cancer Res.* 55:3105–3109 (1995)); CEA (which is overexpressed in colon and lung cancers)(Thompson, J. A., et al., *J. Clin. Lab. Anal.* 5:344–366 (1991); Osaki, T., et al., *Cancer Res.* 54:5258–5261 (1994)); PSA (which is overexpressed in prostate cancers)(Lundwall, A., *Biochem. Biophys. Res. Commun.* 161:1151–1156 (1989)); tyrosinase (which is overexpressed in melanomas)(Vile, R. G. and Hart, I. R., *Cancer Res.* 53:962–967 (1993); Vile, R. G. and Hart, I. R., *Ann. Oncol* 5 (*Suppl.* 4):S59–S65 (1994); Hart, I. R., et al., *Curr. Opin. Oncol.* 6:221–225 (1994)); and c-erbB2 (which is overexpressed in breast, pancreatic, ovarian, or gastric carcinomas)(Hollywood, D, and Hurst, H., *EMBO J* 12:2369–2375 (1993)).

In a preferred embodiment, the tumor-specific promoter is B-myb. In a particularly preferred embodiment of the foregoing herpes viral mutant, the viral mutant is Myb34.5.

The herpes simplex virus type 1 vector, Myb34.5, was deposited and received on Jan. 28, 2003 by the American Type Culture Collection, 10801 University Boulevard, Manassas, Va. 20110-2209, and assigned Patent Deposit Designation PTA-4963. The ATCC deposit was made pursuant to the terms of the Budapest Treaty on the International Recognition of the Deposit of Microorganisms for the Purposes of Patent Procedure.

Exemplary cell-specific promoters include the following: endothelial nitric oxide synthase (eNOS) promoter expressed in endothelial cells (Guillot, P. V., et al., *J. Clin. Invest.* 103:799–805 (1999)); vascular endothelial growth factor (VEGF) receptor (flk1) promoter expressed in endothelial cells (Kappel et al. *Blood* 93: 4282–4292 (1999)); insulin promoter expressed in beta cells of the pancreas (Ray et al., *J. Surg. Res.* 84: 199–203 (1999)); promoter of gonadotropin-releasing hormone receptor gene expressed in cells of the hypothalamus (Albarracin et al., *Endocrinology* 140: 2415–2421 (1999)); matrix metalloproteinase 9 promoter expressed in osteoclasts and keratinocytes (Munant et al., *J. Biol. Chem.* 274: 5588–5596 (1999)); promoter of parathyroid hormone receptor expressed in bone cells (Amizuma et al., *J. Clin. Invest.* 103: 373–381 (1999)); and dopamine beta-hydroxylase promoter expressed in noradrenergic neurons (Yang et al., *J. Neurochem.* 71: 1813–1826 (1998)).

The present invention also provides a method for selectively killing neoplastic cells that overexpress a known tumor-specific protein using the herpes viral mutants described above, comprising: infecting said neoplastic cells with said herpes viral mutant, said viral mutant comprising: (a) a deletion or inactivating mutation in a gene encoding γ34.5; and (b) an insertion of at least one copy of said γ34.5 gene under the transcriptional control of the promoter of said tumor specific protein, such that said promoter drives expression of said γ34.5 gene; and selectively killing said neoplastic cells.

Representative examples of tumor-specific promoters include promoters that control or regulate the expression of proteins unique to, or overexpressed in, certain neoplastic cells, such as, e.g., DF3 (MUC 1) (which is overexpressed in the majority of breast cancers)(Abe, M. and Kufe, D., *Proc. Natl. Acad. Sci. USA* 90:282–286 (1993); Manome, Y., el al., *Gene Ther.* 2:685, A051 (1995); Chen, L., et al., *J. Clin. Invest.* 96:2775–2782 (1995)); AFP (which is overexpressed in hepatoma)(Arbuthnot, P., et al., *Hepatology* 22:1788–1796 (1995); Ido, A., et al., *Cancer Res.* 55:3105–3109 (1995)); CEA (which is overexpressed in colon and lung cancers)(Thompson, J. A., et al., *J. Clin. Lab. Anal.* 5:344–366 (1991); Osaki, T., et al., *Cancer Res.* 54:5258–5261 (1994)); PSA (which is overexpressed in prostate cancers)(Lundwall, A., *Biochem. Biophys. Res. Commun.* 161:1151–1156 (1989)); tyrosinase (which is overexpressed in melanomas)(Vile, R. G. and Hart, I. R., *Cancer Res.* 53:962–967 (1993); Vile, R. G. and Hart, I. R., *Ann. Oncol* 5 (*Suppl.* 4):S59–S65 (1994); Hart, I. R., et al., *Curr. Opin. Oncol.* 6:221–225 (1994)); and c-erbB2 (which is overexpressed in breast, pancreatic, ovarian, or gastric carcinomas)(Hollywood, D, and Hurst, H., *EMBO J* 12:2369–2375 (1993)).

Preferably, the tumor-specific promoter is B-myb. In a particularly preferred embodiment of this method, the viral mutant is Myb34.5.

In addition to γ34.5, deletions or mutations in other herpes viral genes may also be present in the herpes viral mutant used in the method of the invention. Deletions in herpes RR, TK, UNG, or dUTPase are exemplary herpes viral genes.

In addition, the invention provides the above method for selectively killing neoplastic cells, wherein said herpes viral mutant further comprises a transgene, wherein the transgene is a suicide gene, a cytokine gene, or any tumoricidal gene known to those skilled in the art. If the transgene is a suicide gene, then the method further comprises contacting the neoplastic cells with a chemotherapeutic agent capable of being activated by said suicide gene and selectively killing the neoplastic cells. The preferred suicide gene is cytochrome P450. P450 2B1 is particularly preferred. Alternatively, the cytochrome P450 encoded is P450 2B6, P450 2A6, P450 2C6, P450 2C8, P450 2C9, P450 2C11, or P450 3A4. In addition, the chemotherapeutic agent is preferably a member of the oxazosphorine class, particularly cyclophosphamide, ifosfamide, N-methyl cyclophosphamide, methylchloropropylnitrosourea, polymeric cyclophosphamide, polymeric ifosfamide, polymeric N-methyl cyclophosphamide, or polymeric methylchloropropylnitrosourea.

Another embodiment of the present invention is a method for selectively eliminating a target cell population that overexpresses a known cell-specific protein using the herpes viral mutants of the invention, comprising: infecting said target cells with said herpes viral mutant, said viral mutant comprising: (a) a deletion or inactivating mutation in a gene encoding γ34.5; and (b) an insertion of at least one copy of said γ34.5 gene under the transcriptional control of the promoter of said cell-specific protein, such that said promoter drives expression of said γ34.5 gene; and selectively eliminating a target cell population.

Exemplary cell-specific promoters include the following: endothelial nitric oxide synthase (eNOS) promoter expressed in endothelial cells (Guillot, P. V., et al., *J. Clin Invest.* 103:799–805 (1999)); vascular endothelial growth factor (VEGF) receptor (flk1) promoter expressed in endothelial cells (Kappel et al. *Blood* 93: 4282–4292 (1999)); insulin promoter expressed in beta cells of the pancreas (Ray et al., *J. Surg. Res.* 84: 199–203 (1999)); promoter of gonadotropin-releasing hormone receptor gene expressed in cells of the hypothalamus (Albarracin et al., *Endocrinology* 140:2415–2421 (1999)); matrix metalloproteinase 9 promoter expressed in osteoclasts and keratinocytes (Munant et al., *J. Biol. Chem.* 274: 5588–5596 (1999)); promoter of parathyroid hormone receptor expressed in bone cells (Amizuma et al., *J. Clin. Invest.* 103: 373–381 (1999)); and dopamine beta-hydroxylase promoter expressed in noradrenergic neurons (Yang et al., *J. Neurochem.* 71: 1813–1826 (1998)).

In addition to γ34.5, deletions or mutations in other herpes viral genes may also be present in the herpes viral mutant used in the method of the invention. Deletions in herpes RR, TK, UNG, or dUTPase are exemplary herpes viral genes.

Examplary applications of this embodiment include the following:

1) Treatment options to eliminate a noxious cell population: For example, in conditions where there is exuberant neovascularization of blood vessels, such as cerebral Moya—Moya disease, use of the flk1 receptor promoter to drive γ34.5 gene expression would allow for selective elimination of the blood vessels causing this disease. Another example is in conditions where there is extensive bone remodeling and elimination of bone, such as osteoporosis, the use of the promoter regions of the matrix metalloproteinase 9 or the parathyroid hormone receptor to drive expression of γ34.5 would eliminate bone osteoclasts from further remodeling of bone.

2) To study developmental processes: In order to study the effect of elimination of a cell population on developmental processes, one could use, for example, the dopamine-beta-hydroxylase promoter to eliminate the noradrenergic neurons and then study the effect on animal development.

Another embodiment of the invention is a pharmaceutical composition containing any of the foregoing viral mutants, wherein this composition may also contain one or more pharmaceutically acceptable excipients.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1A depicts schematic maps of the HSV strains F (wild-type), MGH1 (double RR(ICP6)/γ34.5 mutant), and Myb34.5. All strains contain the typical HSV genome with two unique segments, UL and US, each flanked by inverted repeat elements, ab and ca, respectively (McGeoch, D. J., et al., *J. Gen. Virol.* 72:3057–3075 (1991)). Depending on their localization in either unique or repeat segments, the HSV genes are present in one or two copies. The black box indicates the lacZ insertion into a BamHI site within ICP6 (Goldstein, D. J. & Weller, S. K., *J. Virol.* 62:2970–2977 (1988)), while Δ indicates the deletions within γ34.5 in MGH1 and Myb34.5 (Kramm, C. M., et al., *Hum. Gene Ther.* 8:2057–2068 (1997)). The hatched bar indicates recombination of the B-myb promoter-γ34.5 construct into the ICP6 locus.

FIG. 1B depicts characterization of the HSV mutant Myb34.5 by Southern blot analysis. Hybridization of XhoI digested viral DNA to a full-length probe for ICP6 reveals the expected 9.0 kB fragment sizes for the ICP6 gene with a full length lacZ insertion in MHG1 (lane 2) and MybRevt (lane 4). In Myb 34.5 (lane 3), there is replacement by the B-myb promoter/γ34.5 cassette and further deletion of ICP6 to give a 6.7 kB band. DNA from wild-type F strain is in lane 1.

FIG. 1C depicts hybridization with a lacZ probe, and reveals fragments with MGH1 (lane 2) and MybRevt (lane 4), with no hybridization to Myb34.5 (lane 3).

FIG. 1D depicts a BstEII-Bbs fragment of γ34.5, internal to the deleted regions of R3616 and MGH1, which reveals a 5.3 kB fragment in BamHI digested Myb34.5 (DNA (lane 3), and several bands in F (lane 1), but fails to hybridize to either MGH1 (lane 2) or MybRevt (lane 4).

In FIG. 4A, differences in tumor volumes were significant at the 12, 18, and 33-day time points (p<0.05, one-way repeated measures of variance). In FIG. 4B, differences in tumor volumes were significant at the 18, 27, and 34-day time points (p<0.05, one-way repeated measures of variance). For day 34 alone, as shown in Table 4, p<0.005.

FIG. 6A: Autoradiographs of purified phosphorylated eIF-2α reacted with S10 fractions from mock-infected cells (lanes 1–3), F-strain-infected cells (lanes 4–6), Myb34.5-infected cells (lanes 7–9), and MGH1-infected cells (lanes 10–12). S10 fractions were collected from HT29 colon carcinoma cells (upper panel) and primary cultures of normal human hepatocytes (H.H.)(lower panel). The reaction time measured in seconds is shown at the top of each panel. FIG. 6B: eIF-2α dephosphorylation rates of HT29 colon carcinoma cells (a) and human hepatocytes (b) were determined by quantification of the bands in (A) with a densitometer.

FIG. 7A: Single step viral replication assays were performed using F strain, hrR3, Myb34.5, R3616 and MGH1 in HT29 colon carcinoma cells and the human hepatocytes (H. Hepatocytes). FIG. 7B: Single step viral replication assays were similarly performed in MC26 mouse colon carcinoma cells (MC26) and the mouse hepatocytes (M. Hepatocytes). Viruses were recovered from cells infected using an moi=2 for each virus and titered on confluent layers of Vero cells. Ribonucleotide reductase (RR) and β-actin expression were measured by Western blot analysis.

FIG. 9A: Diffuse liver metastases were established by an intrasplenic injection of $1 \times 10^5$ MC26 cells into the spleens of BALB/c mice. Three days later, 5×10¹ pfu of either heat-inactivated Myb34.5 (upper row), Myb34.5 (middle row), or F strain (lower row) were injected into spleen. Fourteen days after tumor implantation, mice were sacrificed and livers and spleens were analyzed. FIG. 9B: Graph depicting survival rate of mice with liver metastases treated with Myb34.5. Diffuse liver metastases were established by an intrasplenic injection of $1 \times 10^5$ MC26 cells into the spleens of BALB/c mice. Three days later, $5 \times 10^7$ pfu of either heat-inactivated Myb34.5, Myb34.5, or F strain were injected into spleen. p<0.05 for F strain versus heat-inactivated Myb34.5 and p<0.01 for Myb34.5 versus control by log-rank test. The difference in survival between mice treated with F strain and Myb34.5 is not statistically significant.

FIG. 11A: Mice injected subcutaneously with F strain or Myb34.5 were sacrificed 7 days later to harvest tissues for DNA extraction. PCR amplification of the HSV-1 DNA polymerase gene was performed on the extracted DNA, and bands were resolved on a 2% agarose gel stained with ethidium bromide. 1 Kb marker is shown in lane M, with the expected 220 bp bands indicated. A negative control reaction without template is shown in lane N, and a positive control reaction using HSV-1 genomic DNA as template is shown in lane P. FIG. 11B: Seven days following intrasplenic inoculation of either MC26 colon carcinoma cells (lanes 1, 2, and 3) or HBSS media (lanes 4, 5, and 6) mice were treated with a single intrasplenic injection of $1 \times 10^7$ pfu Myb34.5. Mice were sacrificed 10 days after Myb34.5 treatment to harvest their livers for DNA extraction. PCR amplification of the HSV-1 DNA polymerase gene was performed and amplification products were resolved on agarose gels and stained with ethidium bromide.

Figure 1A:
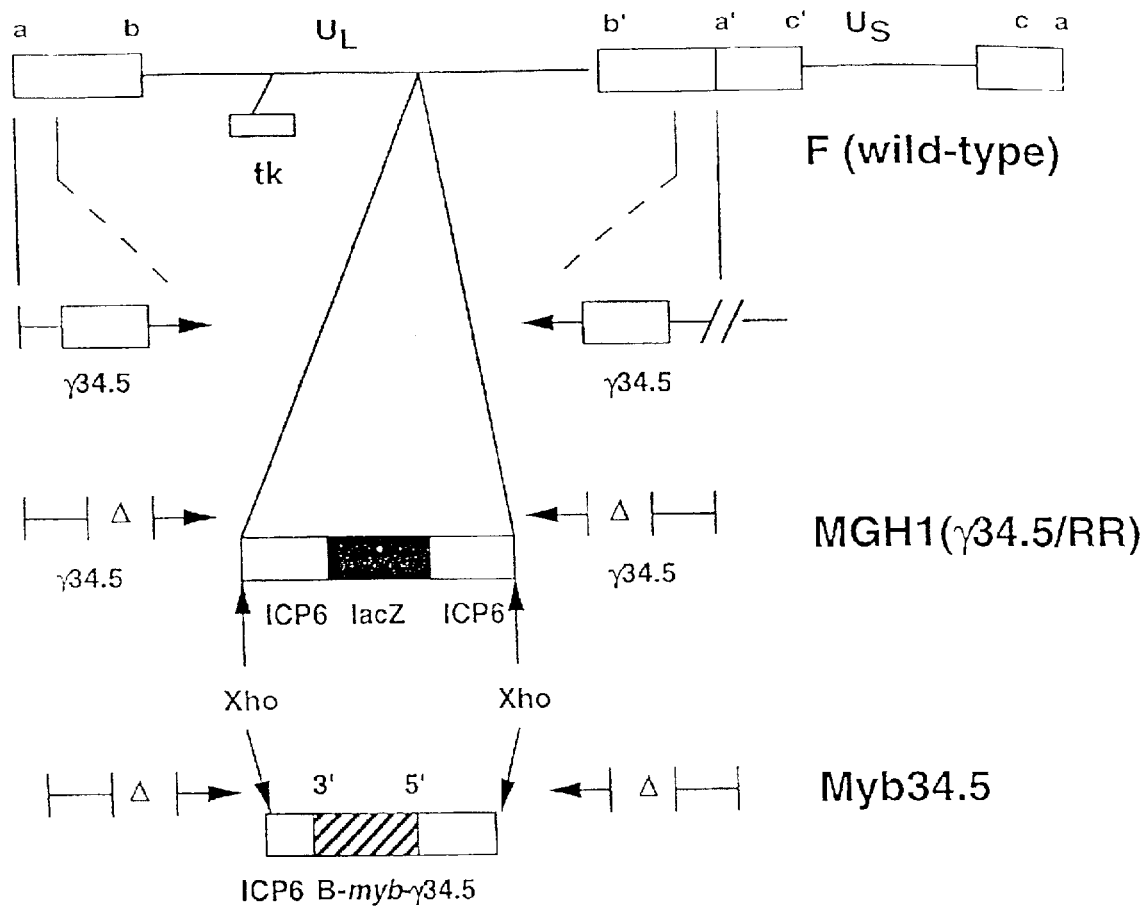
FIGS. 1A–1D.

Mice were vaccinated with either KOS (middle row) or HBSS (lower row) 25 days prior to intrasplenic inoculation of MC26 cells. Mice were then treated with $5 \times 10^7$ pfu Myb34.5 three days following tumor implantation and sacrificed 14 days following tumor implantation. To serve as a control group, mice vaccinated with Myb34.5 were treated with heat-inactivated Myb34.5 (upper row).

DETAILED DESCRIPTION OF THE PREFERRED EMBODIMENTS

The present invention relates to the selective killing of neoplastic cells by viral mediated oncolysis alone or the combination of viral mediated oncolysis and suicide gene therapy. The invention provides for a herpes viral mutant, a method of selectively killing neoplastic cells using this herpes viral mutant, and a pharmaceutical composition containing the viral mutant. The invention also provides a method for selectively eliminating target cell populations using the herpes viral mutant of the invention.

More specifically, the invention provides for a herpes viral mutant, wherein the mutant is genetically engineered to have (a) a deletion or inactivating mutation in both copies of the gene encoding γ34.5; and (b) an insertion of at least one copy of said γ34.5 gene under the transcriptional control of a tumor-specific or cell-type specific promoter, such that said promoter drives expression of the γ34.5 gene. The herpes mutant may also contain one or more additional deletions or mutations in other herpes viral genes, such as, e.g., RR, TK, UNG, and dUTPase. The herpes viral mutant can also deliver a transgene encoding a product that activates a chemotherapeutic agent, a cytokine gene, or any other tumoricidal gene.

Design of the Herpes Viral Mutant

The herpes viral mutants of the invention may be derived from several different types of herpes viruses. Herpes viruses that may be used to derive the viral mutants of the invention include herpes simplex virus (HSV), cytomegalovirus, Epstein-Barr virus, varicella zoster virus, and pseudorabies virus.

Herpes simplex viruses are of particular interest. By "herpes simplex virus" is intended any member of the subfamily herpesviridae alpha containing a deletion or inactivating mutation as described above. A preferred embodiment of the invention employs HSV-1 or HSV-2 to create the herpes viral mutant, with HSV-1 being the most preferred.

HSV-1 is a human neurotropic virus that is capable of infecting virtually all vertebrate cells. Natural infections follow either a lytic, replicative cycle or establish latency, usually in peripheral ganglia, where the DNA is maintained indefinitely in an episomal state. HSV-1 contains a double-stranded, linear DNA genome, 153 kilobases in length, which has been completely sequenced by McGeoch (McGeoch et al., *J. Gen. Virol.* 69: 1531 (1988); McGeoch et al., *Nucleic Acids Res* 14: 1727 (1986); McGeoch et al., *J. Mol. Biol.* 181: 1 (1985); Perry and McGeoch, *J. Gen. Virol.* 69:2831 (1988)). DNA replication and virion assembly occurs in the nucleus of infected cells. Late in infection, concatemeric viral DNA is cleaved into genome length molecules which are packaged into virions. In the CNS, herpes simplex virus spreads transneuronally followed by intraaxonal transport to the nucleus, either retrograde or anterograde, where replication occurs.

The Herpes Gamma (γ) 34.5 Gene

Published results have demonstrated that at least one function of the herpes γ34.5 gene (which is alternatively known as the $γ_1$34.5 gene) is to preclude the host cell's response to viral infection, namely the triggering of host protein synthesis shutoff in an apoptotic-like response (Chou, J., et al., *Science* 250:1262–1266 (1990); Chou, J. and Roizman, B., *Proc. Natl. Acad. Sci. USA* 89:3266–3270 (1992); Chou, J., et al., *Proc. Natl. Acad. Sci. USA* 92:10516–10520 (1995)). A similar function is widespread among pathogenic viruses (Cosentino, G. P., et al., *Proc. Natl. Acad. Sci. USA* 92:9445–9449 (1995); Gale, M., Jr., et al., *Mol. Cell Biol.* 18:5208–5218 (1998); Katze, M. G., et al., *Trends Microbiol.* 3:75–78 (1995); Sharp, T. V., et al., *Nuc. Acids Res.* 21:4483–4490 (1993)).

While γ34.5 is nonessential for viral growth in culture in Vero cells, it enables the virus to spread in the central nervous system (CNS) of mice, and maps to a region of the HSV genome previously implicated in CNS replication (Markovitz, N. S., et al., *J. Virol.* 71:5560–5569 (1997); Centifanto-Fitzgerald, Y. M., et al., *J. Esp. Med* 155:475–489 (1982)). This may be due to the fact that the γ34.5-encoded protein inhibits the double-stranded RNA-dependent kinase (PKR). On exposure to double stranded RNA molecules, as seen commonly with viral infection, PKR phosphorylates the alpha subunit of elongation initiation factor eIF-2, resulting in inhibition of protein synthesis (Chou, J., et al., *Science* 250:1262–1266 (1990); Chou, J. and Roizman, B., *Proc. Natl. Acad. Sci USA* 89:3266–3270 (1992); Chou, J., et al., J. Virol. 68:8304–8311 (1994)). Infection of cells of neuronal origin with mutants incapable of expressing γ34.5 results in shut-off of cellular protein synthesis, with the resultant limitation of viral production.

In summary, in the presence of γ34.5, HSV will prevent apoptosis, thus allowing for production of progeny viruses. In its absence, the cell dies and the infecting HSV cannot generate progeny viruses. Thus, HSV infection/propagation throughout an organ is eliminated.

The tumor- or cell type-specific promoter/γ34.5 approach of the invention, thus allows for production of virus in cells that can use that promoter, but cells that cannot turn on the promoter will not propagate infection.

The herpes viral mutant of the invention comprises a deletion or inactivating mutation in both copies of the γ34.5 gene, wherein at least one copy of the γ34.5 gene is reintroduced under the control of a cell-specific or tumor-specific promoter.

As used herein, the term "deletion" is intended to mean the elimination of nucleic acids from a gene, such as the γ34.5 gene.

As used herein, the term "inactivating mutation" is intended to broadly mean a mutation or alteration to a gene wherein the expression of that gene is significantly decreased, or wherein the gene product is rendered nonfunctional, or its ability to function is significantly decreased.

The term "gene" encompasses both the regions coding the gene product as well as regulatory regions for that gene, such as a promoter or enhancer, unless otherwise indicated.

Ways to achieve such alterations include: (a) any method to disrupt the expression of the product of the gene or (b) any method to render the expressed gene nonfunctional. Numerous methods to disrupt the expression of a gene are known, including the alterations of the coding region of the gene, or its promoter sequence, by insertions, deletions and/or base changes. (See, Roizman, B. and Jenkins, F. J., *Science* 229: 1208–1214 (1985)).

The Cell-Specific and/or Tumor Specific Promoter

In the herpes viral mutant of the invention, a cell-specific and/or tumor-specific promoter is used to drive expression of γ34.5. The promoter can be any one of the well-characterized regulatory elements controlling tumor-type and/or cell-type specific gene expression. For a review, see, Miller, N. and Whelan, J., *Hum. Gene Ther.* 8:803–815 (1997); Walther, W. and Stein, U., *J. Mol. Med.* 74:379–392 (1996); Schnierle, B. S. and Groner, B., *Gene Therapy* 3:1069–1073 (1996); Lan, K-H., et al., *Cancer Res.* 57:4279–4284 (1997); Clary, B. M., et al., *Cancer Gene Therapy* 7:565–574 (1998); Dachs, G. U., et al., *Oncol. Res.* 9:313–325 (1997)).

By "promoter" is intended to mean the DNA region, usually upstream to the coding sequence of a gene or operon, which binds RNA polymerase and directs the enzyme to the correct transcriptional start site.

By "cell-specific promoter" is intended a promoter that directs expression in particular cell types. One skilled in the art would know that a "tumor-specific" promoter can also be considered a "cell-specific" promoter (i.e., it is specific for tumor cells). However, for clarity, a "cell-specific promoter", as used herein, is intended to exclude tumor-specific promoters, unless otherwise indicated. Exemplary cell-specific promoters include the following: endothelial nitric oxide synthase (eNOS) promoter expressed in endothelial cells (Guillot, P. V., et al., *J. Clin Invest.* 103:799–805 (1999)); vascular endothelial growth factor (VEGF) receptor (flk1) promoter expressed in endothelial cells (Kappel et al. *Blood* 93: 4282–4292 (1999)); insulin promoter expressed in beta cells of the pancreas (Ray et al., *J. Surg. Res.* 84: 199–203 (1999)); promoter of gonadotropin-releasing hormone receptor gene expressed in cells of the hypothalamus (Albarracin et al., *Endocrinology* 140: 2415–2421 (1999)); matrix metalloproteinase 9 promoter, expressed in osteoclasts and keratinocytes (Munant et al., *J. Biol. Chem.* 274: 5588–5596 (1999)); promoter of parathyroid hormone receptor expressed in bone cells (Amizuma et al., *J. Clin. Invest.* 103: 373–381 (1999)); and dopamine beta-hydroxylase promoter expressed in noradrenergic neurons (Yang et al., *J. Neurochem.* 71: 1813–1826 (1998)).

Cell-cycle regulated promoters are also a type of cell-specific promoter. Other cell-specific promoters will be known to those skilled in the art.

Applications of this vector embodiment include the elimination of select noxious cell populations in an organ, as well as animal models to study the elimination of select populations in an organ during development. Exemplary applications of this embodiment include the following:

1) Treatment options to eliminate a noxious cell population: In one example, in conditions where there is exuberant neovascularization of blood vessels, such as cerebral Moya—Moya disease, the use of the flk1 receptor promoter to drive γ34.5 gene expression would allow for selective elimination of the blood vessels causing this disease.

In another example, in conditions where there is extensive bone remodeling and elimination of bone, such as osteoporosis, the use of the promoter regions of matrix metalloproteinase 9 or the parathyroid hormone receptor to drive expression of γ34.5 would eliminate bone osteoclasts from further remodeling of bone.

2) To study the effect of elimination of select populations in an organ during development: For example, in order to study the effect of elimination of a cell population on developmental processes, one could use, for example, the dopamine-beta-hydroxylase promoter to eliminate the noradrenergic neurons and then study the effect on animal development.

By "tumor-specific promoter" is intended a promoter of a protein that is induced selectively or expressed at a higher level in the target tumor cell than in a normal cell. The tumor targeting specificity for the herpes viral mutant of the invention is achieved by the use of tumor-specific promoters to selectively activate expression of the transduced gene in the tumor cell at either the primary tumor site or its metastases (Miller, N. and Whelan, J., *Hum. Gene Ther.* 8:803–815 (1997); Walther, W. and Stein, U., *J. Mol. Med.* 74:379–392 (1996); Schnierle, B. S. and Groner, B., *Gene Therapy* 3:1069–1073 (1996); Lan, K-H., et al., *Cancer Res.* 57:4279–4284 (1997); Dachs, G. U., et al., *Oncol. Res.* 9:313–325 (1997)).

Examples of tumor-specific promoters include promoters that have been derived from genes that encode tyrosinase (allowing for targeting to melanoma) (Vile, R. G. and Hart, I. R., *Cancer Res.* 53:962–967 (1993); Vile, R. G. and Hart, I. R., *Ann. Oncol* 5 (*Suppl.* 4):S59–S65 (1994); Hart, I. R., et al., *Curr. Opin. Oncol.* 6:221–225 (1994)); c-erbB-2 oncogene (targeting to breast, pancreatic, gastric, and ovarian cancers) (Hollywood, D., and Hurst, H., *EMBO J* 12:2369–2375 (1993)); carcinoembryonic antigen (CEA) (targeting to lung and gastrointestinal malignancies, including colon, pancreatic, and gastric cancer) (Thompson, J. A., et al., *J. Clin. Lab. Anal.* 5:344–366 (1991); Osaki, T., et al., *Cancer Res.* 54:5258–5261 (1994)); DF3/MUC1 (targeting to breast cancer) (Abe, M. and Kufe, D., *Proc. Natl. Acad. Sci. USA* 90:282–286 (1993); Manome, Y., et al., *Gene Ther.* 2:685, A051 (1995); Chen, L., et al., *J. Clin. Invest.* 96:2775–2782 (1995)); prostate specific antigen(PSA) (targeting to prostate cancer) (Lundwall, A., *Biochem. Biophys. Res. Commun.* 161:1151–1156 (1989)); and alpha-fetoprotein (AFP)(targeting to hepatocellular carcinoma) (Arbuthnot, P., et al., *Hepatology* 22:1788–1796 (1995); Ido, A., et al., *Cancer Res.* 55:3105–3109 (1995)).

The use of synthetic gene regulation systems, which allow for transcriptional control, as well as other forms of regulated expression may also be used (Miller, N. and Whelan, J., *Hum. Gene Ther.* 8:803–815 (1997); Vile, R. G., *Semin. Cancer Biol.* 5:429–436 (1994); Hwang, J. J., et al., *J. Virol.* 70:8138–8141 (1996); Massie, B., et al., *J. Virol.* 72:2289–2296 (1998)) to drive expression of the γ34.5 gene.

Tumor cells are also known to overexpress particular oncogenes, so that cells with upregulated gene expression can be targeted using the promoter elements of such genes. B-myb, C-myb, c-myc, c-kit, and the c-erbB2 oncogene are some representative examples of these types. The B-myb promoter (see, Lyon, J., et al., *Crit. Rev. Oncogenesis* 5:373–388 (1994) contains a consensus E2F binding site, is strictly regulated in cycling cells, and is in fact repressed in $G_0$ (Lam, E. W. and Watson, R. J., *EMBO J.* 12:2705–2713 (1993); Lam, E. W., et al., *Gene* 160:277–281 (1995); Bennett, J. D., et al., *Oncogene* 13:1073–1082 (1996)). Accordingly, the B-myb promoter is a particularly preferred tumor-specific promoter.

Any cancer type having a well-characterized promoter would find use in the invention. Examples of such promoters can be found in Table 1 of Clary, B. M., et al., *Cancer Gene Therapy* 7:565–574 (1998); Table 1 of Spear, M. A., *Anticancer Research* 18:3223–3232 (1998); Table 2 of Walther, W. and Stein, U., *J. Mol. Med* 74:379–392 (1996); and Dachs, G. U., et al., *Oncol. Res.* 9:313–325 (1997)).

Most if not all of the gene sequences of the tumor-specific promoters described above are available from the GenBank Sequence Database.

Other Mutations/Deletions in the Construct, in Addition to γ34.5

The viral mutants of the invention may also possess additional mutations in any viral gene(s), but most preferably in a gene required for replication, whose mammalian homologue is up-regulated by elevated levels of E2F.

For example, mammalian ribonucleotide reductase (mRR) is unregulated during the $G_1$ phase of the cell cycle and its transcription is regulated by "free" E2F (DeGregori et al., *Mol. Cell. Biol.* 15: 4215–4224 (1995); Lukas et al., *Mol. Cell. Biol.* 16: 1047–1057 (1996); Dynlacht et al., *Genes Dev.* 8: 1772–1786 (1994)). It has been hypothesized that RR⁻ viral mutants selectively replicate in neoplastic cells owing to the presence of the complementing mammalian ribonucleotide reductase (mRR)) in these cells (Goldstein and Weller, *J. Virol.* 62: 196–205 (1988)).

Elevation in the levels of free E2F causes increased expression of several mammalian genes whose viral homologues are required for replication of the virus. In addition to ribonucleotide reductase (RR), these genes include thymidine kinase (TK), uracyl DNA glycosylase (UNG), and uracyl-triphosphatase enzymes (dUTPase). Viruses containing a mutation in one or more of these genes would replicate selectively in cells with elevated levels of free E2F. Thus, the invention encompasses herpes viral mutants having a mutation in one or more of these genes, in addition to the mutation in γ34.5. In a preferred embodiment of the invention, the mutation is in a RR gene.

E2F (including E2F1, E2F2, E2F3, E2F4, E2F5) appears to be the primary mediator of the cell cycle-regulated transcriptional cascade that involves p16, cyclin D/cdk4, and pRB (DeGregori et al., *Mol. Cell. Biol.* 15: 4215–4224 (1995); Lukas et al., *Mol Cell. Biol* 16:1047–1057 (1996; Dynlacht et al., *Genes Dev.* 8: 1772–1786 (1994)). Thus, defects in a gene involved in this cascade can lead to increased levels of E2F and thereby increased levels of mammalian RR, TK, UNG and dUTPase. For example, cells with defects in the expression of p16, p21 and/or p27 may have increased levels of cyclin D, cyclin D kinase 4 (Cdk4) and/or cyclin D kinase 6 (Cdk6) which may in turn lead to increased phosphorylation of pRB thereby liberating E2F. In addition, cells with defects in the expression of pRB, p107 and or p130, DP1, DP2, and/or DP3 may also lead to increased liberation of E2F.

The majority of tumors possess an inactivation of a gene encoding a component of this cascade (Ueki et al., *Cancer Res.* 56: 150–153 (1996)), thus liberating E2F and allowing for transcription of mammalian RR, TK, UNG, and dUTPase. Moreover, alterations in other tumor suppressor genes or oncogenes may also lead to increased levels of free E2F, and thereby increased levels of mammalian RR, TK, UNG and dUTPase. Therefore, RR⁻, TK⁻, UNG⁻ and dUTPase⁻ viral mutants may effectively target a large percentage of tumor cells, particularly if they possess a defect in the p16/cyclin D/pRB pathway that leads to an increase in "free" E2F.

Furthermore, tumor cells from many different origins (e.g., lung, breast, prostate, brain, liver, pancreas, skin, etc.) possess alterations in the pathways described above leading to elevated levels of RR, TK, UNG and dUTPase, and thus are targets for the viral mutant of the invention. For example, the glioma tumor cell lines (rat 9L, human U87, and human T98 cells) possess inactivating mutations of p16 (Van Meir et al., *Cancer Res.* 54: 649–652 (1994)), as well as elevated levels of mRR. These cells were thus able to complement the replication of the HSV-1 derived viral mutant rRp450 to levels close to that of the wild-type KOS strain, while neurons with no detectable level of mRR (and with a normal p16 pathway) did not.

By "ribonucleotide reductase gene" is intended a nucleic acid that encodes any subunit or part of the enzyme, ribonucleotide reductase, such that when this nucleic acid is expressed in a cell, this part or subunit is produced, whether functional or nonfunctional. Ribonucleotide reductase (RR) is a key enzyme in the de novo synthesis of DNA precursors, catalyzing the reduction of ribonucleotides to deoxyribonucleotides. HSV-1 encodes its own RR (UL39 and UL40 genes), which is composed of two non-identical subunits (Duita, *J. Gen. Virol.* 64: 513 (1983)). The large subunit (140k molecular weight), designated ICP6, is tightly associated with the small subunit (38k molecular weight). Herpes simplex virus RR has been found to be required for efficient viral growth in non-dividing cells but not in many dividing cells (Goldstein and Weller, J. Virol. 62: 196 (1988); Goldstein and Weller, Virol. 166: 41 (1988); Jacobson et al., Virol. 173: 276 (1989)). Mutations in the small subunit of RR also lead to loss of RR activity and neuropathogenicity (Cameron et al., J. Gen. Virol. 69: 2607 (1988)), however, particularly preferred are mutations in the large subunit.

The promoter region of ribonucleotide reductase ICP6 has been mapped to the 5' upstream sequences of the ICP6 structural gene (Goldstein and Weller, J. Virol. 62: 196 (1988); Sze and Herman, *Virus Res.* 26: 141 (1992)). The transcription start site for the small subunit of RR, namely UL40, falls within the coding region of ICP6 (McLauchlan and Clements, *J. Gen. Virol.* 64:997 (1983); McGeoch et al., *J. Gen. Virol.* 69: 1531 (1988)).

Viral mutants derived from HSV-2 based on the viral mutants illustrated herein using the HSV-1 genome are encompassed by the present invention. HSV-2 contains both RR subunits; moreover, HSV-2 ICP10 is analogous to HSV-1 ICP6. Nikas et al. *Proteins* 1: 376 (1986); McLaughlan and Clements, *EMBO J.* 2: 1953 (1983); Swain and Halloway, *J. Virol.* 57: 802 (1986).

One difference between ribonucleotide reductase deficient (RR⁻) and other herpes simplex virus mutants is hypersensitivity to acyclovir and ganciclovir. Because TK⁻ HSV-1 mutants known in the art are resistant to these anti-viral agents, such mutants could be difficult to eliminate in the event of systemic infection or encephalitis. In contrast, in the event of viral encephalitis, TK⁺ viral mutants, such as RR⁻ HSV mutants, are responsive to antiviral therapy.

In addition, RR⁻ HSV mutants are compromised in their ability to produce infections and synthesize viral DNA at 39.5° C. in vitro (Goldstein and Weller, Virology 166:41 (1988)). Therefore, these mutants are attenuated for neurovirulence and less likely to propagate in the event of a fever in the infected host. Such characteristics are important to a therapeutic vector that must be of attenuated neurovirulence and amenable to antiviral therapy in the event of viral encephalitis.

The temperature sensitivity of RR⁻ viral mutants demonstrates another advantage of the viral mutant of the invention. In patients treated with a viral mutant, it is possible that a number of host factors (fever, antiviral immune responses) would inhibit propagation of the viral mutant. In these instances, it would be expected that treatment with a chemotherapeutic agent and activation by the transgene (for those cells infected by the viral mutant) would provide a supplemental anti-cancer treatment.

As used herein, "mutation" refers to any alteration to a gene wherein the expression of that gene is significantly decreased, or wherein the gene product is rendered nonfunctional, or its ability to function is significantly decreased. The term "gene" encompasses both the regions coding the gene product as well as regulatory regions for that gene, such as a promoter or enhancer. Such alterations render the product of the gene non-functional or reduce the expression of the gene such that the viral mutant has the properties of the instant invention. Moreover, the invention encompasses mutants with one or more mutation(s) in one or more gene(s) of interest. Thus, by "a" is intended one or more.

Ways to achieve such alterations include: (a) any method to disrupt the expression of the product of the gene; or (b) any method to render the expressed protein nonfunctional. Numerous methods known to disrupt the expression of a gene are known, including the alterations of the coding region of the gene, or its promoter sequence, by insertions, deletions and/or base changes. (See, Roizman, B. and Jenkins, F. J., *Science* 229: 1208–1214 (1985)). A deletion is a preferred mutation.

Methods for the construction of engineered viruses and for the genetic manipulation of DNA sequences are known in the art. Generally, these include Ausubel et al., Chapter 16 in *Current Protocols in Molecular Biology* (John Wiley and Sons, Inc.); Paoletti et al., U.S. Pat. No. 4,603,112 (July 1986). Virological considerations also are reviewed in Coen, in *Virology*, 1990 ($2^{nd}$ ed.) Raven Press, pages 123–150.

The construction of HSV-1 mutants is described, for example, in Martuza et al., U.S. Pat. No. 5,585,096 (December 1996); Roizman et al., U.S. Pat. No. 5,288,641 (February 1994); Roizman, B. and Jenkins, F. J., *Science* 229:1208–1214 (1985); Johnson et al., J. Virol. 66:2952 (1992); Gage, P. J., et al., *J. Virol.* 66:5509–5515 (1992); Goldstein and Weller, J. Virol. 62:196–205 (1988), Coen, D., Chapter 7, in Virology, 1990 ($2^{nd}$ ed.) Raven Press; Breakefield and DeLuca, *The New Biologist* 3:203 (1991); Leib and Olivo, *BioEssays* 15:547 (1993); Glorioso et al., *Seminars in Virology* 3:265 (1992); Chou, J. and Roizman, B., *Proc. Natl. Acad. Sci. USA,* 89:3266–3270 (1992); Shih et al., in *Vaccines* 85, 1985, Cold Spring Harbor Press, pages 177–180; Kramm, C. M., et al., *Hum. Gene Ther.* 8:2057–2068 (1997)); Glorioso, J. C., et al., *Annu. Rev. Microbiol.* 49:675–710 (1995); Mocarski et al., *Cell* 22:243 (1980)).

Genetic alterations of the viral genome can be determined by standard methods such as Southern blot hybridization of restriction endonuclease digested viral DNA, sequencing of mutated regions of viral DNA, detection of new (or lost) restriction endonuclease sites, enzymatic assay for ribonucleotide reductase activity (Huszar, D. and Bacchetti, S., *J. Virol.* 37:580–598 (1981)). For cells lacking the mammalian homologue of the mutated viral gene, e.g., RR, genetic alteration of the viral genome can be determined by (1) Western blot or ELISA analysis of infected cell proteins with antibodies the viral homologue that has been mutated, e.g., RR, or (2) Northern blot analysis of infected cells for transcription of the viral homologue that has been mutated, e.g., RR (Jacobson, J. G., et al., *Virology* 173:276–283 (1989)). A viral mutant that has been mutated in one or more genes can be isolated after mutagenesis or constructed via recombination between the viral genome and genetically-engineered sequences.

By "up-regulated" is intended that expression of the gene(s) encoding the gene product said to be up-regulated is greater than the basal level of expression of this product as found in non-neoplastic cells.

By "level of free E2F is elevated" is meant that the amount of unbound E2F available in a cell is greater than the amount typically found in non-neoplastic cells.

By "selectively killing neoplastic cells" is meant that the herpes viral mutant of the invention primarily targets neoplastic cells, rather than non-neoplastic cells.

By "neoplastic cells" is meant cells whose normal growth control mechanisms are disrupted (typically by accumulated genetic mutations), thereby providing potential for uncontrolled proliferation. Thus, "neoplastic cells" can include both dividing and non-dividing cells; also, "neoplastic cells" can include cells from primary tumor sites and/or metastatic sites. For purposes of the invention, neoplastic cells include cells of tumors, neoplasms, carcinomas, sarcomas, leukemias, lymphomas, and the like. Of particular interest are central nervous system (CNS) tumors, especially brain tumors. These include glioblastomas, astrocytomas, oligodendrogliomas, meningiomas, neurofibromas, ependymomas, Schwannomas, neurofibrosarcomas, etc. In addition to neoplastic cells of the CNS, the invention can be utilized to target for oncolysis both benign and malignant neoplastic cells in the periphery. As used herein, the term periphery is intended to mean all other parts of the body outside of the brain. Thus, a peripheral tumor is intended to mean a tumor in a part of the mammalian body outside of the brain (i.e., breast, liver, colon, pancreas, lung, stomach, etc.).

The Transgene Carried by the Herpes Viral Mutant

In addition to having a tumor-specific or cell-specific promoter drive expression of the herpes γ34.5 gene (and possibly one or more additional mutations, such as, e.g., RR, TK, UNG, or dUTPase, as described above), the viral mutants of the present invention can also carry a heterologous transgene.

The transgene can be a suicide gene, that is, a gene that encodes a gene product capable of activating a chemotherapeutic agent to its cytotoxic form, such as HSV-TK, CD, or cytochrome P450. In a preferred embodiment, the suicide gene is a cytochrome P450 gene.

By "gene product capable of converting a chemotherapeutic agent to its cytotoxic form" is meant a gene product that acts upon the chemotherapeutic agent to render it more cytotoxic than it was before the gene product acted upon it. Other proteins or factors may be required, in addition to this gene product, in order to convert the chemotherapeutic agent to its most cytotoxic form.

By "transgene encoding a gene product capable of converting a chemotherapeutic agent to its cytotoxic form" is meant a nucleic acid that upon expression provides this gene product.

"Cytotoxic" is used herein to mean causing or leading to cell death.

"Gene product" broadly refers to proteins encoded by the particular gene.

"Chemotherapeutic agent" refers to an agent that can be used in the treatment of neoplasms, and that is capable of being activated from a prodrug to a cytotoxic form. Preferably, the chemotherapeutic agents for use in the invention do not significantly inhibit replication of the viral mutant, which means that viral replication can occur at a level sufficient to lead to death of the infected cell and to propagate the spread of the virus to other cells.

The term "gene encoding cytochrome P450" means a mammalian cytochrome P450 gene such as, P450 2B1, P450 2B6, P450 2A6, P450 2C6, P450 2C8, P450 2C9, P450 2C 11, or P450 3A4. Each of these genes has been linked to activation of the anticancer drugs cyclophosphamide and ifosfamide (Clarke et al., *Cancer Res.* 49:2344–2350 (1989); Chang et al., *Cancer Res.* 53:5629–5637 (1993); Weber and Waxman, *Biochemical Pharmacology* 45:1685–1694 (1993)), and the cDNA sequences of these genes have also been published (Nelson et al., *DNA and Cell Biology* 12:1–51 (1993) and references cited therein; Yamano et al., *Biochem.* 29:1322–1329 (1990); Yamano et al., *Biochem.* 28:7340–7348 (1989)). Moreover, cytochrome P450 can also activate N-methyl cyclophosphamide (N-methyl CPA), methylchloropropylnitrosourea (MCPNU), and polymeric forms of CPA, ifosfamide, -methyl CPA, and MCPNU. Polymeric forms of chemotherapeutic agents are discussed in Brem, *Biomaterials,* 11: 699–701 (1990); Buahin and Brem, *J. Neurooncol* 26: 103–110 (1995); Tamargo et at., *Cancer Res.* 53: 329–333 (1993); and Langer, *Ann. Biomed. Eng.* 23: 101–111 (1995).

Persons of ordinary skill in the art should be able to utilize the method of the present invention with numerous other anticancer drugs that are activated by members of the cytochrome P450 family of enzymes (LeBlanc and Waxman, *Drug Metab. Rev.* 20:395–439 (1989)), as well as with drug-metabolizing cytochrome P450 genes from other species (e.g., mouse, rabbit, hamster, dog, etc.) that are homologous to cytochromes P450 2B1, P450 2B6, P450 2A6, P450 2C6, P450 2C8, P450 2C9, P450 2C 11, or P450 3A4, and whose cDNA sequences are known (Nelson et al., DNA and Cell Biology 12:1–51 (1993)). In a particularly preferred embodiment, the gene encoding cytochrome P450 2BI is used.

If the herpes viral mutant contains a suicide gene, the chemotherapeutic agent that is activated by the suicide gene should not significantly inhibit replication of the viral mutant so as to allow the viral mutant to kill tumor cells by viral oncolysis, as well as by delivery of the suicide gene. The use of a chemotherapeutic agent/transgene combination in which the chemotherapeutic agent, or its active metabolites, act instead by crosslinking DNA or by inhibiting DNA repair would not significantly inhibit replication of the viral mutant. Thus, such chemotherapeutic agent/ transgene combinations are encompassed by the viral mutant and methods of the present invention.

Thus, a preferred chemotherapeutic agent/transgene combination is cytochrome P450 combined with CPA, ifosfamide, -methyl cyclophosphamide, MCPNU, or polymeric forms of: CPA, ifosfamide, -methyl cyclophosphamide and MCPNU. A more preferred chemotherapeutic agent/transgene combination is CPA/cytochrome P450 2B 1.

Other chemotherapeutic agent/transgene combinations for use in the present invention include: CB 1954/*E. coli* nitroreductase (Friedlos et al., *Gene Ther.* 5: 105–112 (1998); Green et al., *Cancer Gene Ther.* 4: 229–238 (1997)); topoisomerase I or II inhibitors/enzyme with esterase-like activity, such as, e.g., CPT-11/carboxylesterase (Jansen et al., *Int. J. Cancer* 70: 335–340 (1997); Danks et al., *Cancer Res.* 58: 20–22 (1998)); 4-ipomeanol/cytochrome P450 4B1 (Verschoyle et al., *Toxicol. Appl. Pharmacol.* 123: 193–198 (1993)); and 2-aminoanthracene/cytochrome P450 4B 1 (Smith et al., *Biochem. Pharmacol.* 50: 1567–1575 (1995)).

The use of an alkylating agent such as CPA, while providing an anticancer effect, does not significantly inhibit viral protein synthesis or viral replication. The explanation for this finding may lie in the mode of action of these drugs. CPA's active metabolite, phosphoramide mustard (PM) produces interstrand and intrastrand crosslinks in cellular DNA. Maximum cytotoxicity to cellular DNA is usually achieved during mitosis when multiple DNA strand breaks occur at the cross-link sites (Colvin, in *Cancer Medicine.* eds. Holland et al., 1993. Lea and Fabiger, Philadelphia, pages 733–734). In contrast, non-mitotic, cross-linked viral DNA may be spared from extensive damage and may be thus be repaired more readily than cellular DNA.

Ganciclovir is one example of a chemotherapeutic agent that, when activated, inhibits viral replication. Although it has been demonstrated that the combination of hrR3 and ganciclovir provides a significant anticancer effect due to the conversion of ganciclovir by the viral thymidine kinase gene (Boviatsis et al., *Cancer Res.* 54: 5745–5751 (1994)), the converted ganciclovir molecules also inhibit viral replication. For this reason, use of TK/GCV may not be a preferred selection in this paradigm. Prodrug-activating enzymes, such as HSV-TK generate anticancer metabolites that act as "false" nucleotides, producing premature termination of replicating DNA strands. Therefore, these prodrug-activating enzymes would be expected to affect both viral and genomic DNA synthesis and would not be a good choice for use in the herpes viral mutants of the invention that contain a suicide gene.

Another advantage of using chemotherapeutic agents whose mechanism of action is the cross-linking of DNA or the inhibition of DNA repair enzymes is that these agents are effective against even cells in $G_0$. Thus, for these agents to be effective in killing neoplastic cells, the targeted cells do not have to be actively dividing at the time that the drug is administered. This is a significant benefit for tumors in which a large percentage of cells are in $G_0$.

One example of this type of tumor is the glioblastoma. For glioblastomas, the growth fraction, or the relative proportion of cells proliferating in the tumor at any one time, is only 30%, with the remaining 70% of cells being in $G_0$. These tumors are especially resistant to chemotherapeutic agents that target only actively dividing cells because, while the 30% of glioblastoma cells that are actively dividing contribute to the lethal progression of this tumor, 70% of the cells are in $G_0$ and may die or may re-enter the active cell cycle, Yoshii et al., *J. Neurosurg.* 65:659–663 (1986)). Thus, the 70% that are quiescent are responsible for the resistance of these tumors to chemotherapeutic agents that target actively proliferating cells.

This example demonstrates another advantage of the invention. The viral mutant and method of the present invention provide an advantage over therapies based on replication-conditional or replication-incompetent viral mediated oncolysis alone, in that those therapies will target only those cells that can complement the viral mutation. Whereas, although the viral mutant of the invention targets cells with elevated levels of E2F (primarily neoplastic cells) for replication in, and lysis, expression of the transgene and activation the chemotherapeutic agent provides active metabolites that can then diffuse to surrounding tumor cells. These metabolites can thereby kill even those surrounding tumor cells in $G_0$ (70% of the cells in a glioblastoma).

Accordingly, the invention finds particular use in the treatment of glioblastomas. The glioblastoma represents approximately 30% or 50% of all primary brain tumors and, despite surgery, chemotherapy, and radiation therapy, is almost universally fatal.

Due to local activation of the chemotherapeutic agent by the gene product of the gene carried by the herpes viral mutant, the method of the invention should allow more tumor toxicity at the same drug concentration, thus allowing for higher tumor doses without increasing toxicity to normal cells. Further, chemotherapeutic treatment of systemic tumor populations may also be improved by using the method of the present invention because lower doses of the drug may be possible by virtue of increased efficiency.

Furthermore, local activation of the chemotherapeutic agent provides another benefit. Some chemotherapeutic agents require activation or conversion to their active state in cells or organs in the periphery, however, often the active (cytotoxic) metabolites cannot cross the blood brain barrier, and thus are not effective against brain tumors. Thus, the method of the invention should allow treatment of brain tumors by these chemotherapeutic agents. One such chemotherapeutic agent is CPA. CPA is largely ineffective against central nervous system neoplasms as its conversion to DNA-alkylating, cytotoxic metabolites is restricted primarily to the liver and these metabolites do not readily cross the blood-brain barrier. However, the use of the viral mutant of the invention, engineered to carry a cytochrome P450 gene and applied to a brain tumor, would provide for local activation of CPA. Thus, in a preferred embodiment, a cytochrome P450 gene is utilized to sensitize central nervous tumor cells to the cytotoxic effects of cyclophosphamide (CPA).

In addition to a "suicide gene", the transgene can also encode a cytokine to stimulate or enhance a tumor-directed immune response. See, Blankenstein, T., et al., *J. Exp. Med.* 173:1047–1052 (1991); Colombo, M. P., et al., *Cancer Metastasis Rev.* 16:421–432 (1997); Colombo, M. P., et al., *Immunol. Today* 15:48–51 (1994)). Representative examples include tumor necrosis factor alpha (TNF-α), interferon-γ, interleukins (IL-2, IL-4), or granulocyte-macrophage colony stimulating factor (GM-CSF)).

The transgene could also encode a tumor suppressor gene, or any other tumoricidal gene known to those skilled in the art, such as diptheria toxin (Coll-Fresno, P. M., et al., *Oncogene* 14:243–247 (1997)), pseudomonas toxin, anti-angiogenesis genes, tumor vaccination genes, radiosensitivity genes, antisense RNA, or ribozymes (Zaia, J. A., et al., *Ann. N.Y. Acad. Sci.* 660:95–106 (1992)).

Thus, in this embodiment of the invention, the herpes viral mutant, with a tumor-specific or cell-specific promoter driving expression of the γ34.5 gene, further comprises a transgene encoding a gene product capable of converting a chemotherapeutic agent to its cytotoxic form or any other tumoricidal transgene, as mentioned above. The transgene can be inserted in the viral genome in any location where it will be expressed. Preferred locations in the viral genome for the transgene are at the locus of the original γ34.5 deletion or anywhere in the herpes UL40 locus.

Administration of the Herpes Viral Mutant

Exemplary candidates for treatment according to the presently claimed methods include, but are not limited to: (i) non-human animals suffering from neoplasms characterized by a tumor-specific promoter or cell-type specific promoter; (ii) humans suffering from neoplasms characterized by a tumor-specific promoter or cell-type specific promoter; (iii) humans or non-human animals in need of eradication of a particular cell population.

By "neoplastic cells" is intended cells whose normal growth control mechanisms are disrupted (typically by accumulated genetic mutations), thereby providing the potential for uncontrolled proliferation. The term is intended to include both benign and malignant neoplastic cells in both the central nervous system and the periphery. As used herein, the term "periphery" is intended to mean all other parts of the body outside of the brain or spinal cord.

For purposes of the invention, neoplastic cells include cells of tumors, neoplasms, carcinomas, sarcomas, papillomas, leukemias, lymphomas, and the like. Of particular interest are solid tumors that may arise in any organ or tissue of the mammalian body.

Malignant brain tumors, include astrocytoma, oligodendroglioma, meningioma, neurofibroma, glioblastoma, ependymoma, Schwannoma, neurofibrosarcoma, and medulloblastoma.

Preferentially, the treatment will be initiated by direct intraneoplastic inoculation. For tumors in the brain, MRI, CT, or other imaging guided stereotactic techniques may be used to direct viral inoculation, or virus will be inoculated at the time of craniotomy. For patients attempting to eradicate a particular cell population, the vector would be inoculated into the tissue of interest.

Generally, methods are known in the art for viral infection of the cells of interest. For example, the viral mutant can be injected into the host at or near the site of neoplastic growth, or administered by intravascular inoculation. Typically, the viral mutant would be prepared as an injectable, either as a liquid solution or a suspension; a solid form suitable for solution in, or suspension in, liquid prior to injection may also be prepared. The preparation also may be emulsified. The active ingredient is preferably mixed with an excipient which is pharmaceutically-acceptable and compatible with the active ingredient. Suitable excipients are, for example, water, saline, dextrose, glycerol, ethanol, or the like and combinations thereof. In addition, if desired, the preparation may contain minor amounts of auxiliary substances such as wetting or emulsifying agents, pH-buffering agents, adjuvants or immunopotentiators which enhance the effectiveness of the viral mutant (See, *Remington's Pharmaceutical Sciences*, Gennaro, A. R. et al., eds., Mack Publishing Co., pub., 18th ed., 1990). Examples of non-aqueous solvents are propylene glycol, polyethylene glycol, vegetable oil and injectable organic esters such as ethyloleate. Aqueous carriers include water, aqueous solutions, saline solutions, parenteral vehicles such as sodium chloride, Ringer's dextrose, etc. Intravenous vehicles include fluid and nutrient replenishers. Determining the pH and exact concentration of the various components of the pharmaceutical composition is routine and within the knowledge of one of ordinary skill in the art (See *Goodman and Gilman's The Pharmacological Basis for Therapeutics*, Gilman, A. G. et al., eds., Pergamon Press, pub., 8th ed., 1990).

Additional formulations which are suitable include oral formulations. Oral formulations include such typical excipients as, for example, pharmaceutical grades of mannitol, lactose, starch, magnesium stearate, sodium saccharine, cellulose, magnesium carbonate and the like. Oral compositions may take the form of tablets, pills, capsules, sustained release formulations or powders and contain 10%–95% of active ingredient, preferably 25–70%.

The dosage of the viral mutant to be administered, in terms of number of treatments and amount, depends on the subject to be treated, the capacity of the subject's immune system to synthesize antibodies, and the degree of protection desired. Precise amounts of active ingredient required to be administered depend on the judgment of the practitioner and are peculiar to each individual. For the most part, the virus is provided in a therapeutically effective amount to infect and kill target cells.

Methods for Selectively Killing Neoplastic Cells

The present invention also provides a method for selectively killing neoplastic cells that overexpress a known tumor-specific protein using the herpes viral mutants described above, comprising: infecting said neoplastic cells with said herpes viral mutant, said viral mutant comprising: (a) a deletion or inactivating mutation in a gene encoding γ34.5; and (b) an insertion of at least one copy of said γ34.5 gene under the transcriptional control of the promoter of said tumor-specific protein, such that said promoter drives expression of said γ34.5 gene; and selectively killing said neoplastic cells.

Of course, in the herpes viral mutant used in the above method, there may be more than one specific endogenous deletion or inactivating mutation of a herpes viral gene, in addition to the γ34.5 gene. These include deletions in the gene that encodes ribonucleotide reductase (RR), or more particularly the large subunit of RR. Alternatively, the gene encoding RR encodes the small subunit. Any other herpes viral genes may also be deleted, such as, e.g., thymidine kinase (TK), uracil DNA glycosylase (UNG), or dUTPase. These viral genes are preferred as the mammalian homologues of these genes are often up-regulated in cells with elevated levels of E2F, such as neoplastic cells, and thus can complement the deleted viral enzyme, thereby promoting selective replication in those cells.

Exemplary tumor-specific promoters are described above, and include, for example, promoter elements of the following proteins that are unique to, or are overexpressed in, certain tumor-types: CEA, AFP, tyrosinase, and PSA. Tumor cells are also known to overexpress particular oncogenes, so that cells with upregulated gene expression can be targeted using promoter elements of such genes. B-myb, C-myb, c-myc, c-kit, and the c-erbB2 oncogene are some representative examples of these types. The B-myb promoter (see, Lyon, J., et al., Crit. Rev. Oncogenesis 5:373–388 (1994) contains a consensus E2F binding site, is strictly regulated in cycling cells, and is in fact repressed in $G_0$ (Lam, E. W. and Watson, R. J., *EMBO J.* 12:2705–2713 (1993); Lam, E. W., et al., *Gene* 160:277–281 (1995); Bennett, J. D., et al., Oncogene 13:1073–1082 (1996)). Accordingly, the B-myb promoter is a particularly preferred tumor-specific promoter. In a particularly preferred embodiment of this method, the viral mutant used in the method is Myb34.5.

Any cancer type having a well-characterized promoter would find use in the method of the invention. Examples of such promoters can be found in Table 1 of Clary, B. M., et al., *Cancer Gene Therapy* 7:565–574 (1998); Table I of Spear, M. A., *Anticancer Research* 18:3223–3232 (1998); Table 2 of Walther, W. and Stein, U., *J. Mol. Med* 74:379–392 (1996); and Dachs, G. U., et al., *Oncol. Res.* 9:313–325 (1997)).

Most if not all of the gene sequences of the tumor-specific promoters described above are available from the GenBank Sequence Database.

In addition, the invention provides the above method for selectively killing neoplastic cells, wherein said herpes viral mutant further comprises a transgene, wherein the transgene is a suicide gene, a cytokine gene, or any tumoricidal gene. If the transgene is a suicide gene, then the method further comprises contacting the neoplastic cells with a chemotherapeutic agent capable of being activated by said suicide gene and selectively killing the neoplastic cells. The preferred suicide gene is cytochrome P450. P450 2B1 is particularly preferred. Alternatively, the cytochrome P450 encoded is P450 2B6, P450 2A6, P450 2C6, P450 2C8, P450 2C9, P450 2C11, or P450 3A4. In addition, the chemotherapeutic agent is preferably a member of the oxazosphorine class, particularly cyclophosphamide, ifosfamide, N-methyl cyclophosphamide, methylchloropropylnitrosourea, polymeric cyclophosphamide, polymeric ifosfamide, polymeric N-methyl cyclophosphamide, or polymeric methylchloropropylnitrosourea.

Another embodiment of the invention is a pharmaceutical composition containing the foregoing viral mutants, wherein this composition may also contain one or more pharmaceutically acceptable excipients.

Methods for Selectively Eliminating Target Cell Populations

Another embodiment of the present invention is a method for selectively eliminating a target cell population that overexpresses a known cell-specific protein using the herpes viral mutants of the invention, comprising: infecting said target cells with said herpes viral mutant, said viral mutant comprising: (a) a deletion or inactivating mutation in a gene encoding γ34.5; and (b) an insertion of at least one copy of said γ34.5 gene under the transcriptional control of the promoter of said cell-specific protein, such that said promoter drives expression of said γ34.5 gene; and selectively eliminating a target cell population.

By "selectively eliminating a target cell population" is intended to include a significant reduction in the number of target cells versus non-target cells, as well as the complete or near complete elimination of target cells.

Of course, in the herpes viral mutant used in the above method, there may be more than one specific endogenous deletion or inactivating mutation of a herpes viral gene, in addition to the γ34.5 gene. These include deletions in the gene that encodes ribonucleotide reductase (RR), or more particularly the large subunit of RR. Alternatively, the gene encoding RR encodes the small subunit. Any other herpes viral genes may also be deleted, such as, e.g., thymidine kinase (TK), uracil DNA glycosylase (UNG), or dUTPase.

Exemplary cell-specific promoters include the following: endothelial nitric oxide synthase (eNOS) promoter expressed in endothelial cells (Guillot, P. V., et a, *J. Clin. Invest.* 103:799–805 (1999)); vascular endothelial growth factor (VEGF) receptor (flk1) promoter expressed in endothelial cells (Kappel et al. *Blood* 93: 4282–4292 (1999)); insulin promoter expressed in beta cells of the pancreas (Ray et al., *J. Surg. Res.* 84: 199–203 (1999)); promoter of gonadotropin-releasing hormone receptor gene expressed in cells of the hypothalamus (Albarracin et al., *Endocrinology* 140: 2415–2421 (1999)); matrix metalloproteinase 9 promoter expressed in osteoclasts and keratinocytes (Munant et al., *J. Biol. Chem.* 274: 5588–5596 (1999)); promoter of parathyroid hormone receptor expressed in bone cells (Amizuma et al., J. Clin. Invest. 103: 373–381 (1999)); and dopamine beta-hydroxylase promoter expressed in noradrenergic neurons (Yang et al., *J. Neurochem.* 71: 1813–1826 (1998)).

Examplary applications of this embodiment include the following:

1) Treatment options to eliminate a noxious cell population: For example, in conditions where there is exuberant neovascularization of blood vessels, such as cerebral Moya—Moya disease, use of the flk1 receptor promoter to drive γ34.5 gene expression would allow for selective elimination of the blood vessels causing this disease. Another example is in conditions where there is extensive bone remodeling and elimination of bone, such as osteoporosis, the use of the promoters of matrix metalloproteinase 9 or the parathyroid hormone receptor to drive expression of γ34.5 would eliminate bone osteoclasts from further remodeling of bone.

2) To study developmental processes: In order to study the effect of elimination of a cell population on developmental processes, one could use, for example, the dopamine-beta-hydroxylase promoter to eliminate the noradrenergic neurons and then study the effect on animal development.

The following examples are offered by way of illustration, not by way of limitation.

EXAMPLE 1

(Neural Neoplasms)

Introduction

Deletion of the γ34.5 gene encoding for virulence markedly reduces cytotoxicity mediated by herpes simplex virus (HSV). To target lytic virulence to tumors, the inventors created a herpes simplex virus (HSV-1) mutant designated Myb34.5. This viral mutant is characterized by deletions in ICP6 (also known as UL39 or ribonucleotide reductase) and of the two endogenous copies of the γ34.5 gene (RL1) and by reintroduction of one copy of γ34.5 under control of the E2F-responsive, cellular B-myb promoter.

On direct intracerebral inoculation in mice, Myb34.5 remained as a virulent as a γ34.5 mutant virus. However, its oncolytic efficacy against a variety of human glioma cells in culture and in vivo was similar to that of a single ICP6 mutant strain that possesses a wild-type γ34.5 gene. This combination of antitumor efficacy and retained neuroattenuation suggests that cell cycle-regulated promoters can be used to target HSV-1 virulence toward tumors, while maintaining the desirable neuroattenuated phenotype of a γ34.5 mutant.

Methods and Materials

Plasmids and Viruses —HSV strain F (wild-type) was acquired through the American Type Culture Collection ATCC (Manassas, Va.). Mutant virus R3616 (Chou, J., et al., Science 250:1262–1266 (1990)) (containing 1000 bp BstEII-StuI deletions within both γ34.5 loci) was kindly provided by Dr. B. Roizman, University of Chicago. Mutant virus hrR3 (Goldstein, D. J. and Weiner, S. K., J. Virol. 62:196–205 (1988)) (kindly provided by S. Weller, University of Connecticut) contains an E. Coli lacZ cDNA inserted into the UL39 locus. The mutant virus MGH1 is characterized by insertion of the Escherichia coli lacZ cDNA into the UL39 locus and deletions of both γ34.5 loci, and it was constructed by recombination of the ICP6-lacZ region of hrR3 into the viral mutant R3616 (Kramm, C. M., et al., Hum. Gene Ther. 8:2057–2068 (1997)).

Plasmid pKX-BG3, which contains the lacZ gene within a 2.3 kb XhoI region of ICP6 (KOS origin, see, Goldstein, D. J. and Weller, S. K., J. Virol. 62:2970–2977 (1988)), was provided by S. Weller, as was plasmid pKpX2, which contains 2.3 kb of the ICP6 (UL39) gene. Plasmid pBGL34.5, containing the entire γ34.5 coding sequence, was provided by Xandra Breakefield and Peter Pechan (MGH). The B-myb promoter was excised as a KpnI-HindIII fragment from plasmid pBGL2myb (kindly provided by Dr. R. Watson, Ludwig Institute for Cancer Research, UK) and directionally cloned upstream of γ34.5.

Engineering of Myb34.5 and of a Myb34.5 revertant— The plasmid used for the engineering of Myb34.5 by homologous recombination into MGH1 was designed to replace the lacZ cDNA in MGH1 in its entirety and delete an additional 888 nucleotides of ICP6 (UL39) sequence. Specifically, the recombining plasmid (pKpX2-myb34.5) was engineered as follows. The full-length γ34.5 cDNA was excised as an NcoI-SacI fragment from pBGL34.5, it was blunt-ended, and then it was subcloned into pBSKII (Stratagene, La Jolla, Calif.) to generate plasmid pBS34.5. The B-myb promoter was excised as a KpnI-HindIII fragment from pBGL2myb and directionally cloned upstream of γ34.5 in pBS34.5. The resulting expression cassette, containing the B-myb promoter upstream of the γ34.5 cDNA, was excised as KpnI-XbaI fragment, was blunt-ended, and was then subcloned into the NruI sites of pKpX2. Through this process, the intervening NruI—NruI fragment within UL39 was deleted. The resulting plasmid, pKpX2-myb34.5, was then linearized with ScaI and contransfected with MGH1 viral DNA into Vero cells at various molar ratios with Lipofectamine (Gibco, Gaithersburg, Md.). Virus progeny was harvested 5 to 7 days following transfection when cytopathic effects were evident. This progeny was released from cells through three cycles of freeze-thawing, and it was then plated onto a monolayer of Vero cells. After overlayering the monolayer with agarose, incubation at 37° C. in an atmosphere containing 5% carbon dioxide was performed.

Plaques were then stained with 5-bromo-4-chloro-3-indolyl-β-D-galactopyranoside (X-Gal). Colorless plaques were selected as potential recombinants. These isolates underwent three rounds of plaque purification before having their genetic identity tested by Southern blot analysis. A Myb34.5 revertant (MybRevt) was engineered by using Myb34.5 as the parental strain and pKX-BG3 as the plasmid for homologous recombination of the lacZ cDNA back into the ICP6 locus and deletion of the B-myb/γ34.5 expression cassette.

Southern Blot Analysis—Viral DNAs were isolated after cell lysis of infected Vero cells with SDS/proteinase K, repeated phenol-chloroform extraction and ethanol precipitation. DNA was digested with appropriate restriction endonucleases (New England Biolabs, Beverly Mass.), separated by agarose electrophoresis, and transferred to a nylon membrane (Amersham Corp., Arlington Heights, Ill.). Probes included the HindIII-XbaI ICP6 fragment from pKpX2, the BstEII-BbsI fragment from pBSKγ34.5, and a BbsI fragment of lacZ from pKX-BG3. Probe labeling and hybridizations were performed using the ECL chemiluminescence system (Amersham) according to the manufacturer's protocol.

Cell culture studies—All cells were cultured at 37° C. in an atmosphere containing 5% carbon dioxide in Dulbecco's minimal essential medium (DMEM) supplemented with 10% fetal calf serum, 100 U of penicillin/ml, and 10 μg of streptomycin/ml. Host protein synthesis shutoff studies were performed by infecting cells with viral strains for 16 hours. Cells were then placed in methionine-free medium for 10 minutes, then labeled using $^{35}$[S]-methionine (New England Nuclear, Boston Mass.) for 90 minutes. Cells were then washed with phosphate buffered saline (PBS) pH 7, solubilized, subjected to SDS polyacrylamide gel electrophoresis, transferred to a nitrocellulose membrane, and subjected to autoradiography. Protein concentrations were calculated with a commercially available kit (Bio-Rad, Hercules Calif.). Infected cell polypeptides (ICP) were labeled, as previously published (Morse, L. S., et al., J. Virol. 26:389–410 (1978)). Human glioblastoma cell lines U87, U373, T98G, and U343; rat gliosarcoma 9L cells; human neuroblastoma SKNSH cells and Vero (African green monkey) cells were obtained from the American Type Culture Collection (Manassas, Va.) and cultured with DMEM or minimal alpha essential medium (Gibco) supplemented with 10% serum and antibiotics. Primary mouse fetal striatal neurons (embryonic stage 18) (kindly provided by M. Schwarzchild, Massachusetts General Hospital, Charlestown, Mass.) were isolated using published procedures (Schwarzschild, M. A., et al., J. Neurosci. 17:3455–3466 (1997)).

Animal studies—Nude (nu/nu) mice were obtained from the Cox 7 breeding facility, Massachusetts General Hospital (MGH). BALB/C mice were obtained from Charles River Laboratories (Wilmington, Mass.). Subcutaneous tumors were obtained by injection of $2\times10^5$ cells in the flanks of athymic mice (five animals per group for 9L gliosarcoma cells, and six animals per group for human U87ΔEGFR glioma cells). Fourteen (for 9L) or ten (for U87ΔEGFR) days after tumor implantation, animals with similar tumor volumes were randomly divided, and various viral strains were injected intratumorally at $5\times10^7$ PFU/dose in 100 ul volumes on days 1, 3, 5, and 7. Animals were euthanized at day 33 (9L) or day 34(U87ΔEGFR). Tumor volumes were measured with external calipers, as previously described (Wei, M. X., et al., Hum. Gene Ther. 5:969–978 (1994)). For neurotoxicity experiments, BALB/C mice were stereotactically injected in the right frontal lobe (depth 3 mm) with 10

µl volumes of virus at different dilutions, up to the highest stock titers obtainable. Animals were checked daily for 28 days. All animal studies were performed in accordance with guidelines issued by the MGH Subcommittee on Animal Care. Viral inoculation and care of animals harboring viruses were performed in approved viral vector rooms.

Results

Figure 1B:
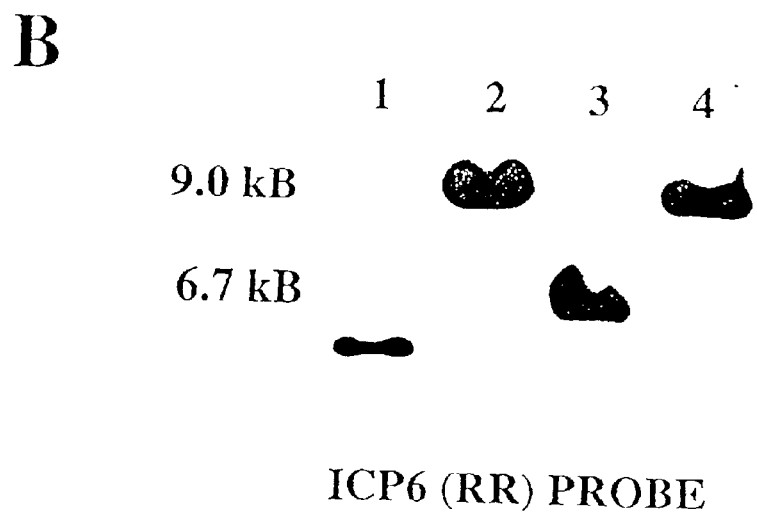
Figure 1C:
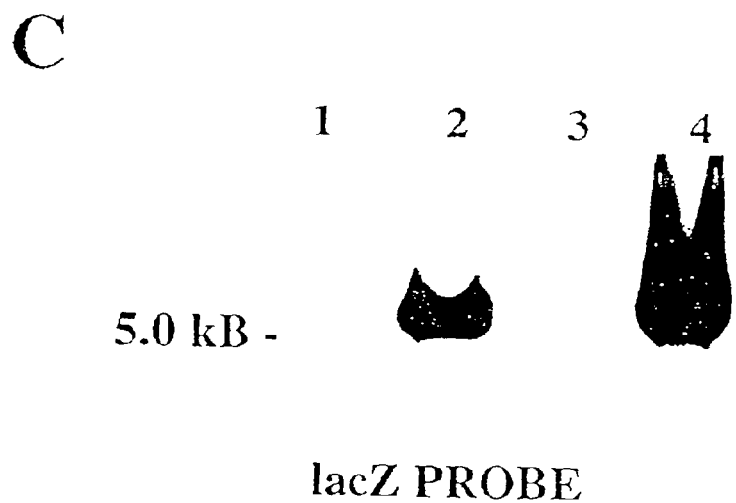
Figure 1D:

Genetic engineering of Myb34.5—The multiply mutated virus Myb34.5 was constructed by recombining a B-myb promoter/γ34.5 construct into the UL39 (also known as ICP6 or RR) locus of MGH1. MGH1 (Kramm, C. M., et al., Hum. Gene Ther. 8:2057–2068 (1997)) was generated by recombining a lacZ cDNA into the ICP6 locus of the γ34.5 deletion mutant R3616 (Chou, J., et al., Science 250:1262–1266 (1990)). FIG. 1A provides a schematic of the DNA structure of Myb34.5. This structure was confirmed by restriction endonuclease mapping (data not shown), Southern blot hybridization (FIGS. 1B to 1D), and sequence analysis (data not shown) of the junctions between UL39 and the B-myb promoter/γ34.5 expression cassette. To show the deletion of lacZ in Myb34.5, XhoI-digested Myb34.5 DNA was hybridized to probes containing either ICP6 (FIG. 1B) or lacZ sequence (FIG. 1C). As expected, the parental virus, MGH1, contained a 9.0 kb XhoI ICP6-lacZ fragment (Kramm, C. M., et al., supra.) that hybridized to an ICP6 probe (FIG. 1B). Homologous recombination led to the deletion of lacZ and additional ICP6 sequence and insertion of the B-myb promoter/γ34.5 sequence. This is evident by hybridization of the ICP6 probe to a 6.7 kb fragment in Myb34.5 DNA (FIG. 1B). Hybridization with a lacZ probe revealed the absence of hybridizing fragments in digested DNA from Myb34.5 and the presence of the expected 9.0 kb hybridizing fragment in digested DNA from MGH1 (FIG. 1C). To confirm that Myb34.5 possessed a reintroduction of the γ34.5 gene, BamHI-digested viral DNA was hybridized with a BstE11-Bbsγ34.5 fragment (internal to the deleted regions). This demonstrated a ladder of hybridizing bands that is typically observed with the wild-type F strain. As discussed in the work of Chou et al. (1991), supra, γ34.5 maps in BamHI S and SP fragments, forming a characteristic ladder of bands at 500 bp increments, which are a consequence of a variable number of a sequences in the repeats flanking the unique sequences of the long component. This ladder is observed in the Southern blot for the F strain (lane 1 of FIG. 1D), where the top hybridizing bands represent the BamHI SP fragment, formed by the fusion of the terminal BamHI S fragment with BamHI P, while the lower hybridizing bands represent the BamHI S fragment (Chou, J., et al., Science 250:1262–1266 (1990)).

In R3616 and its derived viruses, MGH1, Myb34.5, and Myb34.5Revt, a similar ladder of hybridizing bands whose molecular size was decreased by approximately 1 kb (the size of the internal deletion of γ34.5 in R3616) would be expected if a full-length γ34.5 cDNA probe were employed for hybridization. In fact, in the work of Chou et al. (Chou, J., et al., Science 250:1262–1266 (1990)), this pattern of hybridization is evident for R3616, and in the work of Kramm et al. (Kramm, C. M., et al., Hum. Gene Ther. 8:2057–2068 (1997)), this pattern of hybridization is evident for MGH1. However, for the Southern analysis shown in FIG. 1D, a BstEII-Bbs γ34.5 fragment that is internal to the 1 kb deleted fragment of the γ34.5 gene of R3616, MGH1, Myb34.5, and Myb34.5Revt was employed as a probe. Therefore, no hybridizing bands are observed for MGH1 (FIG. 1D, lane 2) and Myb34.5Revt (FIG. 1D, lane 4), while a single 5.3 kb hybridizing fragment is observed for Myb34.5 (FIG. 1D, lane 3), corresponding to the γ34.5 gene, reintroduced into the ICP6 locus.

In order to demonstrate that the altered phenotype of Myb34.5 was the result of the B-myb/γ34.5 insertion, a revertant (marker-rescued) virus was also engineered, and designated MybRevt. This was achieved by homologous recombination, with Myb34.5 as the parental strain, and linearized pKX2-BG3 as the recombining plasmid. This plasmid contains the lacZ/ICP6 insertion and was used to create hrR3, the source of the ICP6::lacZ fusion region in MGH1 (Kramm, C. M., et al., Hum. Gene Ther. 8:2057–2068 (1997); Goldstein, D. J. & Weller, S. K., J. Virol. 62:2970–2977 (1988)). The MybRevt revertant demonstrated a pattern on Southern hybridization to the ICP6 (FIG. 1B), lacZ (FIG. 1C), and γ34.5 (FIG. 1D) probes, that was identical to that shown by MGH1, the parent strain of Myb34.5.

Figure 2:
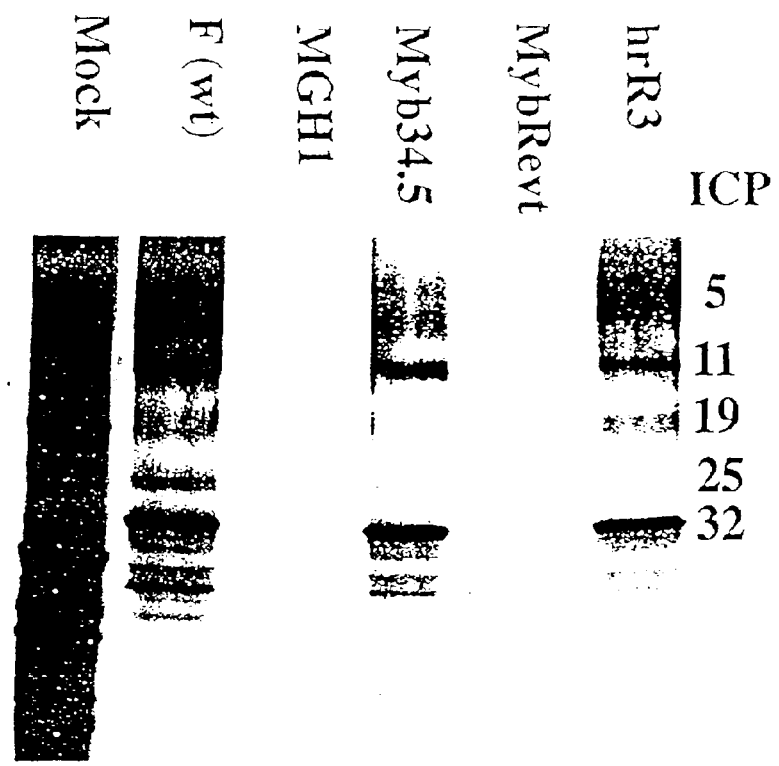
FIG. 2 depicts an autoradiographic image of electrophoretically separated lysates of infected cells demonstrating inhibition of host protein synthesis shutoff by mutant viral strains. Human neuroblastoma cells (SK-N—SH) were plated at $1\times10^6$ cells/100 mm dish. Twenty-four hours later cells were infected at an MOI of 3.0. Fifteen hours following viral infection, cells were briefly washed with methionine-free medium then incubated for 90 minutes with media containing 60 µCi $S^{35}$-methionine (Toda, M., et al., *Hum. Gene. Ther.* 9:2177–2185 (1998)). After labeling, cells were harvested, solubilized in a buffer containing SDS, and electrophoresed on 10% acrylamide gels. The gels were then transferred to nitrocellulose and subjected to autoradiography. Infected cell polypeptides were designated according to Morse, L. S., et al., *J. Virol.* 26:389–410 (1978).

Functional expression of γ34.5—To confirm that Myb34.5 produced functional γ34.5 protein, human SKNSH neuroblastoma cells were infected with a variety of viral strains. FIG. 2 shows that, as expected, MGH1 and the revertant virus (MybRevt) failed to prevent the infected cell response consisting of shut-off of protein synthesis, which is characteristic of intact γ34.5 function (Chou, J., 1992, supra). However, Myb34.5 and other strains with intact γ34.5 (wild-type F and hrR3) prevented the infected cell response (shut-off of protein a synthesis), thus leading to viral protein production.

Additional evidence that Myb34.5 expressed functional γ34.5 protein was provided by assessment of viral replication in the U373 glioblastoma cell line which has been previously noted to restrict replication of γ34.5 mutant HSV strains (Mohr. I. and Bluzman, Y., EMBO J. 15:4759–5766 (1996)). After infecting $5 \times 10^5$ cells at a MOI of 1.0 and harvesting viral output 48 hours later, Myb34.5 yields were similar to those of wild-type F strain ($1.1 \times 10^7$ PFU vs. $5.0 \times 10^7$ PFU, respectively). In contrast, yields of MGH1 ($3.3 \times 10^4$ PFU) or MybRevt ($3.4 \times 10^4$ PFU, averages of triplicate experiments) were significantly less. The ability of Myb34.5 to efficiently replicate in this non-permissive line, in contrast to that of MGH1 or MybRevt, indicates that the encoded γ34.5 in Myb34.5 was functional.

Neurotoxicity Studies—One important characteristic of any replication-competent HSV strain is its level of neurovirulence, which can be assessed both in vitro and in vivo. The ability of the Myb34.5 virus to replicate in primary neuronal cultures was measured in comparison to the F, hrR3, MGH1, and MybRevt strains. Murine fetal striatal neurons were infected, and viral yields were assessed by plaque assay on Vero cells (which do not require γ34.5 for efficient viral replication). While the wild-type F strain demonstrated vigorous replication in neurons, all the mutant strains, including Myb34.5, demonstrated minimal viral replication (See, Table 1).

TABLE 1

Viral Replication in Primary Neuronal Culture*

| HSV Strain | Mean (SEM) Viral Output (PFU) |
| --- | --- |
| F (wt) | $1.0 \times 10^7$ ($1.4 \times 10^6$) |
| hrR3 | $4.1 \times 10^3$ ($4.2 \times 10^2$) |
| MGH1 | $1.4 \times 10^3$ (73) |
| Mybγ34.5 | $6.0 \times 10^3$ ($4.3 \times 10^2$) |
| MybRevt | $1.5 \times 10^3$ (74) |

TABLE 1-continued

Viral Replication in Primary Neuronal Culture*

| HSV Strain | Mean (SEM) Viral Output (PFU) |
| --- | --- |

*A total of $2.5 \times 10^5$ murine fetal (day 18) striatal neurons were harvested and plated as previously described (Chase, M., et al, Nat. Biotechnol. 16:444–448 (1998)). Two days after plating, cells were infected at MOI of 0.1 with wild-type (strain F) and mutant viral strains in duplicate experiments. Twenty-four hours after infection, cells and supernatant were harvested and subjected to freeze-thaw cycles to liberate viral particles. Viral output was determined by plaque assay on Vero cells. Standard errors (SEM) are enclosed in parentheses. Viral outputs of the four mutant viral strains (hrR3, MGH1, Myb34.5, and MybRevt) were not statistically different between groups (t-test, p > 0.3).

In the in vivo setting, direct intracerebral inoculation of Myb34.5 in BALB/C mice demonstrated that the virus remains markedly neuroattenuated relative to wild-type HSV. Table 2 shows that Myb34.5's $LD_{50}$ was $2.7 \times 10^7$ PFU, at least 3 logarithmic units higher than that of F strain (wild-type). The γ34.5 mutants (MGH1, R3616, and MybRevt) do not grow well, and achievement of titers of $>10^9$ PFU/ml is prohibitive without large-scale production. This limited the ability to estimate accurately the $LD_{50}$ for these mutants in these experiments. For comparative purposes, one of six mice perished when inoculated intracerebrally with $10^7$ PFU of Myb34.5, while zero of six mice perished when inoculated with the same amount of MGH1. These findings confirmed that reintroduction of γ34.5 under the control of the B-myb promoter produced minimal neurovirulence.

TABLE 2

Comparative ability of wild-type and mutant viral strains to cause death after intracerebral inoculation into mice*

| Virus in inoculum | Description | $LD_{50}$ (PFU) |
| --- | --- | --- |
| HSV-1 (F) | Wild-type | $1.0 \times 10^4$ |
| hrR3 | lacZ insertion in RR | $1.3 \times 10^6$ |
| R3616 | γ34.5 mutant | $>1 \times 10^{7**}$ |
| MGH1 | γ34.5/RR double mutant | $>1 \times 10^{7**}$ |
| Myb34.5 | RR/myb34.5 | $2.7 \times 10^{7***}$ |

*Serial dilutions of virus in serum free media (volume 10 μl) were stereotactically injected into the right hemisphere of three week old female BALB/C mice (Charles River Laboratories, Wilmington, MA, 6 animals per PFU level). Animals were inspected daily for 28 days for mortality, and the $LD_{50}$ in PFU was calculated using a proportional distance model. Double asterisks (**) for R3616 and MGH1 denote that no deaths occurred at the listed dose, which was the highest attainable for these strains in the given injection volume. This is because titers of $>10^9$ PFU/ml could not be technically achieved with these mutants in growing Vero cells without industrial-scale production and intracerebral injections were limited to a maximum volume of 10 μl.
Triple asterisks (***) indicate that in parallel experiments, one death per six animals occurred at a dose of $10^7$ PFU. Since titers of $5 \times 10^9$ to $1 \times 10^{10}$ PFU/ml could be achieved with Myb34.5 in rapidly dividing Vero or tumor cells, a more accurate $LD_{50}$ could be measured.

Figure 3:
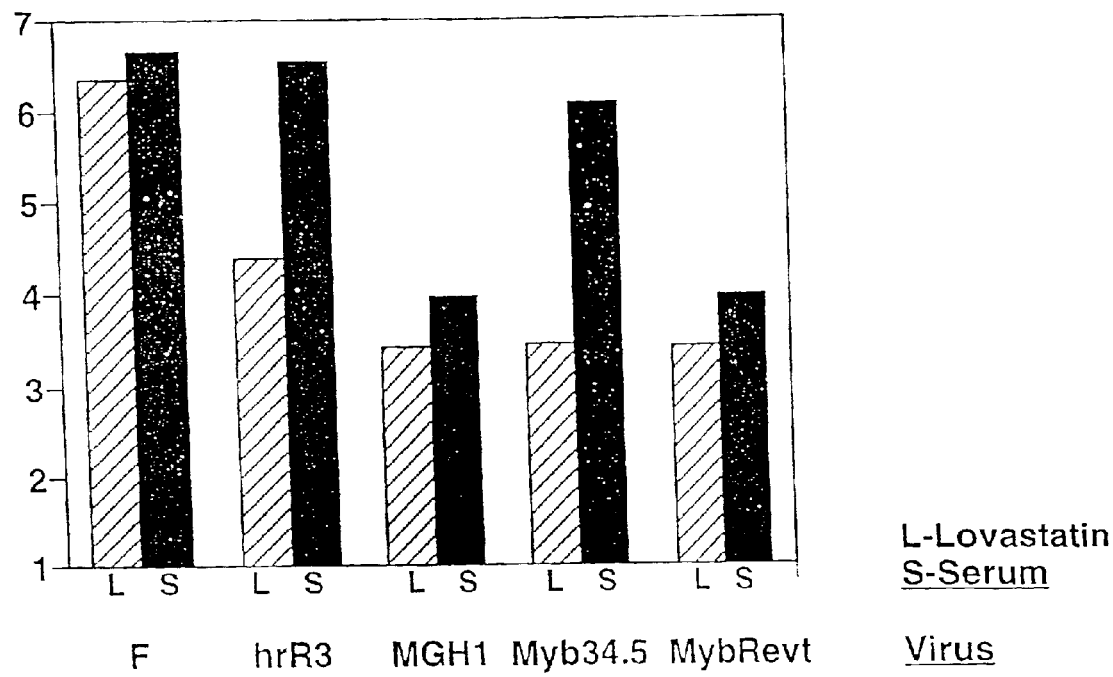
FIG. 3 is a bar graph depicting viral replication in arrested and cycling cells. Human embryo-derived primary fibroblasts (CRL 7706) were plated at $1 \times 10^5$ cells/60 mm dish. Forty-eight hours after plating, media was replaced with DMEM containing 20 µM Lovastatin for 36 hours (hatched bars). Triplicate plates were counted and infected at a multiplicity of infection (MOI) of 1.0 with various mutant strains (triplicate experiments). Forty-eight hours after infection, cells and supernatants were harvested and virus liberated by freeze-thaw cycles. Parallel experiments were performed with cells allowed to remain in medium containing 110% fetal bovine serum (solid bars). Viral output was determined by plaque assay on Vero cells and is represented as log 10 PFU/$1 \times 10^5$ input virus (values reflect averages of triplicate experiments). Lovastatin outputs were statistically lower than those obtained with serum for the tested viruses (Student's t-test values: F, p=0.027; hrR3, p=0.001; MGH1, p=0.001; Myb34.5, p=0.001; MybRevt, p=0.003).

Regulation of γ34.5 gene expression in arrested and cycling cells—In order to further assess the behavior of Myb34.5 in quiescent versus cycling cells, primary human fibroblasts were plated and cell-cycle arrested with 20 μM lovastatin, which has been shown not to interfere with herpes virus replication (Schang, L. M., et al., J. Virol. 72:5626–5637 (1998)). In arrested primary fibroblasts, MGH1, Myb34.5, and MybRevt demonstrated minimal viral replication relative to F strain, at levels 1 logarithmic unit (PFU) lower than the single RR mutant hrR3 (FIG. 3). In contrast, in the presence of serum, hrR3 and Myb34.5 demonstrated marked induction of replication, while MGH1 and MybRevt did not. These results suggested that: 1) γ34.5 is required for efficient replication in this nontransformed cell type, and 2) the B-myb promoter functions to allow efficient replication of Myb34.5 in cycling cells. It is also notable that Myb34.5 exhibited a greater differential in the production of viral progeny in quiescent versus cycling cells than that of hrR3 (3 versus 2 logarithmic units) and that its viral production in quiescent cells was the same as that of the γ34.5 mutant viruses.

Comparative studies on oncolytic effects—To determine the oncolytic efficiency of Myb34.5, five different glioma cell lines (9L, U87, U87ΔEGFR, T98G, and U343) were mock infected (no virus) or infected with a panel of viral strains including F strain, MGH1, Myb34.5, and MybRevt. Surviving cells were counted 48 hours later and expressed as a percentage of cells surviving on mock-treated plates. In published studies of rat 9L gliosarcoma cells (Kramm, C. M., et al., Hum. Gene Ther. 8:2057–2068 (1997)) and in unpublished experiments on human glioma cells U343 and T98 (Qureshi, N. and Chiocca, E. A., unpublished data), it had preliminarily been shown that tumor cell killing by MGH1 was similar to that by R3616 for two human glioma lines (Table 3), and thus the latter mutant was excluded from further analysis.

In all tumor cell lines tested, Myb34.5 demonstrated greater oncolytic efficiency in vitro than did the parental strain MGH1, and for some tumor cell lines its oncolytic efficacy approached that of the wild-type virus (Table 3). These findings thus showed that the oncolytic effect of Myb34.5 was greater than that of the γ34.5 mutant viruses (MGH1, MybRevt, and R3616, whose killing efficacy closely replicates that of MGH1).

TABLE 3

In vitro glioma cell killing by wild-type and mutant HSV strains*

| | % Survival (SEM) After Infection with HSV Strain | | | |
| --- | --- | --- | --- | --- |
| Cell line | F | MGH1** | Myb34.5 | MybRevt |
| U87 | 2.9 (0.7) | 52. (2.0) | 19.5 (1.5) | 51 (2.5) |
| 9L | 23.7 (1.7) | 60 (1.2) | 29 (1.4) | 59.5 (1.4) |
| U343 | 19 (1.1) | 35.7 (1.6) | 26.3 (1.1) | 32.3 (3.0) |
| T98G | 26.8 (0.8) | 38.5 (1.0) | 29.3 (1.7) | 40 (1.2) |
| U87ΔEGFR | 15 (0.4) | 48 (0.3) | 10 (0.6) | 50 (0.7) |

*Human (U87MG, U343, T98G, and U98ΔEGFR) and rat (9L) glioma-derived cell lines were plated at $5 \times 10^5$ cells/60 mm diameter plate and subsequently infected at an MOI of 0.1 with the strains noted. Oncolytic effect is reflected by cell survival at 48 hours post infection, expressed as a percentage of the number of surviving cells from triplicate, non-infected control plates. Values represent averages (SEM in parentheses) of triplicate experiments. Differences in killing of tumor cells by Myb34.5 versus MGH1 or MybRevt were statistically significant. For example, for U87 glioma cells, P was <0.001 (one-way analysis of variance with Tukey pairwise multiple comparison procedures).
**Killing for R3616 was not included in this particular set of experiments because it is relatively similar to that observed with MGH1. This was shown by Kramm et al. (Kramm, C. M., et al., Hum. Gene Ther. 8:2057–2068 (1997)) for rat 9L gliosarcoma cells as well as in a number of previously unpublished experiments performed at a different time from the present experiment. For example, for human U343 glioma cells infected with MGH1 or R3616 cells at an MOI of 0.1, survival rates were 54 and 50%, respectively, at 2 days. For human T98 cells infected with MGH1 or R3616 at an MOI of 0.1, survival rates were 40 and 38%, respectively.

Figure 4A:
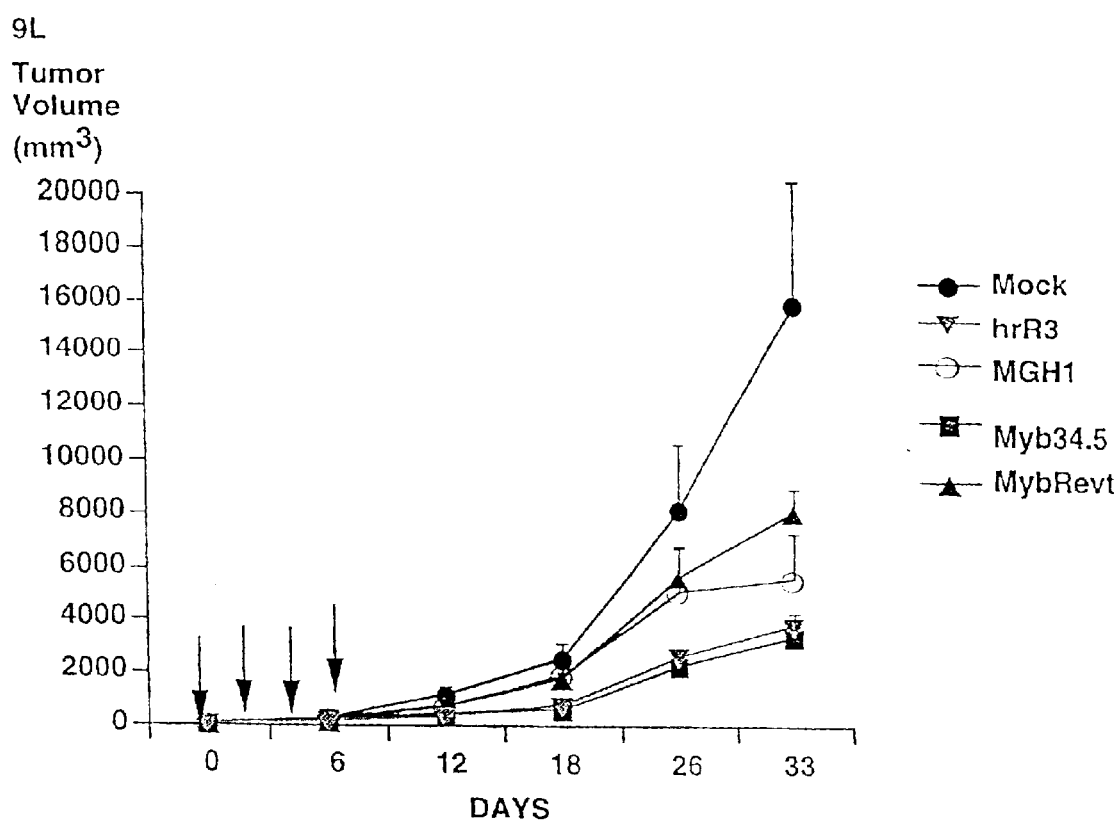
FIGS. 4A and 4B depict in vivo growth inhibition by Myb34.5. In similar experiments, rat gliosarcoma 9L (FIG. 4A) and human U87ΔEGFR glioma (FIG. 4B) cells were implanted subcutaneously into the flanks of nude mice. Beginning fourteen (9L) and ten (U87) days later (day 1), vehicle or mutant viral strains were inoculated intratumorally into tumors. Arrows indicate the times of viral injection (days 1, 3, 5, 7), while values are the averages of five mice per group (9L) and six per group (U87ΔEGFR).

In vivo anticancer effects—The in vivo anticancer effects of Myb34.5 were then determined. After establishing rat 9L gliosarcoma (FIG. 4A) or human U87dEGFR glioma (FIG. 4B) tumors in the flanks of athymic nice, intraneoplastic inoculation with each virus was performed. 9L tumor growth, as assessed by mean tumor volumes, was significantly reduced by Myb34.5 treatment compared to control animals, with inhibition quantitatively similar to that after hrR3 treatment (FIG. 4A). For U87ΔEGFR, a human glioma which expresses a common truncated EGF receptor (Nagane, M., et al., *Cancer Res.* 56:5079–5086 (1996); Huang, H. S., et al., *J. Biol. Chem.* 272:2927–2935 (1997); Nishikawa, R., et al., *Proc. Natl. Acad. Sci. USA* 91:7727–7731 (1994)), all strains significantly inhibited growth, with hrR3 and Myb34.5 producing 3 of 6 complete regressions, while MGH1 and MybRevt produced 2 of 6 regressions (to no visible tumor, FIG. 4B).

Figure 4B:
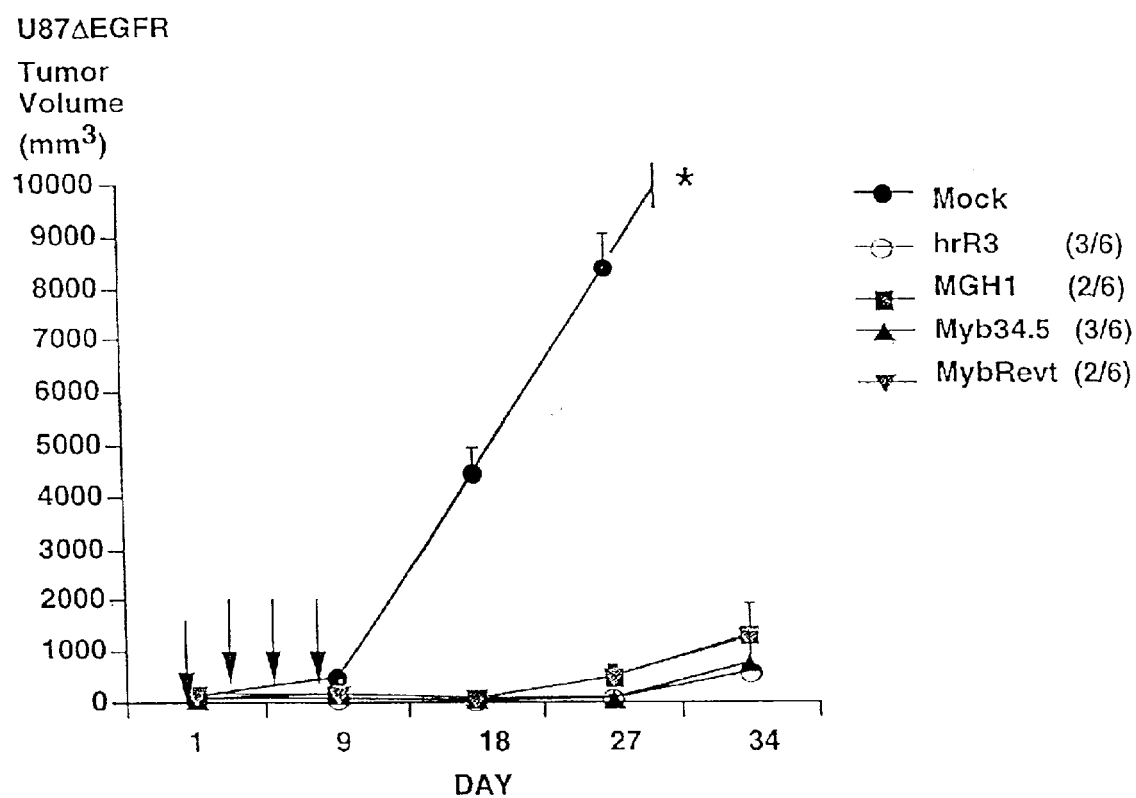

Although a cursory analysis of FIG. 4B may lead to the conclusion that there were no significant differences in the growth of human U87ΔEGFR tumors treated with the γ34.5 mutants (MGH1 and MybRevt) versus the γ34.5+viruses (hrR3 and Myb34.5), review of the actual tumor volumes at the 34-day point does reveal the presence of a significant difference (Table 4). These results thus showed that Myb34.5's in vivo oncolytic effects paralleled those of the single RR mutant and were superior to those of the γ34.5 mutants.

TABLE 4

Volumes of human U87ΔEGFR tumors after treatment[a]

| | | Tumor vol (mm³) after: | | | |
|---|---|---|---|---|---|
| | Mock | Infection with viral mutant | | | |
| Animal no. | infection | HrR3 | MGH1 | Myb34.5 | MybRevt |
| 1 | 11,880 | 0 | 3,960 | 4,000 | 221 |
| 2 | 19,530 | 32 | 0 | 0 | 561 |
| 3 | 15,592 | 15 | 0 | 132 | 0 |
| 4 | 10,626 | 0 | 1,300 | 0 | 3,420 |
| 5 | 10,584 | 0 | 1,914 | 0 | 3,344 |
| 6 | 15,620 | 3,366 | 900 | 405 | 0 |
| Median[b] | 13,736 | 7.5 | 1,100 | 66 | 391 |
| Confidence range (25–75%) | 10,626–15,620 | 0–32 | 0–1,914 | 0–405 | 0–3,344 |

[a]Details of experimental procedures are provided in the legend to FIG. 4. Results are from the 34-day time point.
[b]The differences in the median values among the treatment groups were statistically different (P = 0.004 [Kruskal-Wallis one-way analysis of variance on ranks]).

Discussion

In this Example, it has been demonstrated that the targeted double mutant HSV strain, Myb34.5, effectively killed malignant glioma cells both in vitro and in vivo, while retaining a high degree of safety in terms of neurotoxicity on direct intracranial inoculation in mice. This strain also exhibited minimal replication in primary arrested fibroblasts and marked induction of replication in cycling cells, similar to the induction seen with an HSV characterized by a single RR mutation. In tumor cells, it also replicated vigorously, with improved oncolytic efficacy compared to the parental double RR/γ34.5 mutant, MGH I. This is relevant as MGH1 and other γ34.5 mutants may have limited efficacy due to the lower viral yields obtained from infected cells (Kramm, C. M., et al., supra). Perhaps most importantly, Myb34.5, like MGH1 or other γ34.5 mutants, demonstrated little pathogenicity in mice at intracerebral doses of 107 PFU, remaining neuroattenuated. Therefore, Myb34.5 exhibits improved oncolytic efficacy compared to the parental mutant MGH1, the marker-rescued revertant MybRevt, and MGH1's parental mutant R3616, while maintaining characteristics of neuroattenuation, with an $LD_{50}$ of >10' PFU. This value is qualitatively similar to those observed with γ34.5 mutants, although strict quantitative comparisons were limited by the technical inability to accurately determine an $LD_{50}$ for the latter group of mutants.

A major objective in cancer gene therapy is to identify viral mutants, that provide significant anticancer effects while at the same time demonstrating minimal side effects and toxicity towards normal cells and tissues. This feat has been accomplished by engineering replication-defective viral vectors, which should display minimal toxicity toward infected normal and tumor cells, and endowing them with the ability to express anticancer genes to achieve biologic effects (Moriucbi, S., et al., *Cancer Res.* 58:5731–5737 (1998)). When applied as inocula to large human tumor masses, such vectors do not diffuse well due to their size, thus limiting anticancer effects to cells located in proximity to the injection tract (Bobo, R. H., et al., *Proc. Natl. Acad. Sci. USA* 91:2076–2080 (1994); Puumalainen, A. M., et al., *Hum. Gene. Ther.* 9:1769–1774 (1998)).

One potential solution to this problem consists of the use of replication-conditional (oncolytic, replication-restricted) viral mutants that maintain the ability to replicate in a relatively selective fashion in tumor or mitotic cells while being restricted in their ability to replicate in normal cells. Such viral mutants would thus propagate from initially infected tumor cells to surrounding tumor cells, thus achieving a larger volume of distribution and enhanced anticancer effects. However, one might expect increased toxicity with these mutants. In order to minimize the potential toxicities associated with replication-conditional HSV-1, deletion of the endogenous γ34.5 genes has been shown to significantly limit or eliminate the risk of encephalitis or meningitis upon intracerebral injection in rodents (Chou, J., et al., *Science* 250:1262–1266 (1990); Markert, J. M., et al., *Neurosurgery* 32:597–603 (1993); Markovitz, N. S., et al., *J. Virol.* 71:5560–5569 1997)) and Aotus monkeys (Mineta, T., et al., *Nat. Med* 1:938–943 (1995)). Further, in a phase I clinical trial in humans afflicted with malignant brain tumors, this type of mutant has not shown evidence of ill effects (Maruza, R. L., *personal communication*).

One concern, however, is that complete elimination of endogenous γ34.5 function would also limit the anticancer effect of HSV. In published experiments, this limitation was shown for rat 9L gliosarcoma cells both in vitro and in vivo (Kramm, S., et al., *Hum. Gene Ther.* 8:2057–2068 (1997)). In the present Example, we also tested killing mediated by HSV mutants with deletions of the γ34.5 function (MGH1 and MybRevt) against a panel of five human glioma cell lines (Table 2). As expected, these mutants were relatively limited in their oncolytic efficacy, compared to the wild-type F strain. Similar findings were also observed with R3616, MGH1's parental strain (Qureshi, N. and Chiocca, E. A., unpublished data). However, the oncolytic efficacy of MGH1 was restored to levels that were closer to those observed with the wild-type F strain upon insertion of a single γ34.5 gene under B-Mb promoter control.

The significance of this result is that inoculation of Myb34.5 into tumors is expected to produce more extensive oncolysis than inoculation of MGH1, R3616, or other γ34.5 mutants into tumors.

In fact, the antitunor efficacy of Myb34.5 in vivo was found to be quantitatively similar to that of a single RR mutant (hrR3), suggesting that in tumor cells, active expression of the γ34.5 product returns Myb34.5 to a γ34.5-positive phenotype. However, because hrR3 is a simple insertional mutant, Myb34.5 offers the theoretical advantage of being less prone to recombinatorial repair to wild-type in the presence of latent pre-existing, or subsequent HSV infection. Even in the unlikely event that repair of the ICP6 locus via homologous recombination might occur, the B-myb/γ34.5 insert would be excised and return Myb34.5 to the γ34.5 deleted genotype of R3616, the parental virus for MGH1.

Published results have demonstrated that at last one function of γ34.5 is to preclude the host cell's response to viral infection, namely, the triggering of host protein synthesis shutoff in an apoptosis-like response (Chou, J., et al., *Proc. Natl. Acad. Sci. USA* 92:10516–10520 (1995); Chou, J., et al., *Science* 250:1262–1266 (1990); Chou, J. and Roizman, B., *Proc. Natl. Acad. Sci. USA* 89:3266–3270 (1992)). A similar function is widespread among pathogenic viruses (Cosentino, G. P., et al., *Proc. Natl. Acad. Sci. USA* 92:9445–9449 (1995); Gale, M., et al., *Mol. Cell. Biol.* 18:5208–5218 (1998); Katze, M. G., *Trends Microbiol.* 3:75–78 (1995); Sharp, T. V., et al., *Nucleic Acids Res.* 21:4483–4490 (1993)). While γ34.5 is nonessential for viral growth in culture in Vero cells, it enables the virus to spread in the mouse central nervous system (Kesari, S., et al., *J. Gen. Virol.* 79:525–536 (1998); Kesari, S., et al., *J. Neurosci.* 16:5644–5653 (1996); Markovitz, N. S., et al., *J. Virol.* 71:5560–5569 (1997)) and maps to a region of the HSV genome previously implicated in CNS replication (Centifanto-Fitzgerald, Y. M., et al., *J. Exp. Med* 155:475–489 (1982); Markovitz, N. S., et al., *J. Virol.* 71:5560–5569 (1997)). This may be due to the fact that the γ34.5-encoded protein inhibits the double-stranded RNA-dependent kinase. On exposure to double-stranded RNA molecules, as seen commonly with viral infection, RNA-dependent kinase phosphorylates the alpha subunit of elongation initiation factor 2, resulting in inhibition of protein synthesis (Chou, J., et al., *Science* 250:1262–1266 (1990); Chou, J., et al., *J. Virol.* 68:8304–8311 (1994); Chou, J. and Roizman, B., *Proc. Natl. Acad. Sci. USA* 89:3266–3270 (1992)). Infection of cells of neuronal origin with mutants incapable of expressing γ34.5 results in shutoff of cellular protein synthesis, with the resultant limitation of viral production.

One critical aspect of the present study was to show restoration of γ34.5 function by B-myb promoter transcriptional control. This was done by demonstrating that infection of cells with MGH1 and MybRevt resulted in suppression of protein synthesis, while protein synthesis was restored when Myb34.5 was the infecting virus. Further evidence for the novel B-myb transcriptional dependence of γ34.5 function to the cell cycle was provided by the lovastatin arrest experiments. These clearly showed that under growth arrest conditions, when B-myb transcriptional activity is minimal, titers of Myb34.5 were similar to those of MGH1 and MybRevt and dissimilar from those of the wild-type F strain and hrR3. However, when cells were serum stimulated, titers of Myb34.5 increased by 3 orders of magnitude, approaching titers observed with strains F and hrR3, while titers of the γ34.5 mutants (MGH1 and MybRevt) increased only slightly. It was notable that the basal level of replication of Myb34.5 was lower than that of hrR3 in quiescent cells and was more quantitatively similar to that of the RRγ34.5 mutant MGH1. Myb34.5 demonstrated a higherfold induction of replication in cycling cells than hrR3, while MGH1 and MybRevt showed minimal induction, suggesting that the effects of the Myb34.5 construct exceed the effect a of simple complementation of ribonucleotide reductase.

These results confirm the hypothesis that the B-myb promoter restricts viral replication in quiescent cells and redirects viral replication to cycling cells. In the context of brain tumor therapy, Myb34.5 would thus replicate at relatively low levels (similar to the levels observed with MGH1) in cells that are quiescent, but infection of dividing brain tumor cells would produce a significant increase in viral titers, thus providing a therapeutic advantage over MGH1 or other γ34.5 mutants. Infection of normal brain cells can occur with γ34.5 mutants (Kesari, S., et al., *J. Gen. Virol.* 79:525–536 (1998); Kesari, S., et al., *J. Neurosci.* 16:5644 5653 (1996); Markovitz, N. S., et al., *J. Virol.* 71:5560–5569 (1997)), and one would expect Myb34.5 action to mimic that of these mutants in quiescent infected neural cells. In fact, our in vitro and in vivo studies do show that Myb34.5 replication in cultured neurons and in the brains of mice is similar to that of the γ34.5 mutant viruses (MGH1, MybRevt, and R3616) and dissimilar from that of wild-type F strain and hrR3.

An alternative explanation may be that observed effects of Myb34.5 are due to the replacement of the two endogenous γ34.5 genes by a single γ34.5 gene, and by use of a promoter (B-myb) that is weaker than the endogenous HSV γ34.5 promoter, and whose characteristics of strict cell cycle regulation are disrupted in the context of the HSV genome. Although formal exclusion of this possibility would require extensive additional experimentation with mutant B-myb promoters, we believe that it remains unlikely in view of the current experimental data. If this explanation were true, then one would predict: (i) Myb34.5 replication in quiescent cells to be higher than that of γ34.5 deletion mutants because of low level expression of the γ34.5 gene by a deregulated B-myb promoter in the former mutants; (ii) the inhibition of host protein synthesis shutoff observed in neuroblastoma cells infected with Myb34.5 (FIG. 2) to be less pronounced than that observed in cells infect with F or hrR3 because of lower expression of the single γ34.5 gene with a weaker promoter compared to the robust expression achieved by the two γ34.5 genes driven by the endogenous HSV promoter; (iii) the replication of Myb34.5 in U373 cells, known to severely restrict replication of γ34.5 mutants (Mohr, I. and Gluzman, Y., *EMBO J.* 15:4759–4766 (1996)), to also be somewhat restricted by the weaker expression of the γ34.5 gene in Myb34.5 compared to that of F or hrR3; and (iv) the differential in replication between quiescent and cycling cells to be higher for the hrR3 or F strain (expressing two copies of γ34.5 driven by the endogenous HSV promoter) than that for Myb34.5 (expressing one copy of γ34.5 driven by a deregulated B-myb promoter).

The experimental data in this Example does not agree with the aforementioned predictions. The most likely explanation for the observed results is that the B-myb promoter remains regulated in a relatively tight fashion even in the context of the HSV genome, thus leading to minimal, if any, expression of γ34.5 in quiescent cells and to levels of expression in cycling and tumor cells that appear functionally similar to those observed with viral strains with intact γ34.5 function.

It has recently been shown that HSV mutants can be engineered to function as vectors. This allows them to express not only viral oncolytic functions, but also additional anticancer effects, thereby increasing their therapeutic efficacy (Chase, M., et al., *Nat. Biotechnol.* 16:444–448 (1998)). Clearly, Myb34.5 may also provide a suitable backbone for the addition of anticancer genes, such as those that activate prodrugs. As tumor-selective promoters are identified, it would be relatively easy to use these to control expression of the γ34.5 gene or other virulence genes in order to further restrict viral production to tumor versus normal cells. The approach described here may also be used to restrict virulence to specific cell types in a tissue, by employing cell-specific promoters.

The B-myb promoter contains a consensus E2F binding site, is strictly regulated in cycling cells, and is in fact repressed in G. (Lam, E. W. and Watson, R. J., *EMBO J.* 12:2705–2713 (1993); Lam, E. W., et al., *Gene* 160:277–281

(1995); Bennett, J. D., et al., *Oncogene* 13:1073–1082 (1996)). A replication-defective adenovirus containing an E2F-responsive promoter has been used to demonstrate tumor-specific gene expression, relative not only to quiescent neuronal tissue but also to nontransformed normal cycling cells (Parr, M. J., et al., *Nat. Med* 3:1145–1149 (1997)). Alteration of some portion of the cell cycle regulatory p16/retinoblastoma/cdk4 pathway, which regulates E2F, appears to be a near universal event in human gliomas as well as many other tumor types, and provides an excellent substrate for targeting tumor specific expression of viral gene products (He, J., et al., *Cancer Res.* 54:5804–5807 (1994); Ueki, K., et al., *Cancer Res.* 56:150–153 (1996)).

Another HSV-1 mutant in which an albumin promoter was employed to regulate the expression of ICP4 toward hepatocytes has been described (Miyatake, S., et al., *J. Virol.* 71:5124–5132 (1997)). The primary difference from the strategy described in the present report is the use of a promoter that may be considered tumor or cell cycle specific instead of hepatocyte specific, and the use of an HSV gene that is directly related to virulence (γ34.5) rather than an essential transcription factor, such as ICP4. In contrast to many viral vectors under investigation for treatment of glioblastoma, the exemplified virus, designated Myb34.5, is replication competent, and targeted virulence is obtained by regulating viral replication and direct oncolysis. In this respect, Myb34.5 represents a novel, targeted oncolytic herpesvirus and adds to two recently described tumor-selective, oncolytic adeno- and reoviruses (Bischoff, J. R., et al., *Science* 274:373–376 (1996); Coffey, M. C., et al., *Science* 282:1332–1334 (1998)). The E1B-defective adenovirus ONYX-015 is thought to depend on alterations of the p53 tumor suppressor pathway for efficient replication in tumor cells, although this mechanism has recently been called into question (Goodrum, F. D., et al., *J. Virol.* 72:9479–9490 (1998)).

It has been shown that a reovirus strain selectively replicates in cells with an activated ras pathway (Coffey, M. C., et al., supra). Myb34.5 may take advantage of alterations of the p16/cdk4/RB/E2F pathway, and adds to the possibility that multiple tumor genetic alterations may be targeted by different viral treatment strategies. The strategy of using cell-specific or tumor-specific promoters to drive expression of the γ34.5 gene may also be suitable as a means to eliminate selected cell populations in vivo. Finally, the finding of increased safety combined with potent antitumor efficacy suggests that Myb34.5 is an excellent candidate for the treatment of malignant tumors.

EXAMPLE 2

(Peripheral Neoplasms)

Introduction

The vast majority of cancer gene therapy strategies for transgene delivery rely on genetically modified viruses (Rosenberg, S. A., et al., *Hum. Gene Ther.* 11:919–979 (2000); Roth, J. A. and Cristiano, R. J. *J. Natl. Cancer Inst.* 89:21–39 (1997)). These viruses have generally been engineered such that they are capable of replication only in special packaging cell lines and incapable of replication in humans. Antineoplastic activity is dependent on transgene delivery and expression. An alternative strategy relies on and exploits viral replication for tumor destruction. Infection of tumor cells by several types of viruses leads to cell destruction and simultaneous release of progeny virion that can infect adjacent tumor cells. The antineoplastic activity of viral oncolysis is dependent on the very efficient process of viral replication; however, it is critically important to maximize the ability of the virus to replicate in neoplastic cells (Chmura, S. J., *Radiat. Oncol. Investig.* 7:261–269 (1999)) and simultaneously minimize the ability of the virus to replicate in non-neoplastic cells.

Several viruses have been examined for their oncolytic activity including adenovirus (Bischoff, J. R., et al., *Science* 274:373–376 (1996); Kim, D., *Nat. Med.* 4:1341–1342 (1998)), herpes simplex virus (Martuza, R. L., *Science* 252:854–856 (1991)), vaccinia virus (Puhlmann, M., et al., *Cancer Gene Ther.* 7:66–73 (2000)), and reovirus (Coffey, M. C., et al., *Science* 282:1332–1334 (1998)). These viruses have been directly inoculated into tumors, which is an approach that has clinically significant drawbacks specifically for treatment of liver tumors in comparison to intravascular delivery. The first is that this approach requires direct visualization or radiographic imaging of the liver lesions. Both primary and secondary liver tumors are most commonly multifocal and a majority of patients with these tumors harbor numerous, undetectable foci of hepatic neoplastic cells (Zimmerman, A., "Tumours of the liver—pathological aspects," in *Surgery of the Liver and Biliary Tract, Blumngart*, L. H., ed., Churchill Livingstone: New York (1994), pp. 1277–1323). Even if technology were to evolve such that all hepatic tumor foci could be visualized, it is not feasible to accurately inject each malignant focus with an antineoplastic agent. The inability to precisely determine the boundary between malignancy and normal liver represents another drawback to a strategy that is dependent on direct intratumoral inoculation. The principal drawback to intravascular delivery is the requirement for the antineoplastic agent to possess greater selectivity to destroy tumor cells rather than normal cells. In the case of replication-competent viruses, this generally requires genetic engineering to restrict viral replication to neoplastic cells rather than non-neoplastic cells.

A very modest number of published reports describe the use of genetically engineered herpes simplex virus type 1 (HSV-1) for cancer therapy. These have generally involved direct intratumoral inoculation of mutant HSV-1 that are defective in expression of thymidine kinase (Martuza, R. L., *Science* 252:854–856 (1991)), ribonucleotide reductase (Mineta, T., et al., *Cancer Res.* 54:3963–3966 (1994); Yoon, S. S., et al., *FASEB J.* 14:301–311 (2000)), uracil-N-glycosylase (Pyles, R. B. and Thompson, R. L., J. Virol. 68:4963–4972 (1994)), or $\gamma_1 34.5$ (Andreansky, S. S., et al., *Proc. Natl. Acad. Sci. USA* 93:11313–11318 (1996)). It has been previously demonstrated that intravascular administration of an HSV-1 mutant that is defective in viral ribonucleotide reductase selectively targets and destroys diffuse liver metastases (Yoon, S. S., et al., supra). In this first-generation HSV-1 vector, the missing viral gene function (ribonucleotide reductase) is effectively complemented by liver metastases but not by normal liver, which results in viral replication in liver metastases rather than in normal liver. However, since viral ribonucleotide reductase function can theoretically be complemented by other actively dividing cell populations outside the liver, the inventors have concentrated their efforts on development and characterization of a second-generation HSV-1 vector whose replication is more tightly regulated and specific for cancer cells.

The inventors have constructed and described a second-generation replication-conditional HSV-1 vector, designated Myb34.5 (see Example 1 above; Chung, R. Y., et al., *J. Virol.* 73:7556–7564 (1999)), in which ribonucleotide reductase expression is defective and expression of the HSV-1 $\gamma_1 34.5$ gene is regulated by the cellular B-myb promoter (Lam, E. W., et al., *Gene* 160:277–281 (1995); Bennett, J. D., et al.,

*Oncogene* 13:1073–1082 (1996)). Following HSV-1 infection $\gamma_1 34.5$ normally interacts with the cellular protein phosphatase-1α, which leads to eIF-2a dephosphorylation (Chou, J., et al., *Science* 250:1262–1266 (1990); Chou, J. and Roizman, B., *Proc. Natl. Acad. Sci. USA* 89:3266–3270 (1992); He, B., et al., *Proc. Natl. Acad. Sci. USA* 94:843–848 (1997); He, B., et al., *J. Biol. Chem.* 273:20737–20743 (1998)). This allows initiation of protein translation to proceed, which is necessary for robust viral replication. HSV-1 mutants with completely defective $\gamma_1 34.5$ expression display significantly attenuated replication in both normal and neoplastic cells. In contrast, regulation of $\gamma_1 34.5$ expression by the cellular B-myb promoter following infection by Myb34.5 permits $\gamma_1 34.5$ expression in cycling cells and in cells with deregulated E2F activation (Chung, R. Y., et al., supra). Accordingly, Myb34.5 replication in tumor cells should be greater than that of HSV-1 mutants that are completely defective in $\gamma_1 34.5$ function. And Myb34.5 replication in quiescent cells should be as attenuated as that of HSV-1 mutants with completely defective $\gamma_1 34.5$ expression.

In this Example, the inventors have examined viral replication and cytolysis of hepatocytes and colon carcinoma cells infected with several HSV-1 mutants that differ in their expression of ribonucleotide reductase and $\gamma_1 34.5$. They have correlated replication of these mutants with their ability to induce eIF-2α dephosphorylation. B-myb regulation of $\gamma_1 34.5$ in Myb34.5 was associated with [i] greater eIF-2α dephosphorylation, viral replication, and cytolysis of colon carcinoma cells as compared to hepatocytes; [ii] destruction of diffuse liver metastases following intravascular delivery with prolonged survival of mice bearing diffuse liver metastases treated with Myb34.5; and [iii] viral replication limited to the sites of metastases.

Intravascular administration of Myb34.5 provided substantial reduction in liver tumor burden in mice with diffuse liver metastases, and this led to prolonged survival. Myb34.5 virulence was markedly attenuated compared to wild-type virus. Myb34.5 biodistribution following portal venous administration to mice bearing diffuse liver metastases was limited to the liver, whereas administration of wild-type HSV led to general viral dissemination. The presence of pre-existing antibodies to HSV did not reduce the anti-tumor efficacy of Myb34.5 in vivo. These results indicate that Myb34.5 holds promise as an effective agent for treatment of colon carcinoma diffuse liver metastasis.

Materials and Methods

Cells and Viruses—The Vero African Monkey kidney cells and HT29 human colon carcinoma cells were obtained from the ATCC (Manassas, Va.). MC26 mouse colon carcinoma cells were obtained from the National Cancer Institute Tumor Repository (Frederick, Md.). Cells were propagated in Dulbecco's Modification of Eagle's Medium (DMEM) with 8% fetal bovine serum (FBS), 100 U/nal penicillin, and 100 mg/ml streptomycin. Primary human and mouse hepatocytes were prepared as described (Yoon, S. S., et al., *Ann. Surg.* 228:366–374 (1998) (published erratum appears in *Ann. Surg.* 228(5) following table of contents). HSV-1 vectors F strain (wild-type HSV-1) and R3616 (defective $\gamma_1 34.5$ expression) (Chou, J., et al., *Science* 250:1262–1266 (1990)) were provided by Dr. Bernard Roizman (University of Chicago, Chicago Ill.). hrR3 (defective ICP6 expression) (Goldstein, D. J. and Weller, S. K., *Virology.* 166:41–51 (1988)) was provided by Dr. S. K. Weller (University of Connecticut, Conn.). Recombinant HSV-1 vectors Myb34.5 (defective ICP6 expression and $\gamma_1 34.5$ expression regulated by the B-myb promoter) and MGH1 (defective ICP6 and $\gamma_1 34.5$ expression) were constructed as described (Chung, R. Y., et al., *J. Virol.* 73:7556–7564 (1999); Kramm, C. M., et al., *Hum. Gene Ther.* 8:2057–2068 (1997)). Heat-inactivation of Myb34.5 was performed as described (Lelie, P. N., et al., *J. Med. Virol.* 23:297–301 (1987)).

Determination of eIF-2α Phosphatase Activity—The bacterial expression vectors pQE-eIF-2α and pGEX-PKR were provided by Dr. Bryan R. G. Williams (Lerner Research Institute, OH) (Cai, R. and Williams, B. R., *J. Biol. Chem.* 273:11274–11280 (1998)). *E. coli* BL21 cells, harboring the pQE-eIF-2α and pGEX-PKR expression vectors were grown overnight in 50 ml LB broth containing 50 µg/ml ampicillin. Following 1:10 dilution in fresh LB broth, cells were grown for 3 hours to an optical density of 0.8, at which time isopropyl-1-thio-β-D-galactopyranoside (IPTG) was added to a concentration of 1 mM for an additional 4 hours. Bacteria were pelleted and resuspended in modified NTEN (20 mM Tris-HCl, pH=7.6; 150 mM NaCl; 1 mM EDTA; 0.2 mM phenylmethylsulfonyl fluoride; 10 µg/ml aprotinin; 10 µg/ml leupeptin). Cells were lysed and sonicated, and lysates were centrifuged at 22,500×g at 4° C. for 20 minutes. To purify the His-tagged eIF-2α protein the supernatants of these lysates were incubated in a 50% Ni-NTA slurry (Qiagen Inc., Valencia, Calif.) at 4° C. for 60 minutes. The lysate-Ni-NTA mixture was loaded into a column and eluted with modified NTEN buffer including 250 mM imidazol. To purify the GST-PKR fusion protein the supernatant was incubated with glutathione-Sepharose beads (Amersham Pharmacia Biotech, Inc., Piscataway, N.J.) for 60 minutes at 4° C. and the lysate-glutathione-sepharose beads mixture was loaded into a column and eluted with buffer containing 50 mM Tris, pH=8.0; 1 mM EDTA; 10 µg/ml reduced glutathione. Purified eIF-2α protein (2 µg) was reacted with GST-PKR protein (2 µg) in 20 mM Tris-HCl, pH=7.5; 40 mM KCl; 2 mM $MgCl_2$, and $[\gamma^{32}P]ATP$ (5 Ci) in a final volume of 50 µl for 30 min at 32° C. to yield phosphorylated eIF-2α. HT29 cells and human hepatocytes were harvested 15 hours after mock infection or infection with 20 plaque-forming units (pfu) of HSV-1 F strain, Myb34.5, or MGH1 per cell and S10 fractions were prepared from these lysates, and diluted to a final volume of 15 µl with 20 mM Tris-HCl (pH=7.5), 50 mM KCl, 2 mM $MgCl_2$, and 0.1 mM EDTA. The amount of protein in each sample was quantified by BCA™ protein assay kit (Pierce, Rockford, Ill.) (He, B., et al., *Proc. Natl. Acad. Sci. USA* 94:843–848 (1997); Azrolan, N., et al., *J. Biol. Chem.* 270:19833–19838 (1995)). ATP was added to a final concentration of 0.8 mM. After 30 seconds at 32° C., each sample received 2 µl of eIF-2α-$^{32}$P and was reincubated at 32° C. The rate of dephosphorylation of eIF-2α-$^{32}$P was determined by placing 10 µl aliquots into a solution containing SDS at various time points, followed by electrophoresis on 10%–20% gradient gels. $^{32}$P remaining in eIF-2α-$^{32}$P was quantified by an image analyzer (ImageQuant™ Molecular Dynamics, Sunnyvale, Calif.) (Gross, M. and Kaplansky, D. A., *Biochim. Biophys. Acta* 740:255–263 (1983)).

Viral Replication and Cytotoxicity Assays—Viral replication assays were performed as described (Rice, S. A., et al., *J. Virol.* 67:1778–1787 (1993)). Briefly, 1×10$^6$ cells were infected with 2×10$^6$ pfu of virus for 2 hours, at which time unabsorbed virus was removed by washing with a glycine-saline solution (pH=3.0). The supernatant and cells were harvested 40 hours after infection, exposed to 3 freeze-thaw cycles to release virions, and titered on Vero cell monolayers. The results represent the mean of 3 independent experiments. Viral cytotoxicity assays were performed as described (Carroll, N. M., et al., *Ann. Surg.* 224:323–330

(1996)). Briefly, cells were plated onto 96-well plates at 5,000 cells per well for 36 hours. Virus was added at multiplicity of infection (moi) values ranging from 0.01 to 10 and incubated for 6 days. The number of surviving cells was quantitated using a colorimetric MTT assay and percent cell survival was calculated by comparison with the control (mock-infected) cells. Tests were performed in quadruplicate.

PCR Assay —PCR amplification of HSV-1-specific sequences was used to investigate the biodistribution of HSV-1 following administration to mice. Forward oligonucleotide primer 5'-GGAGGCGCCCAAGCGTCCGGCCG-3' (SEQ ID NO:1) and reverse oligonucleotide primer 5'-TGGGGTACAGGCTGGCAAAGT-3' (SEQ ID NO:2) were used to amplify a 229 bp fragment of HSV-1 DNA polymerase gene. For genomic DNA extraction, BALB/c mouse tissues were incubated in digestion buffer (10 mM Tris-HCl, pH=7.4; 5 mM EDTA; 0.5% SDS and 200 mg/ml proteinase K, pH=8.0) at 56° C. overnight. Following phenol and chloroform (1:1) extraction, DNA was precipitated in 70% ethanol and dried in a Speed-Vac Concentrator (Savant Instruments Inc., Farmingdale, N.Y.). DNA pellets were resuspended in distilled water and 0.1 $\mu$g of DNA was then subjected to PCR amplification. PCR reactions were performed in a 25 $\mu$l volume using rTth DNA polymerase per manufacturer instructions (Perkin-Elmer Applied Biosystems, Foster City, Calif.) with a DNA Thermal Cycler 480 (Perkin-Elmer Applied Biosystems) for 35 cycles of 95° C. for 1 min., 60° C. for 1 minute, and 72° C. for 1 minute Appropriate negative controls were used for all PCR reactions, and no contamination of reagents was detected.

Western Blot Analysis—Cell and liver tissue lysates containing equal amounts of protein as determined using the BCA™ Protein Assay (Pierce, Rockford, Ill.) were resolved by SDS-polyacrylamide gel electrophoresis on 4%–20% Tris-Glycine gels (Novex, San Diego, Calif.) and proteins were transferred to nitrocellulose membranes (Schleicher & Schuell, Keene, N.H.). Membranes were blocked with 10% nonfat milk overnight at 4° C. and then incubated with 5 $\mu$g/ml mouse anti-ribonucleotide-reductase mAb (MAB3033, Chemicon International, Inc. Temecula, Calif.) or anti-actin mAb (A5441, Sigma Chemical Co., St. Louis, Mo.) for 1 h. After washing 3 times, membranes were incubated with peroxidase-linked anti-mouse Ig (Amersham Pharmacia Biotech) diluted 1:4000 for 1 hour. Specific proteins were detected using ECL detection reagents following manufacture's instructions (Amersham Pharmacia Biotech).

Animal Studies—BALB/c and BALB/c nude mice were obtained from Charles River Laboratories, Inc. (Wilmington, Mass.). Animal studies were performed in accordance with policies of the Massachusetts General Hospital Subcommittee on Research Animal Care. To assess the therapeutic efficacy of HSV-1 against diffuse liver metastases, a single cell suspension consisting of $1\times10^5$ MC26 cells in 100 $\mu$l HBSS without $Ca^{2+}$ or $Mg^{2+}$ were injected into spleens of BALB/c mice, followed 3 days later by $5\times10^7$ pfu F strain, Myb34.5, heat-inactivated Myb34.5 in 100 $\mu$l media (n=6 per group). Mice were sacrificed 14 days after tumor implantation and the livers and spleens were weighed. To assess the survival improvement in HSV-1-treated mice, a separate experiment was performed in the same manner and the mice were instead followed for survival. The distribution of the intervals until death was determined by the method of Kaplan and Meier. To examine the therapeutic efficacy of HSV-1 in HSV-1-vaccinated mice bearing diffuse liver metastases, mice were vaccinated with $1\times10^7$ pfu KOS or Myb34.5 in 100 $\mu$l HBSS media by subcutaneous flank injection (Morrison, L. A. and Knipe, D. M., J. Virol. 68:689–696 (1994)). Control mice were vaccinated with HBSS. Two mice in each group were sacrificed after 28 days to collect serum for measurement of the presence of antibodies capable of neutralizing Myb34.5-mediated cytotoxicity against HT29 cells. This cytotoxicity assay was performed as described above, except Myb34.5 was incubated with one of the four mouse serum samples or HBSS for 30 minutes prior to dilution and application to HT29 cells. The remaining mice were injected with $1\times10^5$ MC26 cells into the spleen 25 days after vaccination, and then treated with an intrasplenic injection of $5\times10^7$ pfu Myb34.5 after 3 more days (n=6 per group). Mice were sacrificed 14 days after tumor implantation.

Statistical analysis—Two non-parametric statistical analyses, the log-rank test and Peto-Wilcoxon test, were used to compare survival between groups. Mean liver and spleen were compared using an unpaired two-tailed t-test (InStat, Graphpad Software, New York, N.Y.).

Results eIF-2$\alpha$ Phosphatase Activity in HSV-1-infected Cells— R3616 is a genetically engineered HSV-1 mutant derived from F strain and is defective in $\gamma_1$34.5 expression (Chou, J., et al., Science 250:1262–1266 (1990); Chou, J. and Roizman, B., Proc. Natl. Acad. Sci. USA 89:3266–3270 (1992)). MGH1 was derived from R36 16 and contains the $\beta$-galactosidase gene inserted into the ICP6 gene locus (Kramm, C. M., et al., Hum. Gene Ther. 8:2057–2068 (1997)), thereby disrupting expression of the large subunit of viral ribonucleotide reductase. Myb34.5 was derived from MGH1 and contains the HSV-1 $\gamma_1$34.5 gene under control of the E2F-responsive, cellular B-myb promoter.

In a previous study, it was demonstrated that SKNSH neuroblastoma cells infected with MGH1 shut off cellular protein synthesis, whereas, protein synthesis is not shut off in cells infected with either F strain or Myb34.5 (Chung, R. Y., et al., J. Virol. 73:7556–7564 (1999)). To better understand the mechanisms by which HSV-1 regulates protein synthesis in infected cells, eIF-2$\alpha$dephosphorylation was examined following viral infection. Although eIF-2$\alpha$is normally phosphorylated by PKR in response to HSV-1 infection, HSV-1 $\gamma_1$34.5 interacts with protein phosphatase-1$\alpha$ to dephosphorylate eIF-2$\alpha$to block the shut off of protein synthesis (see, FIG. 5). Proteins in the lysates of human HT29 colon carcinoma cells and human hepatocytes infected with F strain, Myb34.5, and MGH1 were examined for their ability to dephosphorylate eIF-2$\alpha$. Reaction of eIF-2$\alpha$-$^{32}$P with the S10 fraction cells or human hepatocytes infected with MGH1 or mock-infected resulted in minimal eIF-2$\alpha$ dephosphorylation (FIG. 6). And as expected, the S10 fraction of HT29 cells or human hepatocytes infected with F strain dephosphorylated eIF-2$\alpha$ significantly. Of importance, lysates prepared from HT29 cells infected with Myb34.5 significantly dephosphorylated eIF-2$\alpha$, whereas, lysates prepared from hepatocytes infected with Myb34.5 did not dephosphorylate eIF-2%. In HT29 cells, the eIF-2$\alpha$ phosphatase activity observed following infection with Myb34.5 was more than four-fold higher than that observed following infection with the $\gamma_1$34.5-deficient MGH1. In hepatocytes, the eIF-2$\alpha$ phosphatase activity observed following infection with Myb34.5 was similar to that of MGH1. It was concluded that $\gamma_1$34.5 regulation by the B-myb promoter in Myb34.5 is associated with significantly greater eIF-2$\alpha$ dephosphorylation in H19 cells than in hepatocytes.

Viral Replication—It was previously demonstrated that hrR3 (ICP6 defective) is several log orders greater in human colon carcinoma cell metastases as compared to normal liver cells (Yoon, S. S., et al., FASEB J. 14:301–311 (2000)). This pattern of hrR3 replication is associated with significantly higher levels of cellular ribonucleotide reductase in colon carcinoma cells as compared to hepatocytes. Presumably, compared to hepatocytes, colon carcinoma cells have higher levels of dideoxynucleotides, which effectively complement the absence of viral ribonucleotide reductase in hrR3. Myb34.5 is similar to hrR3 in its absence of ICP6 expression. In addition, it has been engineered such that its expression of $\gamma_1 34.5$ is regulated by the E2F-responsive, B-myb promoter. The pattern of eIF-2α dephosphorylation that we observed in colon carcinoma cells versus hepatocytes following infection with Myb34.5 suggests that $\gamma_1 34.5$ regulation provides an additional mechanism to achieve preferential replication in carcinoma cells compared to normal hepatocytes.

Figure 7:
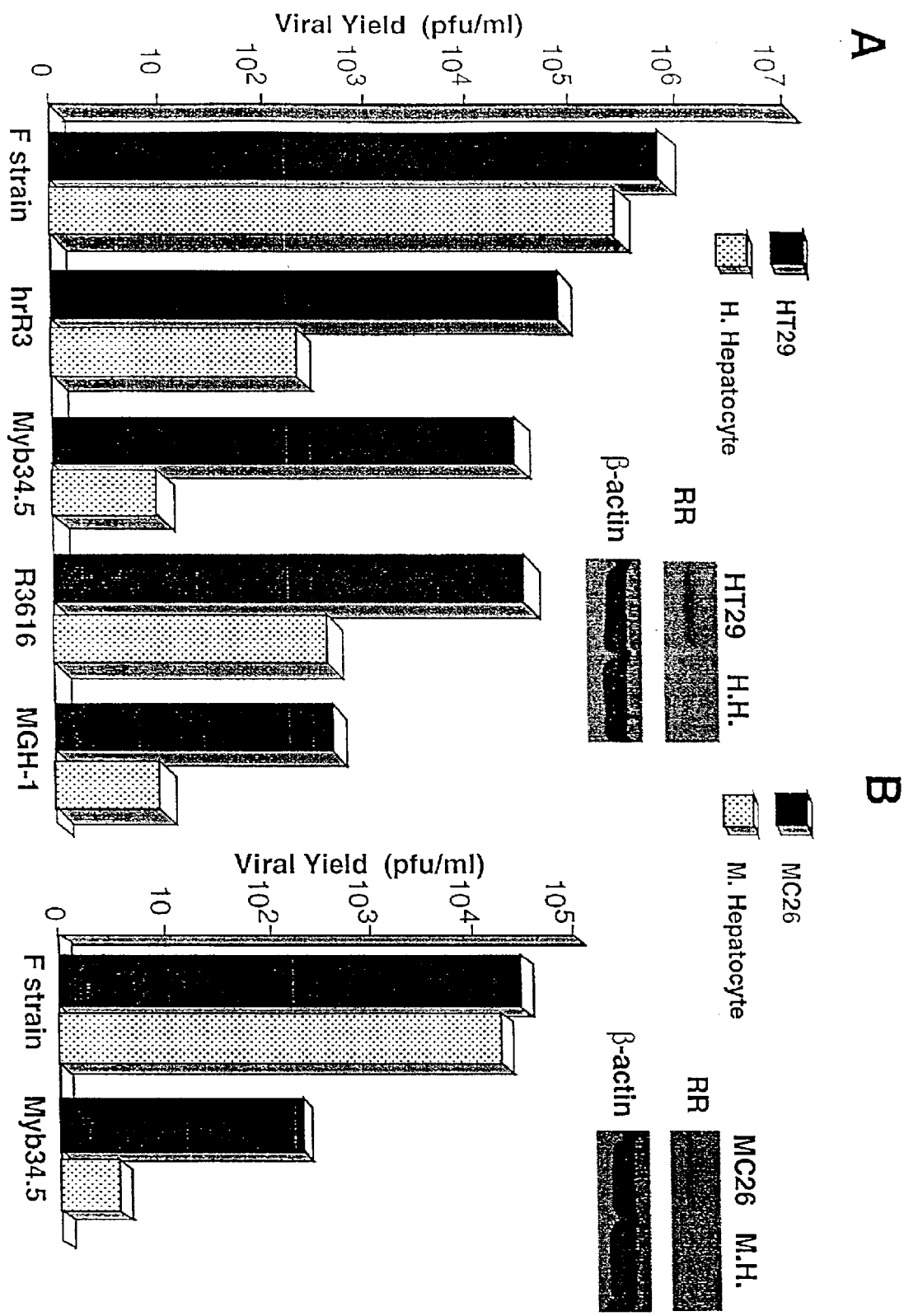
FIGS. 7A and 7B are bar graphs depicting replication of HSV-1 mutants in colon carcinoma cells and hepatocytes.

The correlation between $\gamma_1 34.5$ function in HSV-1-infected cells and viral replication was therefore examined. The number of infectious virion produced 40 hours after infection of Myb34.5 was compared with that of F strain, hrR3, R3616, and MGH1 in HT29 human colon carcinoma cells and human hepatocytes. Myb34.5 infection of HT29 cells yielded 10,000-fold more infectious progeny virion than did infection of human hepatocytes (FIG. 7A). In contrast, the number of infectious virion measured following infection by F strain was nearly identical in HT29 cells and hepatocytes. Furthermore, Myb34.5 replication was similar to that of hrR3 or R3616 in the colon carcinoma cells, but more than ten-fold less than that of hrR3 or R3616 and identical to MGH1 in the human hepatocytes. The replication of Myb34.5 and F strain was also compared in MC26 mouse colon carcinoma cells and primary hepatocytes. As observed in the human system, Myb34.5 replication was only one log order less than F strain in the colon carcinoma cells, but four log orders less in the hepatocytes (FIG. 7B). HSV-1 displays tropism for human and primate cells relative to murine cells, which results in lower levels of viral replication overall in the murine cells as compared to human cells. Nonetheless, the same pattern of Myb34.5 replication was observed in the murine tissue system as was observed in the human tissue system. From these data, the inventors concluded that [i] Myb34.5 replication is several log orders greater in colon carcinoma cells than hepatocytes in vitro; [ii] Myb34.5 replication in colon carcinoma cells is as robust as that of the single mutants hrR3 and R3616; [iii] Myb34.5 replication in hepatocytes is as attenuated as that of the double mutant MGH1; and [iv] the differential pattern of Myb34.5 replication in hepatocytes versus carcinoma cells observed in human cells is similar, but attenuated in murine cells.

Figure 8:
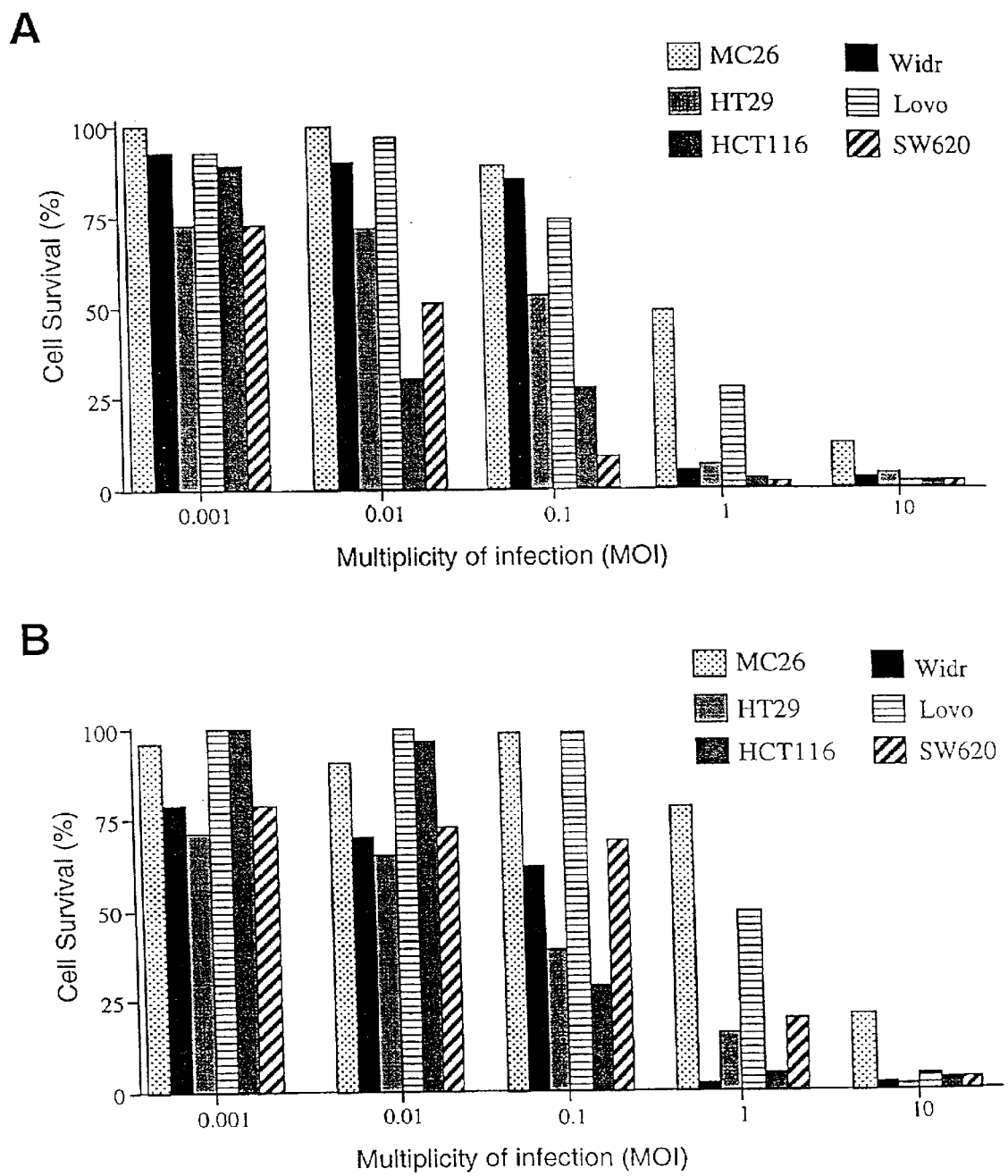
FIGS. 8A and 8B are bar graphs depicting cytotoxicity assays in vitro. Five human colon carcinoma cell lines and MC26 mouse colon carcinoma cells were infected with F strain (FIG. 8A) or Myb34.5 (FIG. 8B) using several moi values, and surviving sells were quantitated 6 days later using MTT.

Viral Cytopathic Effects in vitro—To examine the potential for therapeutic oncolysis, it was investigated whether Myb34.5 replication is associated with cytopathic effects. The cytopathic effect of Myb34.5 and F strain infection of five human and one murine colon carcinoma cell lines in vitro were quantitated. The cytopathic effect of Myb34.5 was nearly identical to that of wild-type F strain (FIG. 8). As expected, mouse colon carcinoma cells were slightly less susceptible to the cytopathic effects of Myb34.5 and F strain.

Figure 9A:
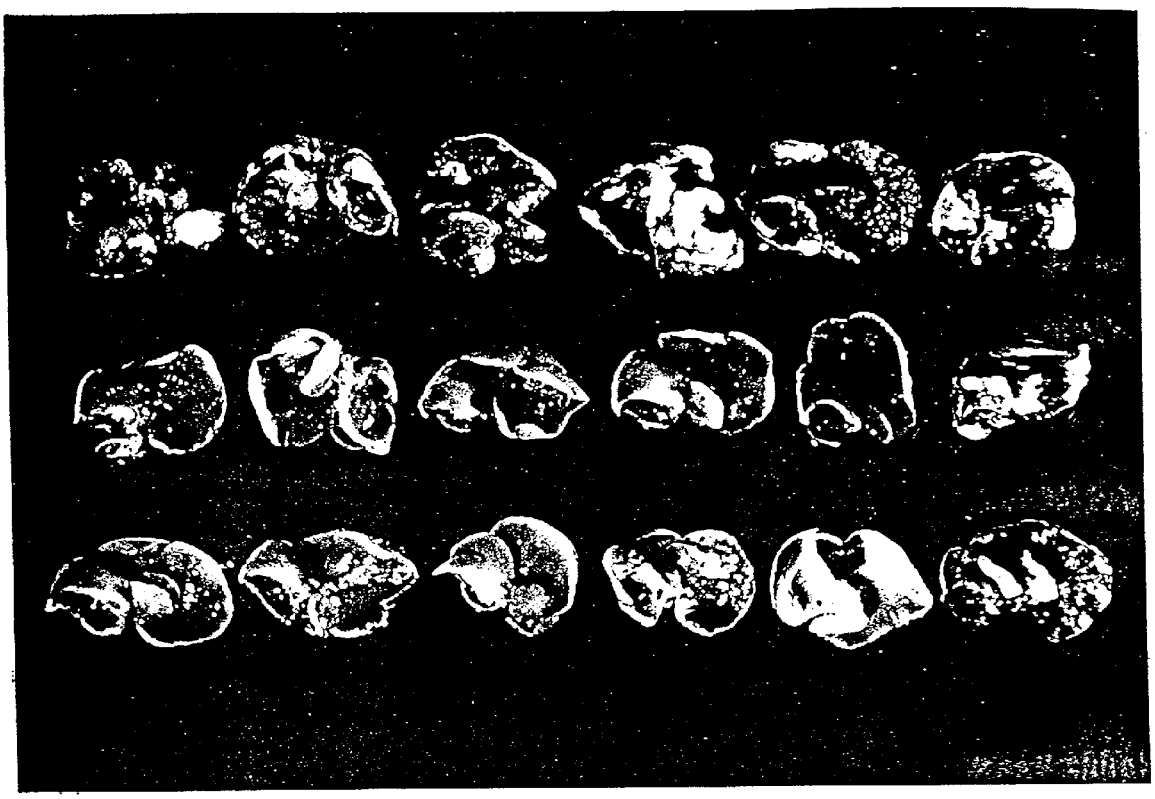
FIGS. 9A and 9B depict the treatment of diffuse liver metastases with Myb34.5.
Figure 9B:
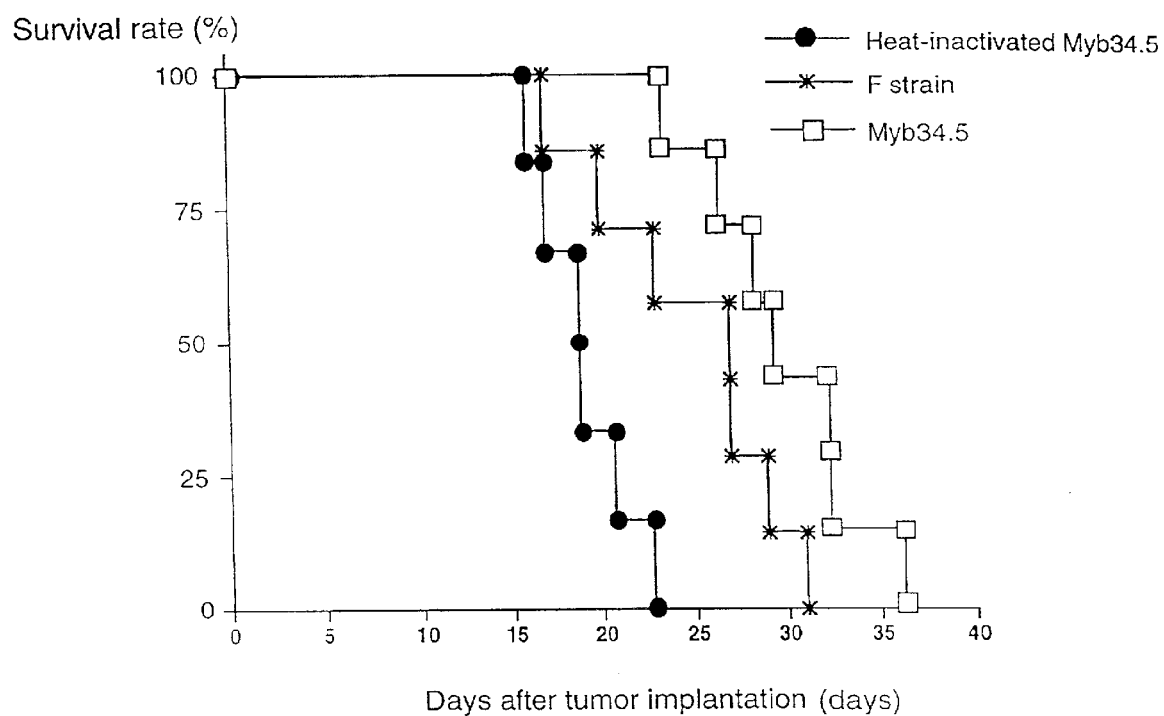

Oncolysis of Diffuse Colon Carcinoma Liver Metastases—It was previously demonstrated that a mutant HSV-1 defective in ICP6 replicates selectively within liver metastases rather than normal liver following intraportal administration (Yoon, S. S., et al., (1998), supra). In vitro experiments with Myb34.5 suggest that it too would selectively replicate within metastases rather than normal liver following intravascular delivery. Accordingly, the antitumor efficacy of Myb34.5 against diffuse experimental liver metastases was examined. Balb/c mice bearing syngeneic MC26 diffuse liver metastases were treated with a single portal venous injection of $5 \times 10^7$ pfu of Myb34.5, F strain, or heat-inactivated Myb34.5. At the time of animal sacrifice two weeks later, mice in the control group had distended abdomens with bloody ascites. In contrast, mice injected with Myb34.5 or F strain appeared healthy and had no ascites. Livers of mice in the control group contained numerous (greater than 50) tumor nodules, whereas, livers of mice treated with either Myb34.5 or F strain contained 5 or fewer nodules (FIG. 9A). The liver weights in Myb34.5-treated mice were significantly less than those of the control group mice (Table 5, Group A). There was no statistical difference in spleen weights among these three groups (Table 5, Group A), indicating that the reduction in liver tumor burden did not result from reducing splenic tumor burden. In a separate experiment, it was investigated whether these striking antitumor effects translate to improved survival in the Myb34.5-treated mice. Separate groups of mice were treated similarly and followed for survival. Myb34.5-treated mice demonstrated enhanced survival as compared to control mice (p<0.01). There was no statistically significant difference in survival between mice treated with Myb34.5 and mice treated with F strain (FIG. 9B); however, liver weights at the time of death were greater in F-strain-treated mice than in Myb34.5-treated mice (Table 5, Group B). Mice were treated with only a single administration of Myb34.5. Because tumor implantation and subsequent treatment each require a laparotomy, it is not feasible to perform a third laparotomy to administer a second dose of Myb34.5.

TABLE 5

Liver and spleen weights following treatment of MC26 liver metastases

| Group | Treatment | Immunization | n | Liver weight (g) + SD | Spleen Weight (g) + SD |
|---|---|---|---|---|---|
| A | F strain | None | 6 | 1.93 ± 0.24$^a$ | 0.72 ± 0.24$^d$ |
|   | Myb34.5 | None | 6 | 2.02 ± 0.26$^a$ | 0.59 ± 0.19$^d$ |
|   | Mock | None | 6 | 2.62 ± 0.34 | 0.94 ± 0.39 |
| B | F Strain | None | 4 | 2.22 ± 0.68$^b$ | ND |
|   | Myb34.5 | None | 4 | 1.57 ± 0.38$^b$ | ND |
|   | Mock | None | 4 | 3.89 ± 1.28 | ND |
| C | Myb34.5 | Myb34.5 | 6 | 1.63 ± 0.28$^{c,e}$ | 0.37 ± 9,15$^f$ |
|   | Myb34.5 | Mock | 6 | 1.70 ± 0.19$^{c,e}$ | 0.40 ± 0.25$^g$ |
|   | Mock | Myb34.5 | 6 | 2.50 ± 0.80 | 1.07 ± 0.29 |

A. No immunization prior to tumor implantation. Livers and spleens were weighed 14 days after tumor implantation.
B. Livers were weighed at the time when mice were dead.
C. Immunization was performed 25 days prior to tumor implantation.
$^a$P < 0.05, compared to non-immunized mock (heat-inactivated virus) treatment.
$^b$P < 0.05, compared to Myb34.5-immunized mock treatment.
$^c$P < 0.05, compared to Myb34.5-immunized mock treatment.
$^d$P value not significant compared to non-immunized mock treatment.
$^e$P value not significant compared to non-immunized mock treatment.
$^f$P < 0.01, compared to Myb34.5 immunized mock treatment.
$^g$P < 0.05, compared to Myb34.5 immunized mock treatment.
ND, not determined.

Figure 10:
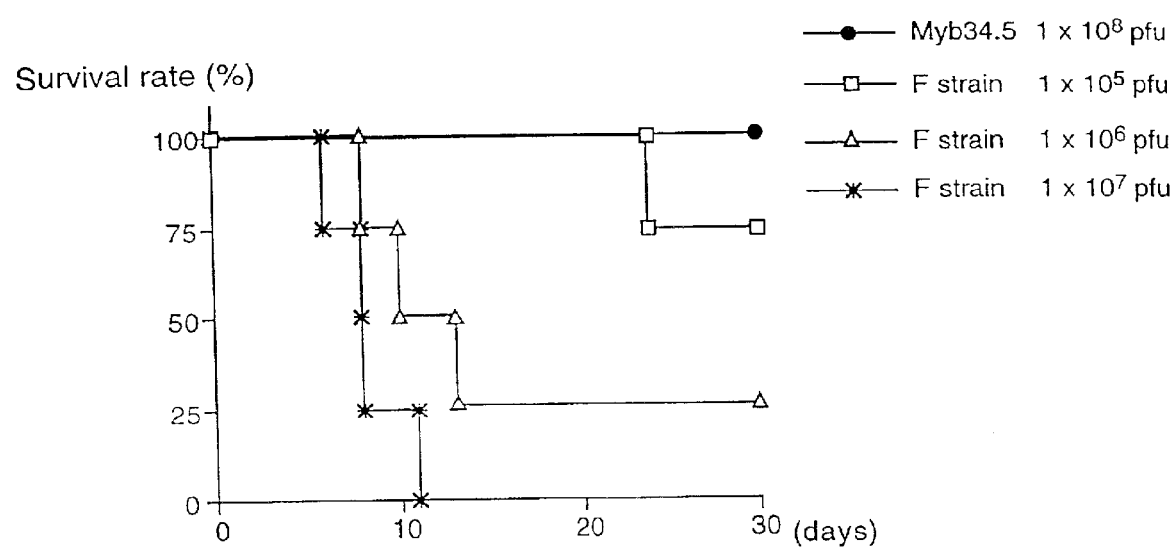
FIG. 10 is a graph depicting lethal doses of HSV-1 in BALB/c mice. Survival of mice injected subcutaneously with Myb34.5 virus or F strain was followed for 30 days.

Myb34.5 Toxicity and Biodistribution—No histochemical evidence of encephalitis was observed in any of the mice, and notably, the anti-tumor efficacy of F strain was similar to that of Myb34.5. However, the toxicity of F strain relative to Myb34.5 is better demonstrated by a model of subcutaneous injection. It was observed that following subcutaneous inoculation of $1\times10^7$ pfu of F strain, mice developed paralysis followed uniformly by death within 25 days. In contrast, no toxicity was observed following subcutaneous inoculation of $1\times10^7$ pfu of Myb34.5. To formally assess the viral toxicity after administration of Myb34.5, the $LD_{50}$ of mice treated with either Myb34.5 or F strain was examined. BALB/c mice were injected subcutaneously with increasing titers of F strain ($1\times10^7$ pfu, $1\times10^6$ pfu, or $1\times10^8$ pfu) or Myb34.5 ($1\times10$ pfu). The single dose of Myb34.5 that we examined represented the highest titer that we were able to produce in the laboratory. None of the mice injected with Myb34.5 died in 30 days, while all of the mice injected with $1\times10^7$ pfu F strain died within 11 days and 75% of mice inoculated with $1\times10^6$ pfu F strain died within 12 days (FIG. 10). These results are consistent with previous data that demonstrate a substantial reduction in neurovirulence of Myb34.5 compared to F strain following intracerebral inoculation into mice (Chung, R. Y., et al., *J. Virol.* 73:7556–7564 (1999)).

Figure 11:
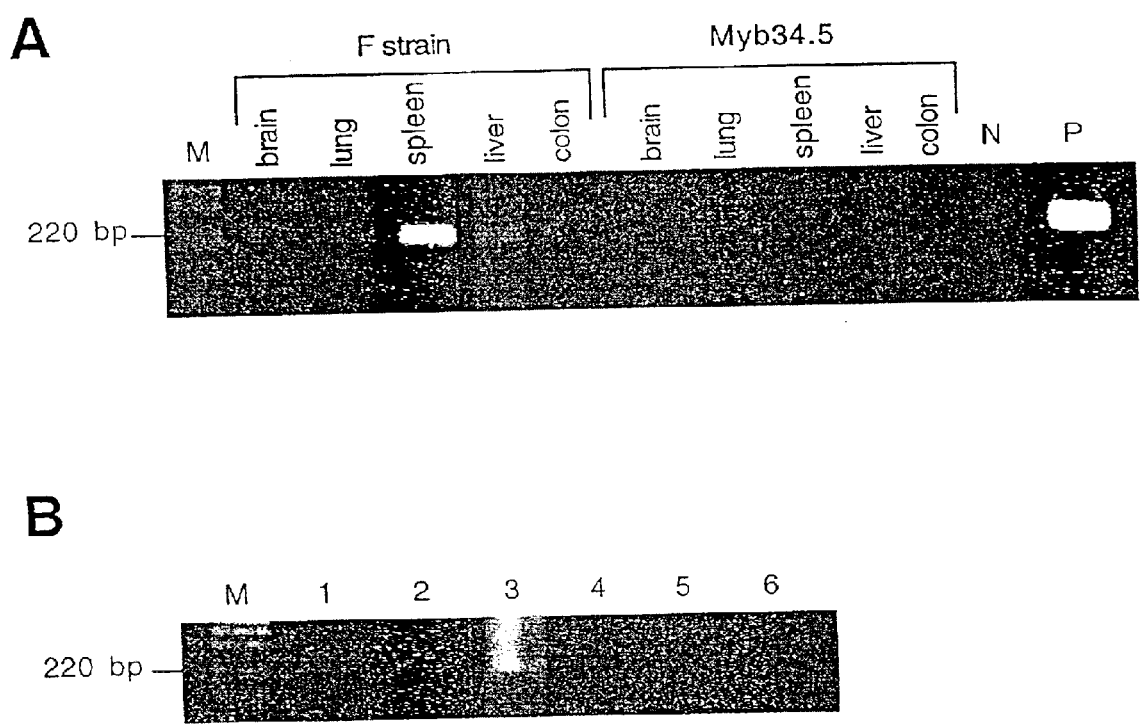
FIGS. 11A and 11B depict HSV-1 detection in mice by PCR assay.

Several mouse tissues were examined for the presence of HSV-1 DNA by PCR amplification of the HSV-1 DNA polymerase gene 8 days following subcutaneous administration of F strain and Myb34.5 to BALB/c mice. HSV-1 DNA was detected in all tissues examined (brain, lung, spleen, liver, colon) of the mice injected with F strain; however, it was not detected in any tissues of the mice injected with Myb34.5 (FIG. 11A). In a separate experiment, $1\times10^7$ pfu Myb34.5 was administered intrasplenically either to normal control mice or to mice bearing diffuse MC26 liver metastases 7 days following tumor implantation. All mice were sacrificed 10 days later and their organs were harvested and examined for the presence of Myb34.5. HSV-1 DNA polymerase was successfully amplified from livers of mice bearing diffuse liver metastases, but not from mice without liver tumors (FIG. 11B). HSV-1 DNA polymerase was not detectable in any other tissues in either mice with diffuse metastases or control mice. These results suggest that biodistribution of Myb34.5 is significantly more restricted than that of F strain, and appears to be limited to the livers with metastases 10 days following intraportal administration. Moreover, Myb34.5 appears to persist for a longer period of time in livers bearing metastases compared to normal livers.

Figure 12:
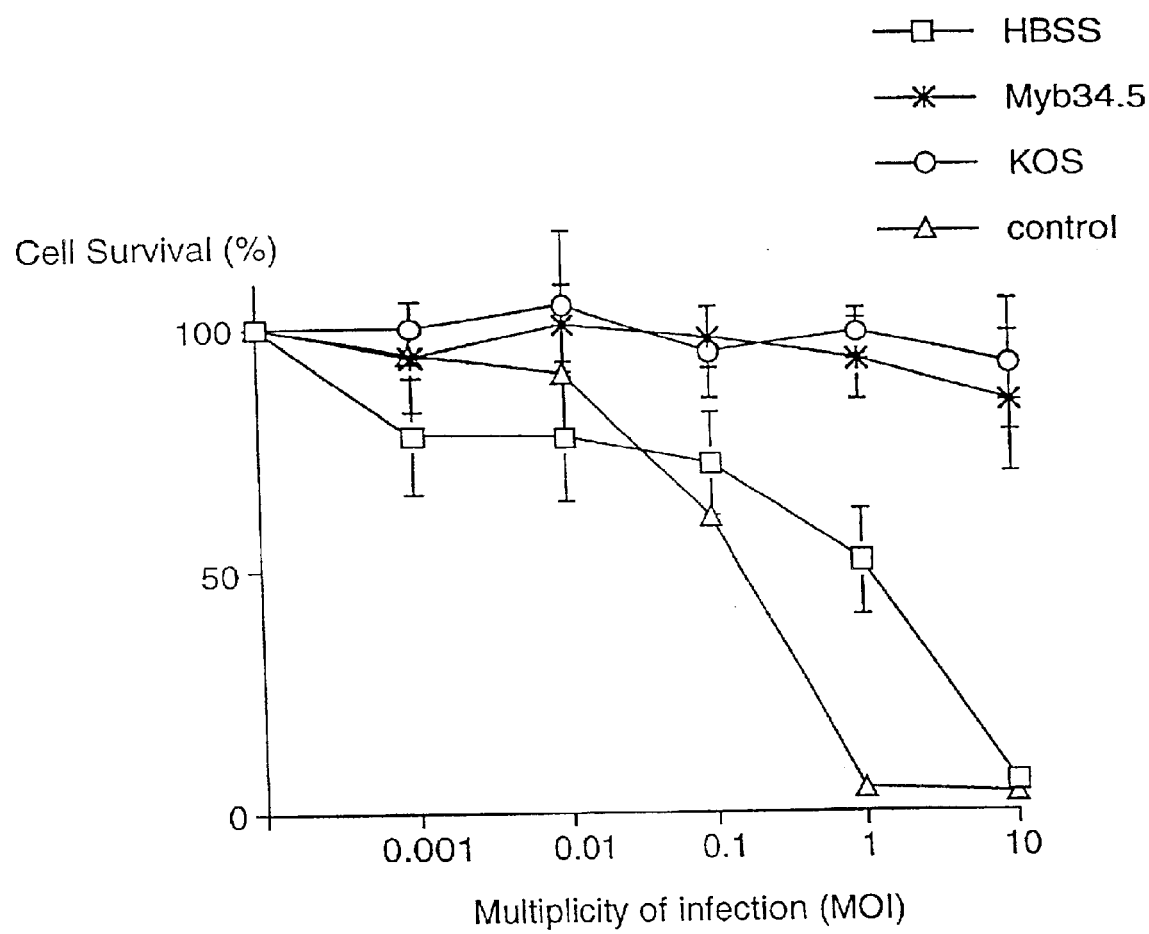
FIG. 12 is a graph depicting that sera from HSV-1-immunized mice neutralize Myb34.5. Myb34.5 was incubated with sera collected from mice immunized with either KOS, Myb34.5, or HBSS, and then added to HT29 cells using several moi values. As an additional control, Myb34.5 was incubated with media instead of sera before infecting HT29 cells (control).
Figure 13:
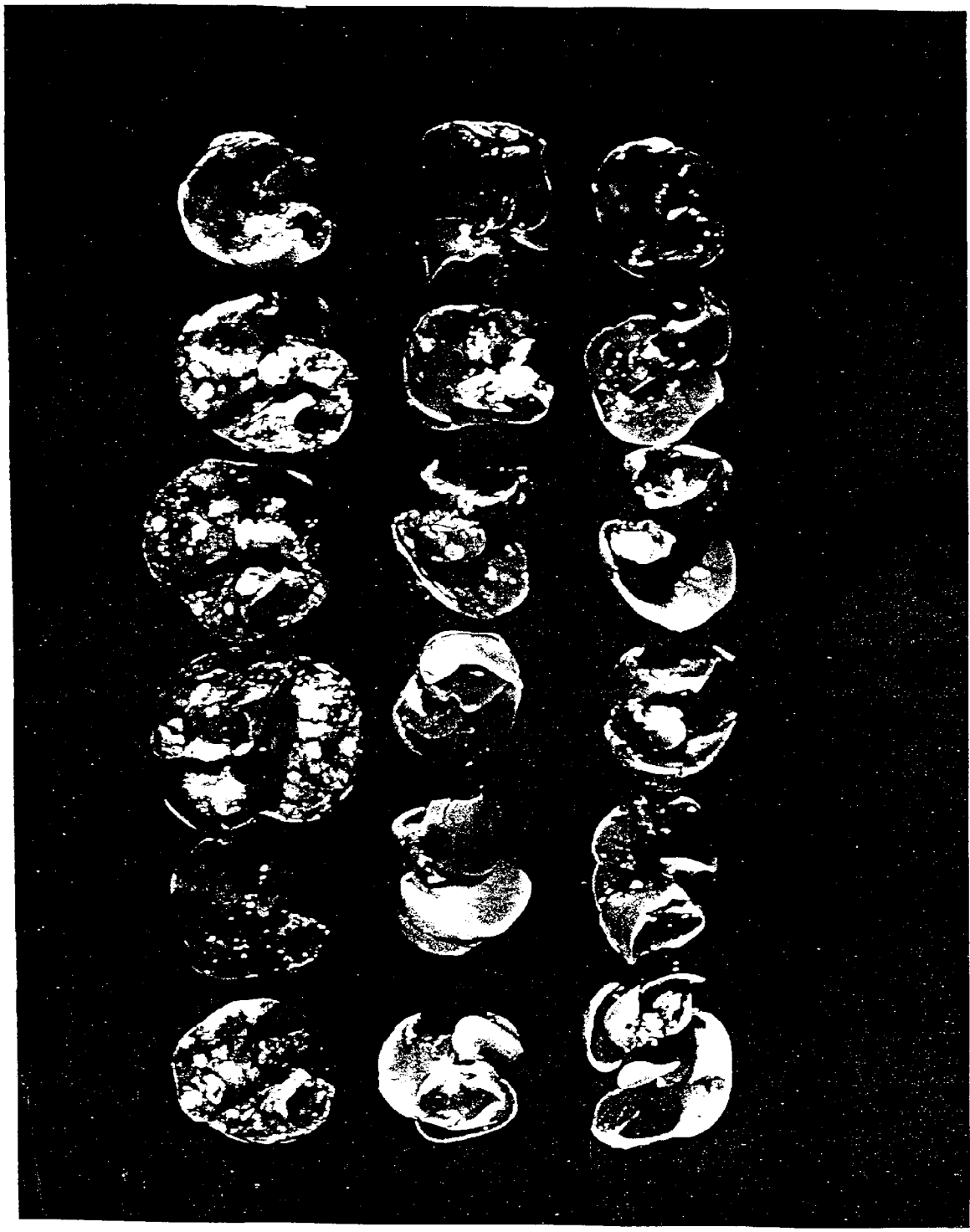
FIG. 13 depicts treatment of diffuse liver metastases with Myb34.5 in mice with neutralizing antibodies to HSV-1.

Host immune effects on Myb34.5-mediated oncolysis —HSV-1-mediated oncolysis may theoretically be influenced by host immune responses to the virus (Ikeda, K., et al., *Nat. Med* 5:881–887 (1999)). A large percentage of patients have antibodies to HSV-1 (Becker, T. M., et al., *Sex. Transm. Dis.* 23:138–144 (1996)), and the presence of these antibodies might decrease the efficiency of viral infection and oncolysis. On the other hand, it has been reported that the host immune response can enhance the antitumor effects of HSV-1-mediated oncolysis (Toda, M., et al., *J. Immunol.* 160:4457–4464 (1998); Toda, M., et al., *Hum. Gene. Ther.* 10:385–393 (1999)). Accordingly, it was then investigated how the presence of neutralizing antibodies affects Myb34.5-mediated oncolysis of diffuse liver metastases. Mice were subcutaneously vaccinated with mock-infected media, $1\times10^7$ pfu of KOS, or $1\times10^7$ pfu of Myb34.5. Two mice in each group were sacrificed after 28 days to collect serum for measurement of the presence of antibodies capable of neutralizing Myb34.5 cytotoxicity against HT29 cells. Sera from the mouse vaccinated with mock-infected media had little neutralizing effect, whereas, the sera from mouse vaccinated with either Myb34.5 or KOS significantly reduced Myb34.5-mediated cytotoxicity (FIG. 12). MC26 liver metastases were established in mice that had been vaccinated with either Myb34.5 or mock-infected media. The mice were then treated with a single portal venous injection with either Myb34.5 or mock-infected media. The mice were sacrificed 14 days after tumor implantation, and the livers examined. Livers from mice treated with a single portal venous injection of Myb34.5 had few tumor nodules (Table 5, Group C). The liver tumor burden in Myb34.5-treated mice was the same whether or not the mice had been vaccinated to produce neutralizing anti-HSV-1 antibodies. The liver tumor burden in these mice was substantially less than that of mice that had been treated with portal venous injection of mock-infected media rather than Myb34.5 (FIG. 13). These results indicate that pre-existing antibodies to HSV-1 neither enhances nor attenuates Myb34.5-mediated oncolysis.

Discussion

Viruses have developed mechanisms to efficiently infect cells, subvert cellular defenses, express viral genes, and produce progeny virion. Scientists have exploited these natural processes for purposes of therapeutic gene delivery, and genetically engineered viruses are presently the most commonly used gene delivery vehicles in clinical trials today (Rosenberg, S. A., et al., *Hum. Gene Ther.* 11:919–979 (2000); Roth, J. A. and Cristiano, R. J., *J. Natl. Cancer Inst.* 89:21–39 (1997)). Viruses that serve as simple gene delivery vehicles have been genetically crippled such that they are incapable of replication to minimize the risk of uncontrolled replication in the host. However, because viral replication results in tissue destruction, several investigators have examined strategies of injecting replication-competent viruses into tumors to destroy the tumors as a result of viral replication (Bischoff, J. R., et al., *Science* 274:373–376 (1996); Kim, D., Nat. Med. 4:1341–1342 (1998); Martuza, R. L., Science 252:854–856 (1991); Puhlmann, M., et al., *Cancer Gene Ther.* 7:66–73 (2000); Coffey, M. C., et al., *Science* 282:1332–1334 (1998); Kirn, D. H., *J. Clin. Invest.* 105:837–839 (2000)). The concept of viral inoculation to destroy was described nearly a century ago (Asada, T., *Cancer* 34:1907–1928 (1974)).

Oncolysis achieved by viral replication has several potential advantages compared to traditional cancer therapies. Viral replication within a tumor amplifies the administered dose, as tumor cells produce progeny virion that infect adjacent tumor cells. Cell-to cell propagation of virus enhances infection throughout the tumor. This is in contrast to intravascular delivery of traditional therapeutic agents, in which it has been observed that high interstitial pressures and dysregulation of tumor neo-vasculature combine to limit delivery of these agents to tumor cells (Jain, R. K., *Science* 271:1079–1080 (1996)). Another advantage of replication-competent viruses is their ability to serve dual roles: induction of oncolysis by viral replication and delivery of transgenes for added therapeutic efficacy (Freytag, S. O., et al., *Hum. Gene Ther.* 9:1323–1333 (1998)).

The safety of replication-competent viruses used in humans for cancer therapy remains of paramount importance, and these viruses should meet specific safety criteria. First, viral replication should be limited to neoplastic cells, with negligible if any replication in normal cells. Second, the potential for spontaneous reversion to a virulent strain should be minimized. Third, an effective antidote (antiviral agent) should be safe to administer and readily available if needed. Finally, the therapeutic window should be large, reflecting the difference between the dose at which toxicity is observed and the dose at which anti-tumor efficacy is observed.

The efficacy of hrR3 for treatment of diffuse liver metastases was previously demonstrated (Yoon, S. S., et al., *FASEB J.* 14:301–311 (2000)); however, hrR3 does not fulfill the criteria described above and is therefore not safe for examination in clinical trials. Its principal drawback is the potential for 1 reversion to a wild-type strain of HSV-1 by spontaneous elimination of the β-galactosidase gene. The hrR3 mutant is defective in ICP6 expression by virtue of disruption of the coding sequence by insertion of the β-galactosidase gene (Goldstein, D. J. and Weller, S. K., *Virology.* 166:41–51 (1988)). This is its only alteration from wild-type HSV-1 and none of the coding region of ICP6 has been deleted from hrR3. In contrast, Myb34.5 contains two major genetic alterations. Both copies of the wild-type $\gamma_1 34.5$ gene have been removed and much of the coding sequence of ICP6 has been removed. The $\gamma_1 34.5$ gene under the control of the B-myb promoter was introduced into the ICP6 locus (Chung, R. Y., et al., *J. Virol.* 73:7556–7564 (1999)). With multiple genetic alterations, the risk of spontaneous reversion of Myb34.5 to a wild-type virus is exceedingly low. In addition, Myb34.5 displays a larger therapeutic window than hrR3 as assessed by measurements of viral replication in colon carcinoma cells versus hepatocytes. And similar to other HSV-1 mutants that retain an active HSV-1 thymidine kinase gene, Myb34.5 retains its sensitivity to acyclovir, which is an effective therapeutic agent for HSV-1 infection in clinical use today (Brigden, D., et al., *Antiviral Res.* 1:203–212 (1981)).

Humans represent the only species that is naturally infected by HSV-1. Rodent cells are substantially more resistant to HSV-1 infection than are human cells (Huemer, H. P., et al., *Arch. Virol.* 130:353–364 (1993)). Although rodent models are suitable to examine anti-tumor efficacy of oncolytic HSV-1 vectors, they are not suitable for measuring toxicity relevant to that which may be observed in humans. Aotus (owl) monkeys are highly susceptible to herpes encephalitis, and have been accepted as the most suitable model for examining toxicity of oncolytic viruses derived from HSV-1 (Hunter, W. D., et al., *J. Virol.* 73:6319–6326 (1999)). Although it has been demonstrated that the $LD_{50}$ of Myb34.5 is at least two log orders greater than that of wild-type F strain in a mouse model, the relationship between dose-schedule and toxicity is more appropriately examined in Aotus monkeys. The observed biodistribution of Myb34.5 compared to F strain as assessed by PCR amplification provides additional evidence that Myb34.5 replication is highly specific for tumor-bearing liver, whereas DNA evidence of F-stain replication was detected in all of the tissues examined. The PCR assay is extremely sensitive and detects the presence of HSV-1 DNA. It is important to point out that the mere presence of HSV-1 DNA does not necessarily imply the presence of biologically relevant HSV-1 that is either infectious or latent.

PKR activation in response to viral infection remains an important cellular defense (Gale, M., Jr. and Katze, M. G., Pharmacol. Ther. 78:29–46 (1998); Jagus, R., et al., *Int. J. Biochem. Cell Biol.* 31:123–138 (1999)). The importance of this mechanism is underscored by the observation that most viruses have incorporated strategies to overcome the shutoff of protein translation that accompanies PKR activation. For example, adenovirus produces VAI RNA to associate with PKR to inhibit its activation (Ghadge, G. D., et al., *J. Virol.* 68:4137–4151 (1994)). Similarly, human immunodeficiency virus (HIV) produces TAR RNA which performs a similar function as VAI RNA (Park, H1., et al., *Proc. Natl. Acad. Sci. USA* 91:4713–4717 (1994)). $P58^{IPK}$ is an inhibitor of PKR that is constitutively expressed in mammalian cells and is normally inactivated by specific inhibitory molecules. Influenza virus disrupts this $P58^{IPK}$-inhibitory-molecule complex following infection, thereby functionally activating the PKR inhibitory activity of $P58^{IPK}$ (Lee, T. G., et al., *Mol Cell Biol* 14:2331–2342 (1994); Tang, N. M., et al., *J. Biol. Chem.* 271:28660–28666 (1996)). As another example, the E3L and NS5A proteins that are expressed by HCV are known inhibitors of PKR (Gale, M. J., Jr., et al., *Virology* 230:217–227 (1997); Davies, M. V., et al., *J. Virol* 67:1688–1692 (1993)).

Figure 5:
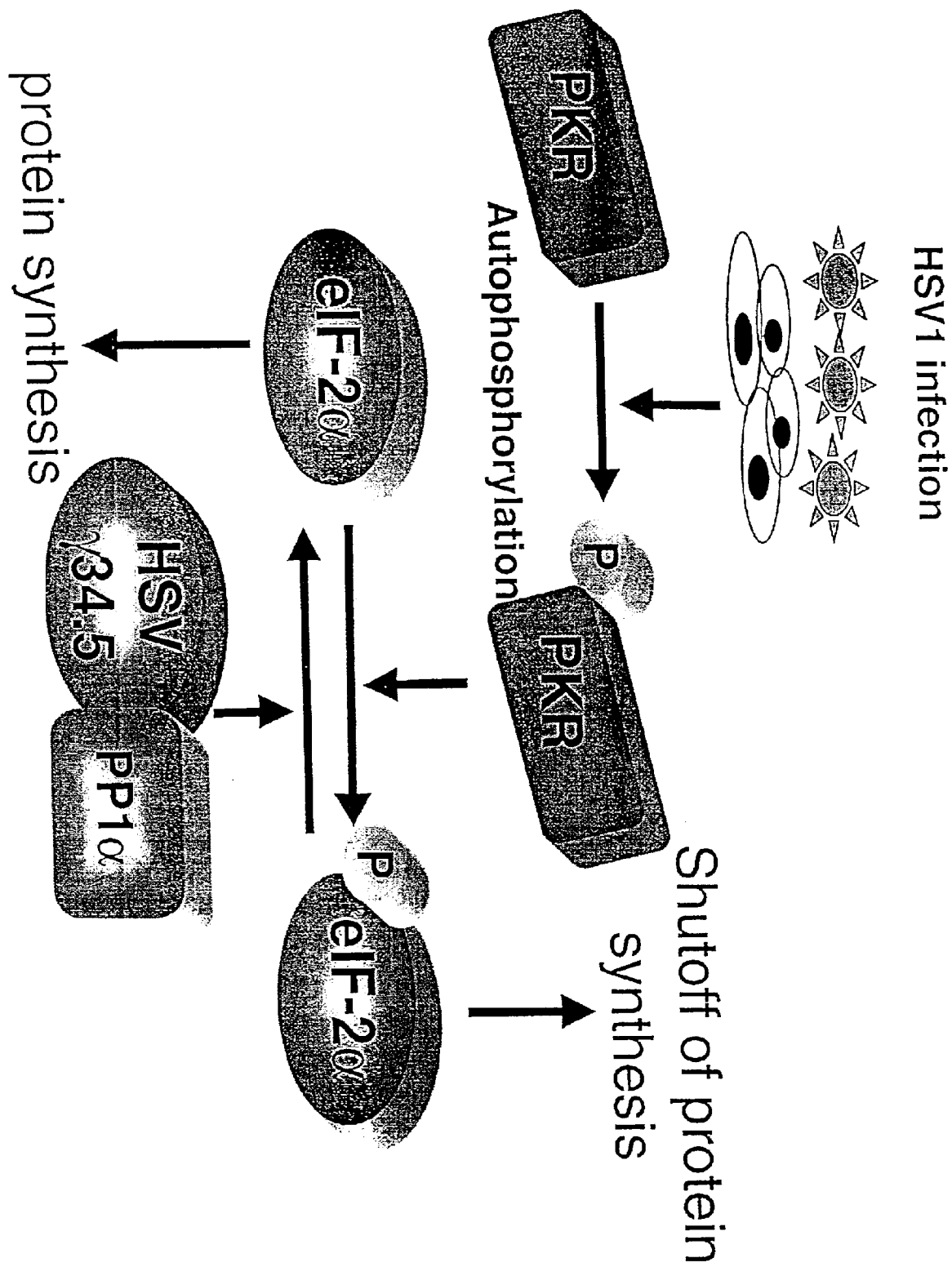
FIG. 5 is a schematic diagram showing the regulation of protein synthesis by γ34.5 in HSV-1-infected cells. Protein kinase R (PKR) recognizes viral double strand RNA and is subsequently activated by autophosphorylation. Activated (phosphorylated) PKR phosphorylates eIF-2α, which inhibits initiation of protein translation within the cell, and in turn inhibits viral replication. HSV-1 γ34.5 interacts with cellular protein phosphatase-1α (PP 1α) to dephosphorylate eIF-2α, thus allowing continued protein synthesis.
Figure 6:
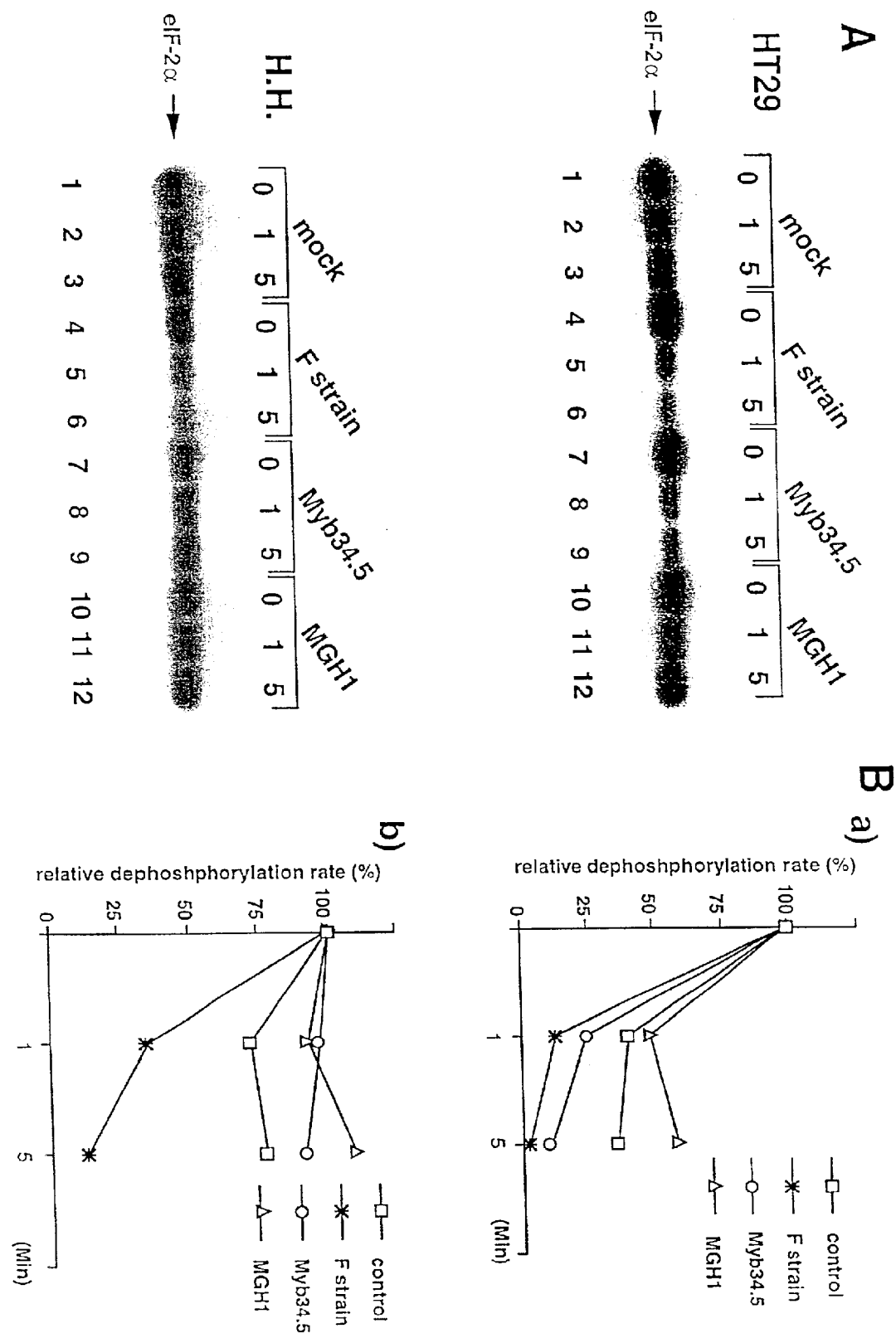
FIGS. 6A and 6B depict an in vitro eIF-2α dephosphorylation assay.

HSV-1 circumvents the consequences of PKR activation by expression of $\gamma_1 34.5$ (FIG. 5). HSV-1 $\gamma_1 34.5$ contains sequences that share homology with the GADD 34 protein (He, B., et al., *J. Biol. Chem.* 273:20737–20743 (1998)), which normally interacts with protein phosphatase-1α to dephosphorylate eIF-2α. Following HSV-1 infection, $\gamma_1 34.5$ interacts with cellular protein phosphatase-1α to dephosphorylate eIF-2α, which prevents shut off of cellular protein synthesis. Id As a consequence of this vital role of $\gamma_1 34.5$, HSV-1 mutants that are defective in $\gamma_1 34.5$ expression display attenuated replication and virulence (Chou, J., et al., *Science* 250:1262–1266 (1990)). For example, HSV-1 mutants R3616 and MGH1 are both completely defective in their expression of $\gamma_1 34.5$ and the magnitude of their replication is reduced compared to that of wild-type HSV-1 (Chou, J., et al., *Science* 250:1262–1266 (1990); Kramm, C. M., et al., *Hum. Gene Ther.* 8:2057–2068 (1997)). MGH1 is essentially identical to another HSV-1 mutant G207 (Hunter, W. D., et al., *J. Virol.* 73:6319–6326 (1999); Mineta, T., et al., *Nat. Med* 1:938–943 (1995); Kooby, D. A., et al., *FASEB J.* 13:1325–1334 (1999)), which has been examined in a clinical trial for brain tumor patients (Martuza, R. L., *J. Clin. Invest.* 105:841–846 (2000)). In addition to lacking $\gamma_1 34.5$, these mutants are defective in expression of viral ribonucleotide reductase (ICP6). The absence of both $\gamma_1 34.5$ and ICP6 further reduces viral replication compared to HSV-1 mutants that are deficient in only one of the two genes, and these double mutants are substantially attenuated. In a direct comparison, replication of the single mutants R3616 and hrR3 in colon carcinoma cells is two log orders greater than that of the double mutant MGH1. However, when $\Delta_1 34.5$ expression is regulated by the B-myb promoter such as in Myb34.5, viral replication in colon carcinoma cells is as robust as that of single mutants, whereas viral replication in normal hepatocytes is as attenuated as that of the double mutant MGH1.

A large percentage of patients with colorectal carcinoma liver metastases develop metastases only in the liver and without evidence of disease in other sites (August, D. A., et al., *Cancer Metastasis Rev.* 3:303–324 (1984)). Because of this tumor biology, several approaches to regional (hepatic) therapy for colorectal carcinoma liver metastases have been examined in clinical trials (Yoon, S. S. and Tanabe, K. K., *Oncologist.* 4:197–208 (1999)). The hepatic tumor burden in patients with colon carcinoma liver metastases is generally greater than that which was treated in this study. However, Myb34.5 replication is two to three log orders greater in human colon carcinoma cells than in murine colon carcinoma cells. In addition, the virus can be administered into the hepatic artery in patients, whereas in this study it was necessarily delivered into the portal blood supply. Liver metastases derive most of their blood supply from the hepatic arterial circulation while the normal liver derives most of its blood supply from the portal circulation (Breedis, C. and Young, G., Am. *J. Pathol.* 30:969–985 (1954)). Substantially higher concentrations of therapeutic agents in liver metastases can be achieved by hepatic arterial delivery compared to portal venous delivery (Ensminger, W. D. and Gyves, J. W., Semis Oncol. 10:176–182 (1983)). Finally, treatment in the mouse model was necessarily limited to a single dose because of technical constraints, whereas patients may be treated with multiple doses.

Both innate and elicited anti-viral responses reduce the efficiency of HSV-1-mediated oncolysis of tumors following intravascular delivery in the brain (Ikeda, K., et al., Nat. Med 5:881–887 (1999)). However, delivery through the vasculature into liver is likely to be much more efficient than delivery into the brain. Biodistribution studies of HSV-1 after intravenous administration demonstrates that a majority of virus localizes to the liver (Schellingerhout, D., et al., Hum. Gene Ther. 9:1543–1549 (1998)(published erratum appears in Hum Gene Ther 20:2652 (1998)). It is thus possible that the effect of innate and elicited anti-viral responses may not be as limiting for tumors in the liver as for tumors in the brain. Equally impressive Myb34.5-mediated oncolysis of liver metastases was observed in naive mice as in mice with neutralizing antibodies to HSV-1. This is an important finding, given that the prevalence of antibodies to HSV-1 in the United States is as high as 80% in some populations (Becker, T. M., et al., Sex. Transm. Dis. 23:138–144 (1996)). We have previously demonstrated that the HSV-1-mediated anti-neoplastic activity observed in this liver metastases model is dependent on viral replication and independent of host immune responses (Yoon, S. S., et al., FASEB J. 14:301–311 (2000)). The importance of this lies in the observation that responses to immunotherapy observed in mouse models are often not reproducible in humans.

Myb34.5 effectively destroys diffuse liver metastases following intravascular administration. It is attenuated compared to wild-type strains and HSV-1 vectors harboring a single mutation. Myb34.5 can be safely administered to animals and its biodistribution is much more restricted than that of wild-type HSV-1. These encouraging results warrant pursuit of clinical studies of Myb34.5 in the treatment of patients with liver metastases.

Modifications of the above-described modes for carrying out the invention that are obvious to persons of skill in medicine, virology, molecular biology, immunology, pharmacology, and/or related fields are intended to be within the scope of the following claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

Although the foregoing invention has been described in some detail by way of illustration and example for purposes of clarity of understanding, it will be obvious that certain changes and modifications can be practiced within the scope of the appended claims.

What is claimed is:

1. A cell-specific and/or tumor-specific herpes viral mutant, comprising:
    (a) a deletion or inactivating mutation in both copies of the gene encoding γ34.5; and
    (b) an insertion of at least one copy of the γ34.5 gene under the transcriptional control of a cell-specific and/or tumor-specific promoter, such that said herpes viral mutant is capable of selective cell- and/or tumor-specific targeted expression.

2. The herpes viral mutant of claim 1, wherein said herpes virus is herpes simplex virus type 1.

3. The herpes viral mutant of claim 2, wherein said tumor-specific promoter is DF3 (MUC1), alpha-fetoprotein (AFP), carcinoembryonic antigen (CEA), prostate specific antigen (PSA), tyrosinase, B-myb, or c-erbB2.

4. The herpes viral mutant of claim 3, wherein said tumor-specific promoter is B-myb.

5. The herpes viral mutant of claim 2, wherein said cell-specific promoter is endothelial nitric oxide synthase (eNOS) promoter expressed in endothelial cells; vascular endothelial growth factor (VEGF) receptor (flk1) promoter expressed in endothelial cells; insulin promoter expressed in beta cells of the pancreas; promoter of gonadotropin-releasing hormone receptor gene expressed in cells of the hypothalamus; matrix metalloproteinase 9 promoter, expressed in osteoclasts and keratinocytes; promoter of parathyroid hormone receptor expressed in bone cells; or dopamine beta-hydroxylase promoter expressed in noradrenergic neurons.

6. The herpes viral mutant of claim 1, wherein said herpes virus is herpes simplex virus type 2.

7. The herpes viral mutant Myb34.5 as represented by ATCC Patent Deposit Designation PTA-4963.

8. A method for selectively killing neoplastic cells using a herpes viral mutant, comprising:
   infecting neoplastic cells with a herpes viral mutant, wherein said neoplastic cells overexpress a known tumor-specific protein, and said viral mutant comprises:
   (a) a deletion or inactivating mutation in a gene encoding γ34.5; and
   (b) an insertion of at least one copy of said γ34.5 gene under the transcriptional control of a promoter of said tumor-specific protein, such that said promoter drives expression of said γ34.5 gene; and
   selectively killing said neoplastic cells.

9. The method of claim 8, wherein said neoplastic cells are nervous system neoplastic cells.

10. The method of claim 9, wherein said nervous system neoplastic cells are central nervous system neoplastic cells.

11. The method of claim 8, wherein said neoplastic cells are peripheral neoplastic cells.

12. The method of claim 11, wherein said peripheral neoplastic cells are metastatic colon cells.

13. The method of claim 8, wherein said herpes viral mutant further comprises at least one additional endogenous deletion or inactivating mutation of a herpes viral gene.

14. The method of claim 13, wherein said additional endogenous deletion or inactivating mutation of a herpes viral gene is in a gene that encodes ribonucleotide reductase (RR), thymidine kinase (TK), uracil DNA glycosylase (UNG), or dUTPase.

15. The method of claim 8, wherein said viral mutant is Myb34.5 as represented by ATCC Patent Deposit Designation PTA-4963.

16. The method of claim 8, wherein said viral mutant further comprises a suicide gene that activates a chemotherapeutic agent, and said method further comprises administering said chemotherapeutic agent.

17. The method of claim 16, wherein said suicide gene encodes cytochrome P450.

18. The method of claim 17, wherein said cytochrome P450 is selected from the group consisting of P450 2B1, P450 2B6, P450 2A6, P450 2C6, P450 2C8, P450 2C9, P450 2C11, and P450 3A4.

19. The method of claim 18, wherein said cytochrome P450 is P450 2B1.

20. The method of claim 16, wherein said chemotherapeutic agent is cyclophosphamide or ifosfamide.

21. The method of claim 8, wherein said tumor-specific protein is DF3 (MUC1), alpha-fetoprotein (AFP), carcinoembryonic antigen (CEA), prostate specific antigen (PSA), tyrosinase, B-myb, or c-erbB2.

22. The method of claim 21, wherein said tumor-specific protein is B-myb.

23. The method of claim 22, where said herpes viral mutant is Myb34.5 as represented by ATCC Patent Deposit Designation PTA-4963.

24. A method for selectively eliminating a target cell population using a herpes viral mutant, comprising:
   infecting target cells with a herpes viral mutant, wherein said target cells overexpress a known cell-specific protein, and said viral mutant comprises:
   (a) a deletion or inactivating mutation in a gene encoding γ34.5; and
   (b) an insertion of at least one copy of said γ34.5 gene under the transcriptional control of a promoter of said cell-specific protein, such that said promoter drives expression of said γ34.5 gene; and
   selectively eliminating said target cells.

25. The method of claim 24, wherein said cell-specific protein is: endothelial nitric oxide synthase (eNOS) expressed in endothelial cells; vascular endothelial growth factor (VEGF) receptor (flk1) expressed in endothelial cells; insulin expressed in beta cells of the pancreas; gonadotropin-releasing hormone receptor gene expressed in cells of the hypothalamus; matrix metalloproteinase 9 expressed in osteoclasts and keratinocytes; of parathyroid hormone receptor expressed in bone cells; or dopamine beta-hydroxylase expressed in noradrenergic neurons.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 1
ggaggcgccc aagcgtccgg ccg                                       23

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 2
tggggtacag gctggcaaag t                                         21
```